(12) United States Patent
Prakash et al.

(10) Patent No.: US 9,169,285 B2
(45) Date of Patent: Oct. 27, 2015

(54) METHODS FOR PURIFYING STEVIOL GLYCOSIDES AND USES OF THE SAME

(71) Applicants: The Coca-Cola Company, Atlanta, GA (US); PureCircle Sdn Bhd, Negeri Sembilan (MY)

(72) Inventors: Indra Prakash, Alpharetta, GA (US); Avetik Markosyan, Kuala Lumpur (MY); Venkata Sai Prakash Chaturvedula, Mission Viejo, CA (US); Mary Campbell, Acworth, GA (US); Rafael San Miguel, Atlanta, GA (US); Siddhartha Purkayastha, Lombard, IL (US); Marquita Johnson, Oak Lawn, IL (US)

(73) Assignees: The Coca-Cola Company, Atlanta, GA (US); Purecircle SDN BHD (MY)

( * ) Notice: Subject to any disclaimer, the term of this patent is extended or adjusted under 35 U.S.C. 154(b) by 0 days.

(21) Appl. No.: 14/033,563

(22) Filed: Sep. 23, 2013

(65) Prior Publication Data
US 2014/0099403 A1    Apr. 10, 2014

Related U.S. Application Data

(63) Continuation of application No. PCT/US2012/070562, filed on Dec. 19, 2012.

(60) Provisional application No. 61/577,202, filed on Dec. 19, 2011, provisional application No. 61/651,099, filed on May 24, 2012.

(51) Int. Cl.
| | |
|---|---|
| A23L 1/236 | (2006.01) |
| A23L 2/00 | (2006.01) |
| C07H 15/24 | (2006.01) |
| A23L 2/60 | (2006.01) |
| A23L 1/09 | (2006.01) |
| C07H 1/08 | (2006.01) |

(52) U.S. Cl.
CPC . *C07H 15/24* (2013.01); *A23L 1/09* (2013.01); *A23L 1/097* (2013.01); *A23L 1/236* (2013.01); *A23L 1/2363* (2013.01); *A23L 1/2364* (2013.01); *A23L 1/2366* (2013.01); *A23L 2/00* (2013.01); *A23L 2/60* (2013.01); *C07H 1/08* (2013.01)

(58) Field of Classification Search
CPC ........... A23L 1/09; A23L 1/097; A23L 1/236; A23L 1/2363; A23L 1/2364; A23L 1/2366; A23L 2/00; A23L 2/60; C07H 1/08; C07H 15/24
USPC .......................................... 426/548, 590, 658
See application file for complete search history.

(56) References Cited

U.S. PATENT DOCUMENTS

| | | |
|---|---|---|
| 2007/0882106 | 4/2007 | Lee et al. |
| 2007/0116823 A1* | 5/2007 | Prakash et al. ................ 426/548 |
| 2010/0316782 A1 | 12/2010 | Shi et al. |
| 2011/0160311 A1 | 6/2011 | Prakash et al. |
| 2014/0342043 A1* | 11/2014 | Bell et al. ........................ 426/72 |

FOREIGN PATENT DOCUMENTS

| | | |
|---|---|---|
| WO | WO 2010038911 A1 | 4/2010 |
| WO | WO 2011094423 A1 | 8/2011 |
| WO | WO 2011112892 A1 | 9/2011 |
| WO | 2012129451 A1 † | 9/2012 |

OTHER PUBLICATIONS

International Search Report for PCT/US2012/070562, Published Jun. 27, 2013.
Ohta, M., et al., "Characterization of Novel Steviol Glycosides from Leaves of *Stevia rebaudiana* Morita". *J. Appl. Glycosci.*, 57, 199-209 (2010).
Third Party Submission in PCT/US2012/070562, submitted Mar. 12, 2014.
Dubois, G., et al. 1991. Concentration-response relationships of sweeteners: a systematic study. In *Sweeteners: Discovery, Molecular Design and Chemoreception*, ed. DE Walters, FT Orthoefer, GE DuBois, pp. 261-276.
Glycosides from Leaves of *Stevia rebaudiana* Morita, pp. 199-209, 2010, Journal of Applied Glycoscience 57, The Japanese Society of Ohta, Applied Glycoscience, Mainichi Academic Forum Inc, Hitotsubashi, Tokyo, Japan.†

* cited by examiner
† cited by third party

*Primary Examiner* — Leslie Wong
(74) *Attorney, Agent, or Firm* — King & Spalding

(57) ABSTRACT

Methods for purifying steviol glycosides, including Rebaudioside X, are provided herein. Sweetener and sweetened containing Rebaudioside X are also provided herein. Methods of improving the flavor and/or temporal profile of sweetenable compositions, such as beverages, are also provided.

36 Claims, 33 Drawing Sheets

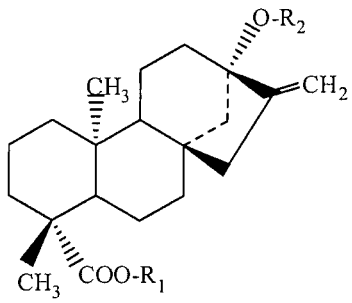

| Compound name | $R_1$ (C-19) | $R_2$ (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1) <br> β-Glc(3→1) |
| 7. Rebaudioside B | H | β-Glc-β-Glc(2→1) <br> β-Glc(3→1) |
| 8. Rebaudioside C (Dulcoside B) | β-Glc | β-Glc-α-Rha(2→1) <br> β-Glc(3→1) |
| 9. Rebaudioside D | β-Glc-β-Glc(2→1) | β-Glc-β-Glc(2→1) <br> β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1) <br> β-Glc(3→1) |
| 12. Dulcoside A | β-Glc | β-Glc-α-Rha(2→1) |

FIG. 1

Steviol

Stevioside

Rebaudioside A

Rebaudioside B

Rebaudioside C

Rebaudioside D

Rebaudioside E

Rebaudioside F

Dulcoside A

Steviolbioside

Rubusoside

| No. | (ppm) | Height | No. | (ppm) | Height | No. | (ppm) | Height | No. | (ppm) | Height | No. | (ppm) | Height |
|---|---|---|---|---|---|---|---|---|---|---|---|---|---|---|
| 1 | 17.03 | 0.0551 | 12 | 44.54 | 0.0484 | 23 | 71.59 | 0.0327 | 34 | 78.25 | 0.0544 | 45 | 104.21 | 0.0351 |
| 2 | 19.91 | 0.0168 | 13 | 46.78 | 0.0208 | 24 | 73.50 | 0.0297 | 35 | 78.36 | 0.0377 | 46 | 104.40 | 0.0384 |
| 3 | 20.48 | 0.0187 | 14 | 54.58 | 0.0298 | 25 | 73.85 | 0.0307 | 36 | 78.72 | 0.0398 | 47 | 104.47 | 0.0330 |
| 4 | 23.74 | 0.0204 | 15 | 57.66 | 0.0326 | 26 | 75.76 | 0.0355 | 37 | 78.77 | 0.0378 | 48 | 105.02 | 0.0323 |
| 5 | 28.52 | 0.0541 | 16 | 62.06 | 0.0278 | 27 | 75.88 | 0.0350 | 38 | 78.92 | 0.0354 | 49 | 105.17 | 0.0191 |
| 6 | 38.70 | 0.0270 | 17 | 62.34 | 0.0627 | 28 | 76.02 | 0.0304 | 39 | 81.65 | 0.0303 | 50 | 123.31 | 0.0117 |
| 7 | 40.03 | 0.0477 | 18 | 62.85 | 0.0280 | 29 | 77.15 | 0.0291 | 40 | 87.85 | 0.0435 | 51 | 123.60 | 0.9896 |
| 8 | 40.59 | 0.0180 | 19 | 64.25 | 0.0757 | 30 | 77.89 | 0.0372 | 41 | 87.85 | 0.0306 | 52 | 123.84 | 1.0000 |
| 9 | 41.47 | 0.0471 | 20 | 70.35 | 0.0309 | 31 | 77.99 | 0.0428 | 42 | 88.90 | 0.0305 | 53 | 124.09 | 0.9870 |
| 10 | 42.85 | 0.0185 | 21 | 70.65 | 0.0312 | 32 | 78.06 | 0.0438 | 43 | 95.18 | 0.0294 | 54 | 124.34 | 0.0143 |
| 11 | 43.60 | 0.0204 | 22 | 71.39 | 0.0331 | 33 | 78.10 | 0.0428 | 44 | 96.50 | 0.0293 | 55 | 135.64 | 0.5908 |
| | | | | | | | | | | | | 56 | 135.88 | 0.6172 |
| | | | | | | | | | | | | 57 | 138.18 | 0.5808 |
| | | | | | | | | | | | | 58 | 149.90 | 0.9379 |
| | | | | | | | | | | | | 59 | 150.17 | 0.9441 |
| | | | | | | | | | | | | 60 | 150.44 | 0.9084 |
| | | | | | | | | | | | | 61 | 153.60 | 0.0316 |
| | | | | | | | | | | | | 62 | 177.15 | 0.0314 |

FIG. 7B

| No. | (ppm) | Height | No. | (ppm) | Height | No. | (ppm) | Height | No. | (ppm) | Height | No. | (ppm) | Height | No. | (ppm) | Height |
|---|---|---|---|---|---|---|---|---|---|---|---|---|---|---|---|---|---|
| 1 | 0.75 | 0.0111 | 15 | 1.35 | 0.2170 | 29 | 1.88 | 0.0375 | 43 | 3.74 | 0.0137 | 57 | 3.91 | 0.0210 | 71 | 4.08 | 0.0886 |
| 2 | 0.78 | 0.0182 | 16 | 1.41 | 0.0142 | 30 | 1.90 | 0.0343 | 44 | 3.75 | 0.0189 | 58 | 3.92 | 0.0239 | 72 | 4.10 | 0.0730 |
| 3 | 0.80 | 0.0101 | 17 | 1.43 | 0.0407 | 31 | 2.04 | 0.0308 | 45 | 3.76 | 0.0194 | 59 | 3.93 | 0.0229 | 73 | 4.14 | 0.1293 |
| 4 | 0.93 | 0.0331 | 18 | 1.45 | 0.0165 | 32 | 2.07 | 0.0277 | 46 | 3.77 | 0.0282 | 60 | 3.93 | 0.0267 | 74 | 4.18 | 0.1484 |
| 5 | 0.96 | 0.0346 | 19 | 1.48 | 0.0076 | 33 | 2.08 | 0.0221 | 47 | 3.77 | 0.0219 | 61 | 3.94 | 0.0280 | 75 | 4.18 | 0.1306 |
| 6 | 1.00 | 0.0361 | 20 | 1.55 | 0.0132 | 34 | 2.25 | 0.0298 | 48 | 3.78 | 0.0164 | 62 | 3.95 | 0.0249 | 76 | 4.19 | 0.0433 |
| 7 | 1.01 | 0.0128 | 21 | 1.67 | 0.0182 | 35 | 2.29 | 0.0345 | 49 | 3.85 | 0.0178 | 63 | 3.96 | 0.0343 | 77 | 4.20 | 0.0432 |
| 8 | 1.03 | 0.0204 | 22 | 1.68 | 0.0160 | 36 | 2.31 | 0.0280 | 50 | 3.85 | 0.0155 | 64 | 3.97 | 0.0378 | 78 | 4.20 | 0.0841 |
| 9 | 1.05 | 0.0217 | 23 | 1.70 | 0.0135 | 37 | 2.34 | 0.0202 | 51 | 3.86 | 0.0182 | 65 | 3.99 | 0.0794 | 79 | 4.21 | 0.0898 |
| 10 | 1.07 | 0.0269 | 24 | 1.72 | 0.0091 | 38 | 2.40 | 0.0078 | 52 | 3.87 | 0.0200 | 66 | 4.00 | 0.0799 | 80 | 4.22 | 0.0906 |
| 11 | 1.10 | 0.0297 | 25 | 1.78 | 0.0307 | 39 | 2.43 | 0.0166 | 53 | 3.88 | 0.0247 | 67 | 4.01 | 0.0878 | 81 | 4.23 | 0.1110 |
| 12 | 1.17 | 0.0360 | 26 | 1.81 | 0.0378 | 40 | 2.46 | 0.0141 | 54 | 3.89 | 0.0248 | 68 | 4.02 | 0.0747 | 82 | 4.24 | 0.1128 |
| 13 | 1.25 | 0.0374 | 27 | 1.82 | 0.0394 | 41 | 2.75 | 0.0379 | 55 | 3.89 | 0.0253 | 69 | 4.03 | 0.0547 | 83 | 4.28 | 0.0290 |
| 14 | 1.30 | 0.0349 | 28 | 1.88 | 0.0233 | 42 | 2.79 | 0.0329 | 56 | 3.90 | 0.0195 | 70 | 4.04 | 0.0551 | 84 | 4.34 | 0.1120 |

FIG. 8C

Rebaudioside X

METHODS FOR PURIFYING STEVIOL GLYCOSIDES AND USES OF THE SAME

CROSS REFERENCE TO RELATED APPLICATIONS

This application is a continuation of International Application No. PCT/US2012/070562, filed Dec. 19, 2012, and claims priority to U.S. Provisional Patent Application No. 61/577,202, filed Dec. 19, 2011, and U.S. Provisional Patent Application No. 61/651,099, filed May 24, 2012. The contents of each of the above-identified patent applications are hereby incorporated by reference in their entirety.

FIELD OF THE INVENTION

The present invention relates generally to a process for purifying one or more steviol glycosides, such as Rebaudioside X (Reb X), from a solution of steviol glycosides. The present invention also relates to sweetener compositions and sweetened compositions containing one or more steviol glycosides, including Reb X, and methods for preparing the same. The present invention also relates to methods of providing a sugar-like flavor and temporal profile to sweetener and sweetened compositions utilizing Reb X.

BACKGROUND OF THE INVENTION

Natural caloric sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or low caloric sweeteners have been introduced to satisfy consumer demand. However, sweeteners within this class differ from natural caloric sugars in ways that continue to frustrate consumers. On a taste basis, non-caloric or low caloric sweeteners exhibit a temporal profile, maximal response, flavor profile, mouth feel, and/or adaptation behavior that differ from sugar. Specifically, non-caloric or low caloric sweeteners exhibit delayed sweetness onset, lingering sweet aftertaste, bitter taste, metallic taste, astringent taste, cooling taste and/or licorice-like taste. On a source basis, many non-caloric or low caloric sweeteners are synthetic chemicals. The desire for a natural non-caloric or low caloric sweetener that tastes like sucrose remains high.

*Stevia rebaudiana* Bertoni is a perennial shrub of the Asteraceae (Compositae) family native to certain regions of South America. Its leaves have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10 to 20% of the total dry weight. These diterpene glycosides are about 150 to 450 times sweeter than sugar. Structurally, the diterpene glycosides are characterized by a single base, steviol, and differ by the presence of carbohydrate residues at positions C13 and C19, as presented in FIGS. 2a-2k. Typically, on a dry weight basis, the four major steviol glycosides found in the leaves of *Stevia* are Dulcoside A (0.3%), Rebaudioside C (0.6-1.0%), Rebaudioside A (3.8%) and Stevioside (9.1%). Other glycosides identified in *Stevia* extract include Rebaudioside B, D, E, and F, Steviolbioside and Rubusoside. Among these, only Stevioside and Rebaudioside A are available on a commercial scale.

Steviol glycosides can be extracted from leaves using either water or organic solvent extraction. Supercritical fluid extraction and steam distillation methods have also been described. Methods for the recovery of diterpene sweet glycosides from *Stevia rebaudiana* using supercritical $CO_2$, membrane technology, and water or organic solvents, such as methanol and ethanol, may also be used.

The use of steviol glycosides has been limited to date by certain undesirable taste properties, including licorice taste, bitterness, astringency, sweet aftertaste, bitter aftertaste, licorice aftertaste, and become more prominent with increase of concentration. These undesirable taste attributes are particularly prominent in carbonated beverages, where full replacement of sugar requires concentrations of steviol glycosides that exceed 500 mg/L. Use at that level results in significant deterioration in the final product taste.

Accordingly, there remains a need to develop natural reduced or non-caloric sweeteners that provide a temporal and flavor profile similar to that of sucrose.

There remains a further need to develop sweetened compositions, such as beverages, that containing natural reduced or non-caloric sweeteners that provide a temporal and flavor profile similar to that of sucrose.

SUMMARY OF THE INVENTION

The present invention provides a method for purifying the steviol glycoside Reb X from a solution of steviol glycosides:

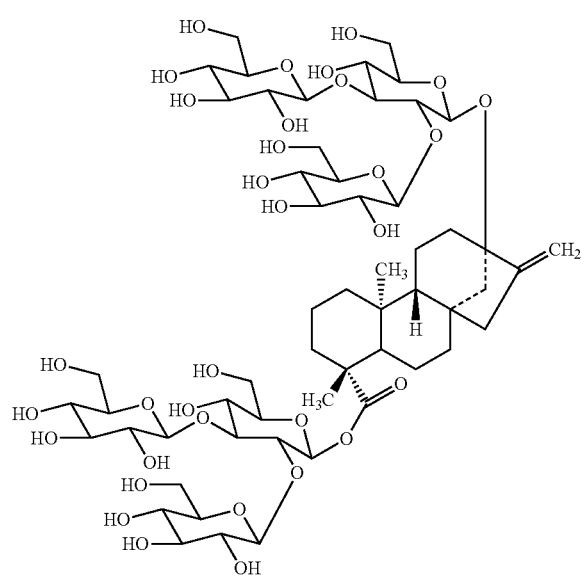

In one embodiment, the present invention is a method for purifying Reb X including passing a solution of steviol glycosides through a multi-column system including a plurality of columns packed with an adsorbent resin to provide at least one column having adsorbed steviol glycosides and eluting fractions with high Reb X content from the at least one column having absorbed steviol glycosides to provide an eluted solution with high Reb X content.

As the solution of steviol glycosides passes through the multi-column system, the various steviol glycosides separate into different portions of different columns. The portions differ from each other both by total steviol glycoside content and individual glycoside (particularly Reb X) content. Fractions containing high Reb X content are eluted/desorbed from the multi-column system separately from fractions containing low Reb X content.

Optionally, the method includes one or more additional steps. In one embodiment, the method includes washing the multi-column system with a washing solution prior to eluting fractions with high Reb X content in order to remove impurities.

In another embodiment, the method optionally includes decolorizing the eluted solution with high Reb X content, removing the alcohol solvent and passing the remaining solution through a column with macroporous adsorbent to provide a second adsorption solution.

In another embodiment, the method optionally includes deionizing the second adsorption solution. The second adsorption solution can then be concentrated to partially remove solvent to provide a high Reb X content mixture containing from about 30% to about 40% solids content.

Further purification can be achieved by mixing a high Reb X content mixture containing from about 30% to about 40% solids with a first alcohol solvent to provide a Reb X solution, inducing crystallization to provide first crystals of Reb X, and separating the first crystals of Reb X from the solution, wherein the first crystals have a purity level greater than about 60% (w/w) on a dry basis. In some embodiments, the purity of the first crystals exceeds 60%, such as, for example, greater than about 65%, greater than about 70%, greater than about 75%, greater than about 80%, greater than about 85%.

To achieve higher purity levels, the first crystals may then be suspended in a second aqueous alcohol solution to provide second crystals of Reb X and a third aqueous alcohol solution. The second crystals of Reb X may be separated from the third aqueous alcohol solution. These second crystals may have a purity level greater than about 90% (w/w) on a dry basis.

Fractions containing low Reb X content can also be further treated according to certain methods provided herein. Optionally, the method includes one or more additional steps. In one embodiment, the method includes washing the multi-column system with a washing solution prior to eluting fractions with low Reb X content in order to remove impurities.

In another embodiment, the method optionally includes decolorizing the eluted solution of steviol glycosides, removing the alcohol solvent and passing the remaining solution through a column with macroporous adsorbent to provide a second adsorption solution.

In another embodiment, the method optionally includes deionizing the eluted solution of steviol glycosides. Removal of the remaining solvent from the eluted solution—optionally decolorized and/or deionized—provides a highly purified steviol glycoside mixture with at least about 95% by weight total steviol glycosides on a dry basis.

The method of the present invention also includes preparing the solution of steviol glycosides. In one embodiment, the solution of steviol glycosides is prepared by providing leaves of the *Stevia rebaudiana* Bertoni plant, producing a crude extract by contacting the leaves with solvent, separating insoluble material from the crude extract to provide a first filtrate containing steviol glycosides, and treating the first filtrate to remove high molecular weight compounds and insoluble particles, thereby providing a second filtrate containing steviol glycosides. The second filtrate is then treated with an ion-exchange resin to remove salts, thereby providing a resin-treated filtrate that serves as the solution of steviol glycosides in the method of the present invention.

The source of the solution of steviol glycosides may vary. In one embodiment, the solution of steviol glycosides may be a commercially available *stevia* extract or steviol glycoside mixture. In another embodiment, the solution of steviol glycosides may be prepared from plant material (e.g. leaves) of the *Stevia rebaudiana* Bertoni plant as described herein. Alternatively, the solution of steviol glycosides may be the by-product of another the isolation and purification processes steviol glycosides from *Stevia rebaudiana* Bertoni plant material.

According to one aspect of the invention, a method for producing purified Reb X comprises the steps of: providing *Stevia rebaudiana* Bertoni plant material; producing a crude extract by contacting the *Stevia rebaudiana* Bertoni plant material with an extracting solvent, such as water; separating insoluble material from the first extract to provide a filtrate containing steviol glycosides; deionizing the filtrate; passing the filtrate feed over a series of columns packed with polar macroporous resin and eluting steviol glycosides to provide eluates containing high Reb X and low Reb X fractions; decolorizing the solutions; evaporating and deionizing; concentrating by nano-filters and drying.

Sweetener compositions comprising Reb X are also provided herein. In one embodiment, Reb X is present in an effective amount to provide a sweetness equivalence from about 0.5 to about 14 degrees Brix of sucrose when present in a sweetened composition. In another embodiment, Reb X is present in an effective amount to provide a sucrose equivalence of greater than about 10% when present in a sweetened composition.

Reb X can be used in any form. In one embodiment, Reb X is the sole sweetener in a sweetener composition. In another embodiment Reb X is provided as part of a composition or mixture. In one embodiment, Reb X is provided in a *Stevia* extract, wherein the Reb X component constitutes from about 5% to about 99% of the *Stevia* extract by weight on a dry basis. In a further embodiment, Reb X is provided in a mixture of steviol glycosides, wherein Reb X constitutes from about 5% to about 99% of the steviol glycoside mixture by weight on a dry basis.

The sweetener compositions can also contain one or more additional sweeteners, including, for example, natural sweeteners, high potency sweeteners, carbohydrate sweeteners, synthetic sweeteners and combinations thereof.

Particularly desirable sweetener compositions comprise Reb X and a compound selected from the group consisting of Reb A, Reb B, Reb D, NSF-02, mogroside V, erythritol or combinations thereof.

The sweetener compositions can also contain on or more additives including, for example, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

The sweetener compositions can also contain one or more functional ingredients, such as, for example, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Methods of preparing sweetener compositions are also provided. In one embodiment, a method for preparing a sweetener composition comprises combining Reb X and at least one sweetener and/or additive and/or functional ingredient. In another embodiment, a method for preparing a sweetener composition comprises combining a composition comprising Reb X and at least one sweetener and/or additive and/or functional ingredient.

Sweetened composition containing Reb X or the sweetener compositions of the present invention are also provided herein. Sweetened compositions include, for example, pharmaceutical compositions, edible gel mixes and compositions, dental compositions, foodstuffs, beverages and beverage products.

Methods of preparing sweetened compositions are also provided herein. In one embodiment, a method for preparing a sweetened composition comprises combining a sweetenable composition and Reb X. The method can further include adding one or more sweetener, additive and/or functional ingredient. In another embodiment, a method for preparing a sweetened composition comprises combining a sweetenable composition and a sweetener composition comprising Reb X. The sweetener composition can optionally comprise one or more sweetener, additive and/or functional ingredient.

In particular embodiments, beverages containing Reb X or the sweetener compositions of the present invention are also provided herein. The beverages contain a liquid matrix, such as, for example, deionized water, distilled water, reverse osmosis water, carbon-treated water, purified water, demineralized water, phosphoric acid, phosphate buffer, citric acid, citrate buffer and carbon-treated water.

Full-calorie, mid-calorie, low-calorie and zero-calorie beverages containing Reb X or the sweetener compositions of the present invention are also provided.

Methods of preparing beverages are also provided herein. In one embodiment, a method for preparing a beverage comprises combining Reb X and a liquid matrix. The method can further comprise adding one or more sweeteners, additives and/or functional ingredients to the beverage. In another embodiment, a method for preparing a beverage comprises combining a sweetener composition comprising Reb X and a liquid matrix.

Tabletop sweetener compositions containing Reb X or the sweetener compositions of the present invention are also provided herein. The tabletop composition can further include at least one bulking agent, additive, anti-caking agent, functional ingredient and combinations thereof. The tabletop sweetener composition can be present in the form of a solid or a liquid. The liquid tabletop sweetener can comprise water, and optionally additives, such, as for example polyols (e.g. erythritol, sorbitol, propylene glycol or glycerol), acids (e.g. citric acid), antimicrobial agents (e.g. benzoic acid or a salt thereof).

Delivery systems comprising Reb X or the sweetener compositions of the present invention are also provided herein, such as, for example, co-crystallized sweetener compositions with a sugar or a polyol, agglomerated sweetener compositions, compacted sweetener compositions, dried sweetener compositions, particle sweetener compositions, spheronized sweetener compositions, granular sweetener compositions, and liquid sweetener compositions.

Finally, a method for imparting a more sugar-like temporal profile, flavor profile, or both to a sweetened composition comprises combining a sweetenable composition with Reb X or the sweetener compositions of the present invention is also provided herein. The method can further include the addition of other sweeteners, additives, functional ingredients and combinations thereof.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 1 shows the chemical structure of steviol glycosides in the *Stevia rebaudiana* Bertoni leaves.

FIGS. 7a, 7b. shows the $^{13}$C NMR spectrum of Reb X (150 MHz, $C_5D_5N$).

FIGS. 8a, 8b, 8c. shows the $^1$H NMR spectrum of Reb X (600 MHz, $C_5D_5N$).

DETAILED DESCRIPTION OF THE INVENTION

Figure 2A:
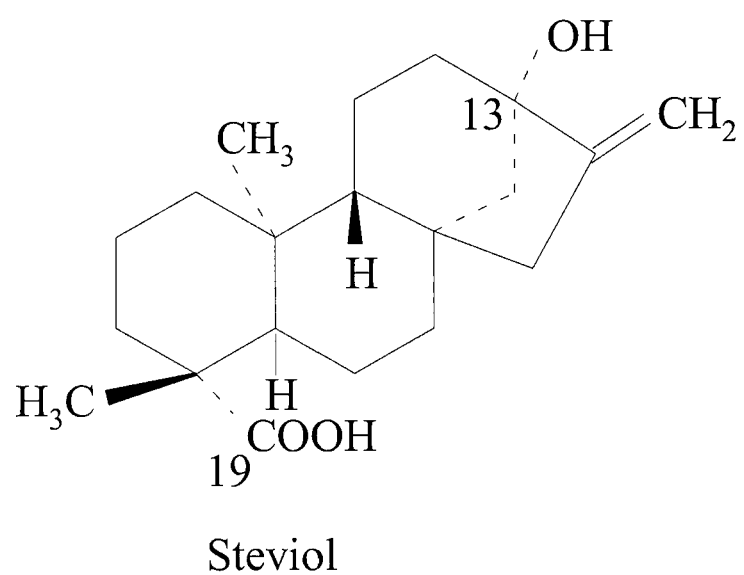
FIGS. 2a-2k show the chemical structures of *Stevia rebaudiana* Bertoni glycosides.
Figure 2B:
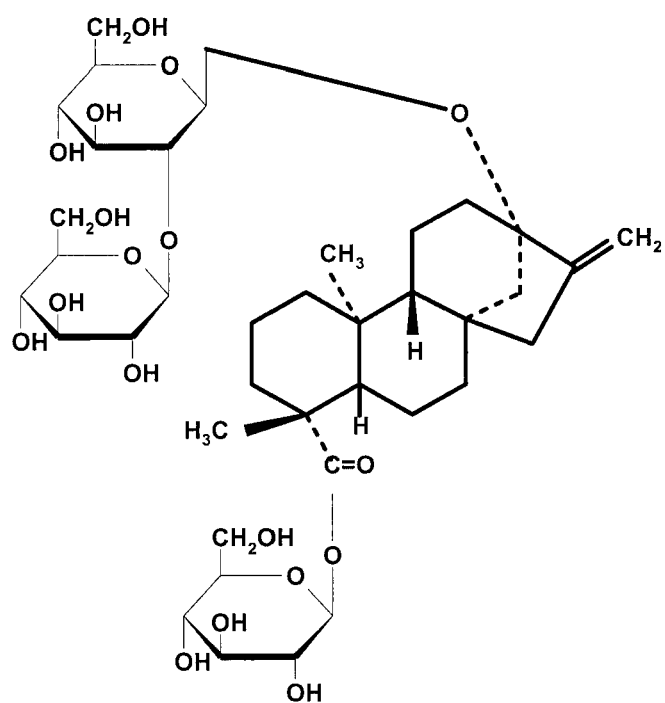
Figure 2C:
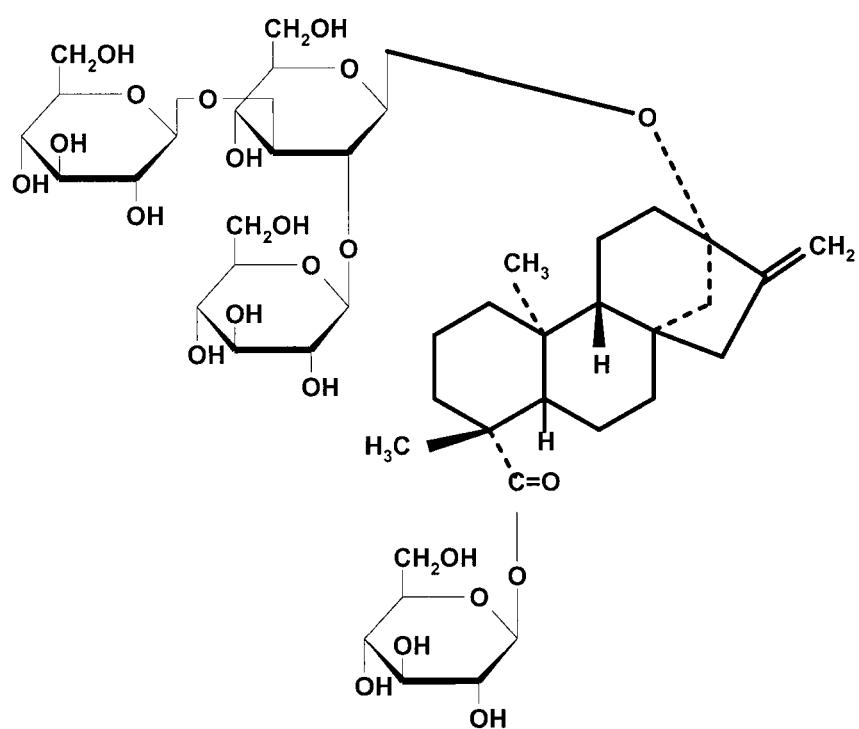
Figure 2D:
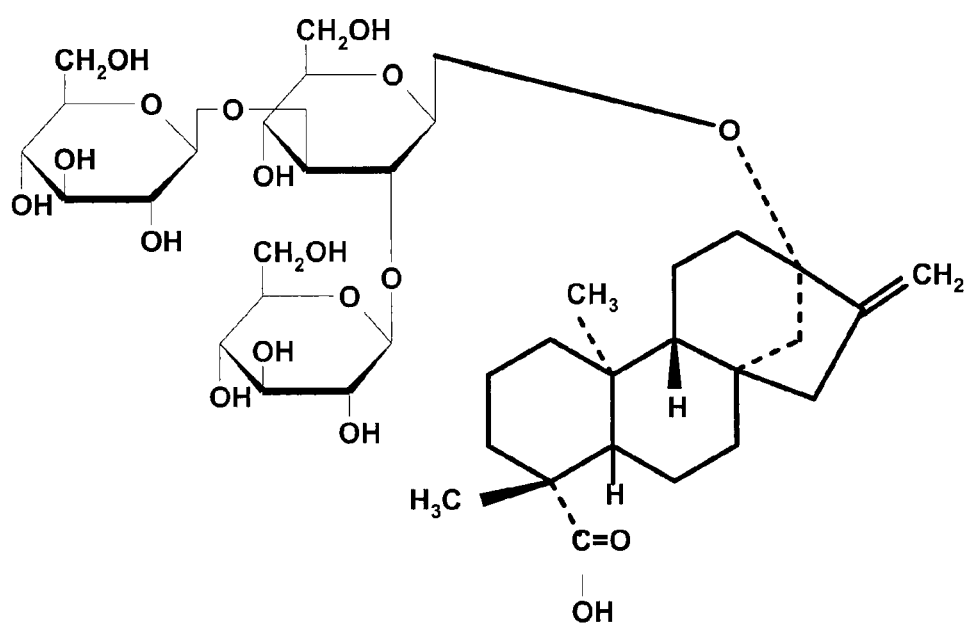
Figure 2E:
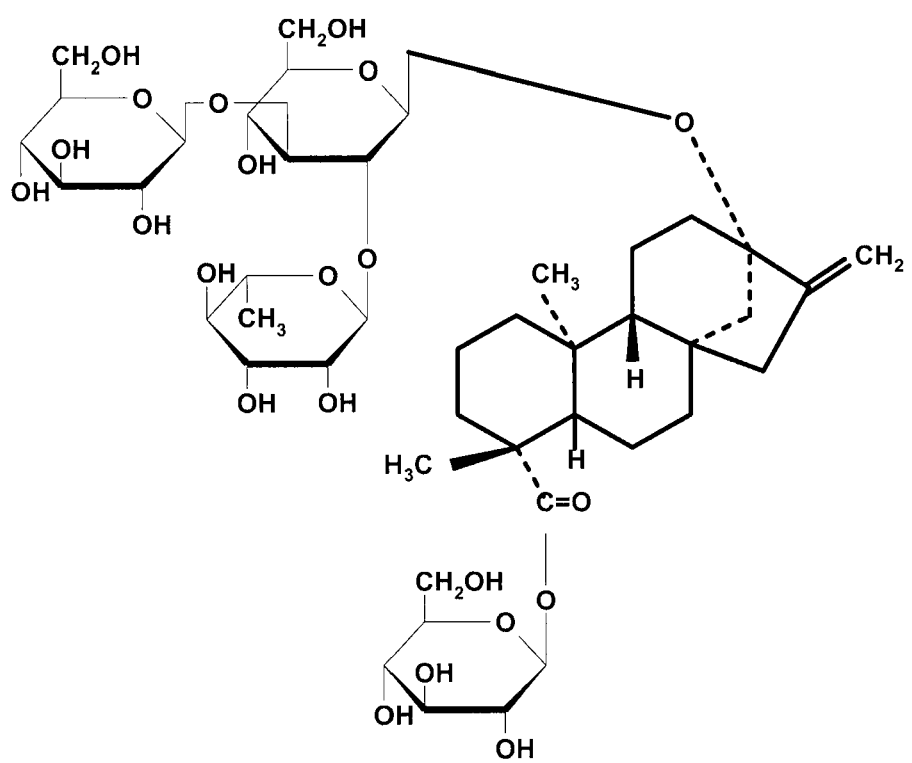
Figure 2F:
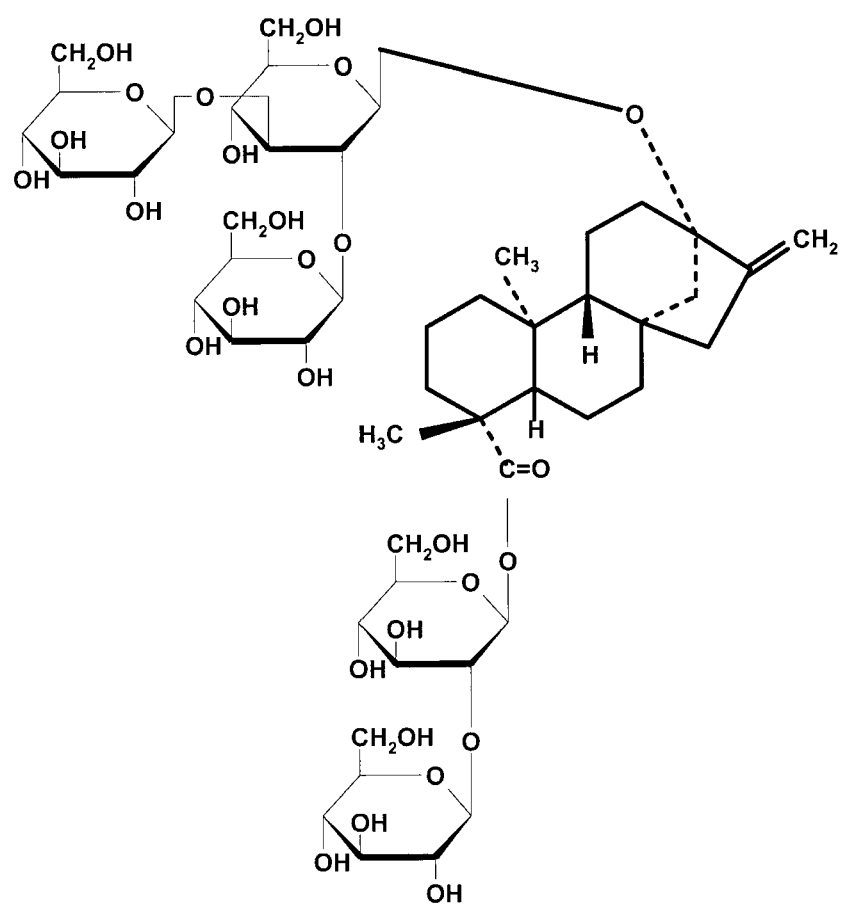
Figure 2G:
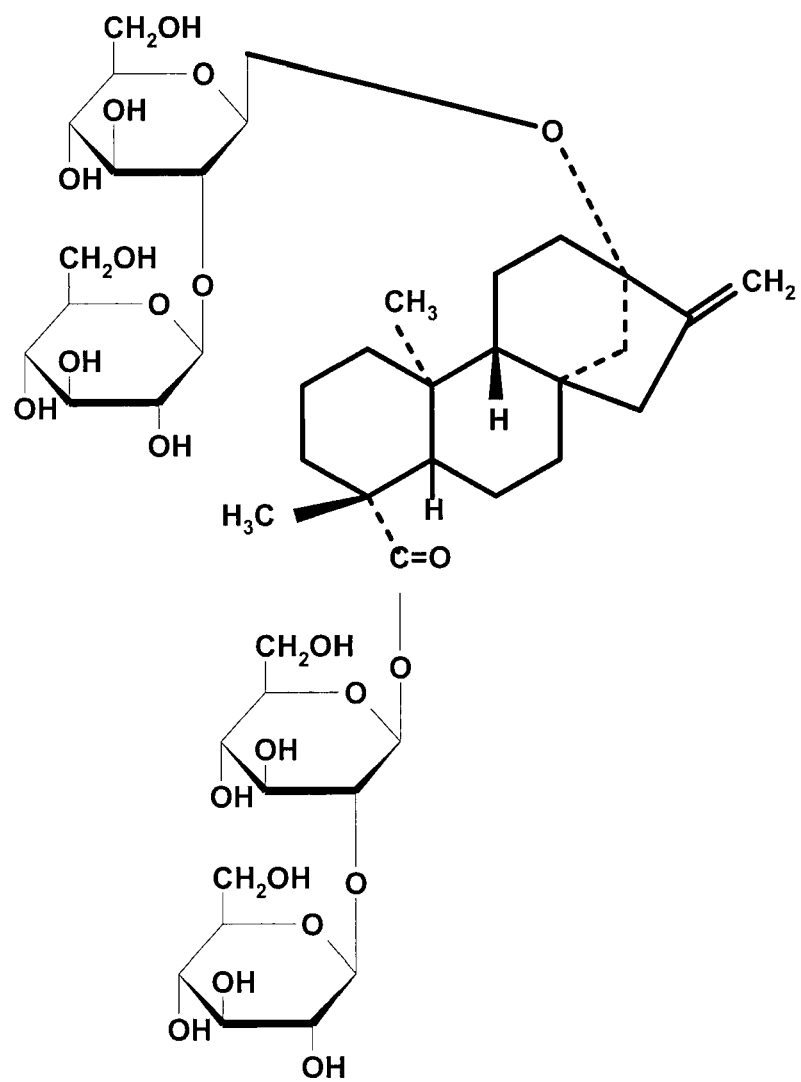
Figure 2H:
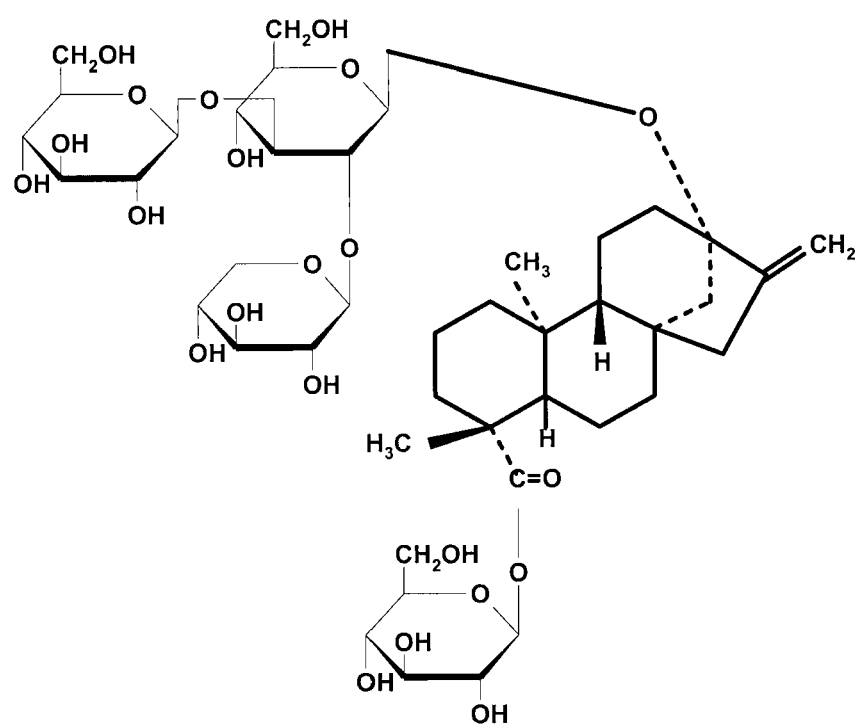
Figure 2I:
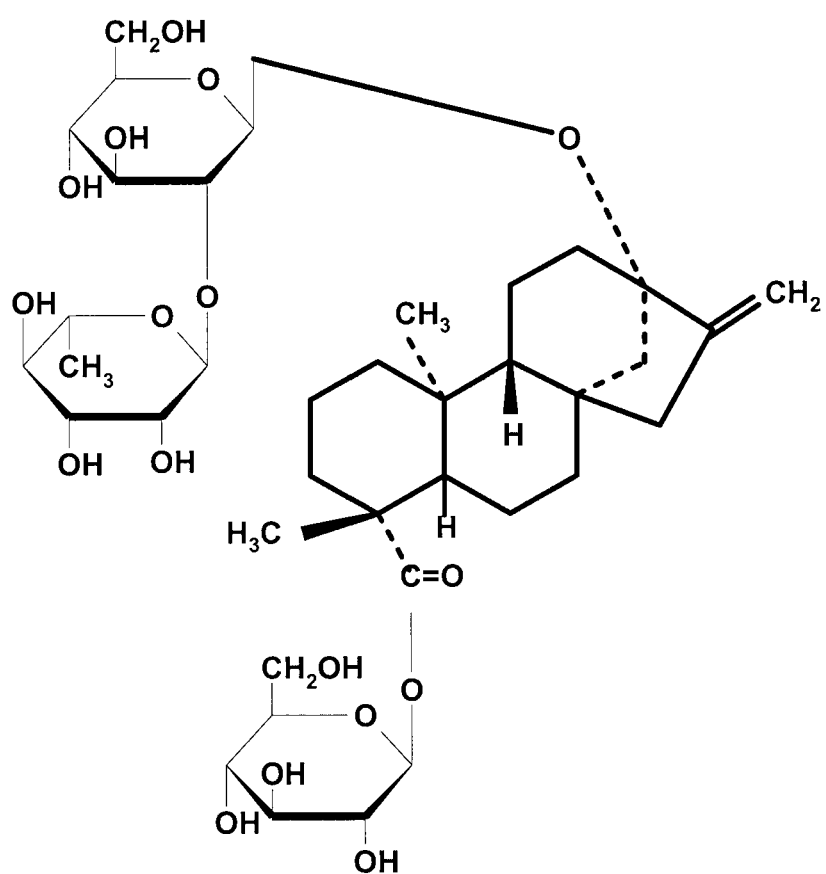
Figure 2J:
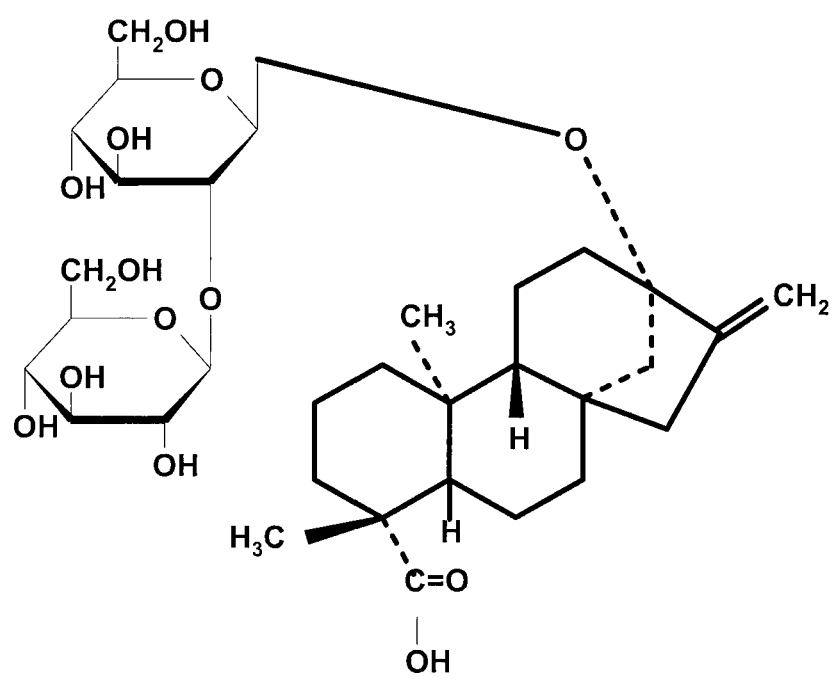
Figure 2K:
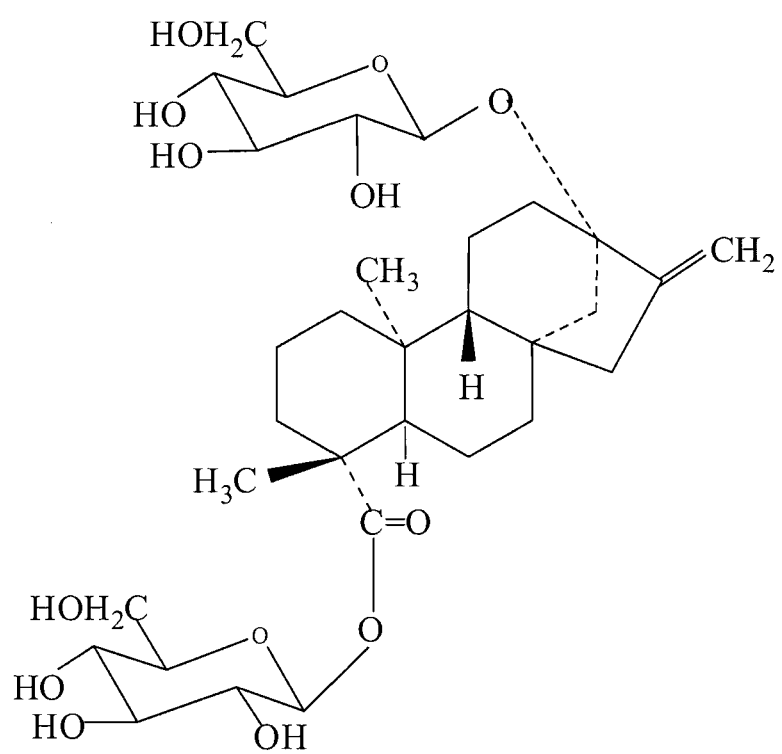
Figure 3A:
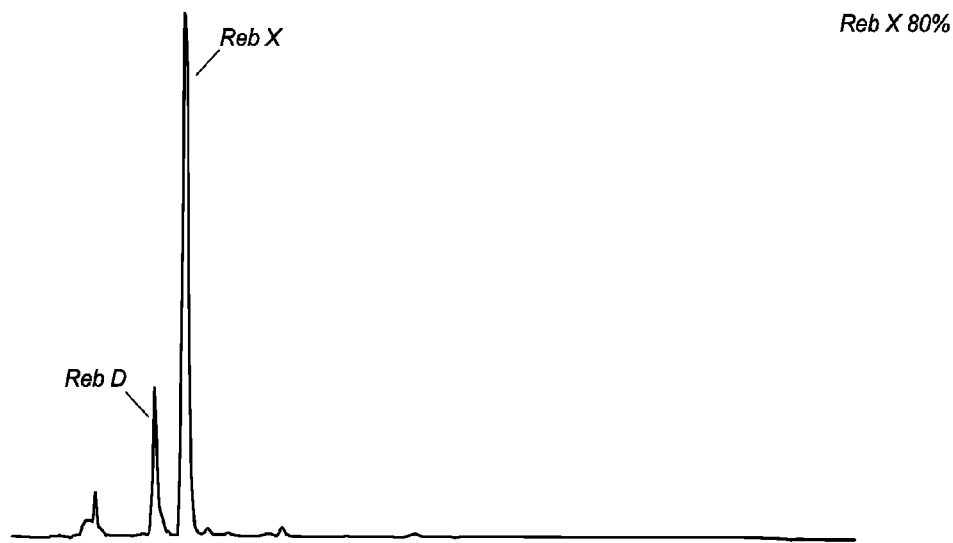
FIGS. 3a, 3b show HPLC traces of Reb X at various stages of purification. 3a shows the HPLC trace of 80% pure Reb X. 3b shows the HPLC trace of 97% Reb X (HPLC conditions provided in "Eluting the adsorbed steviol glycosides" section).
Figure 3B:
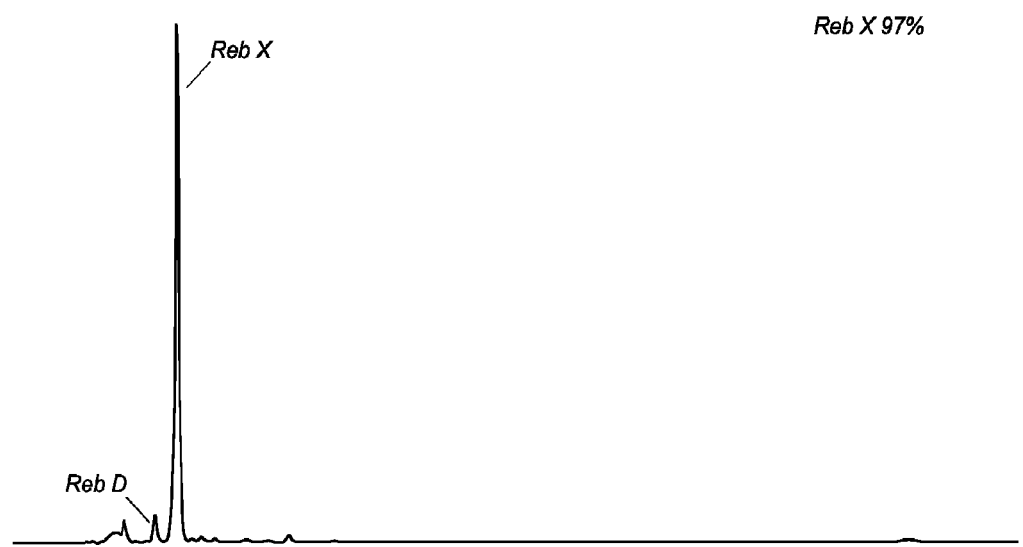
Figure 4:
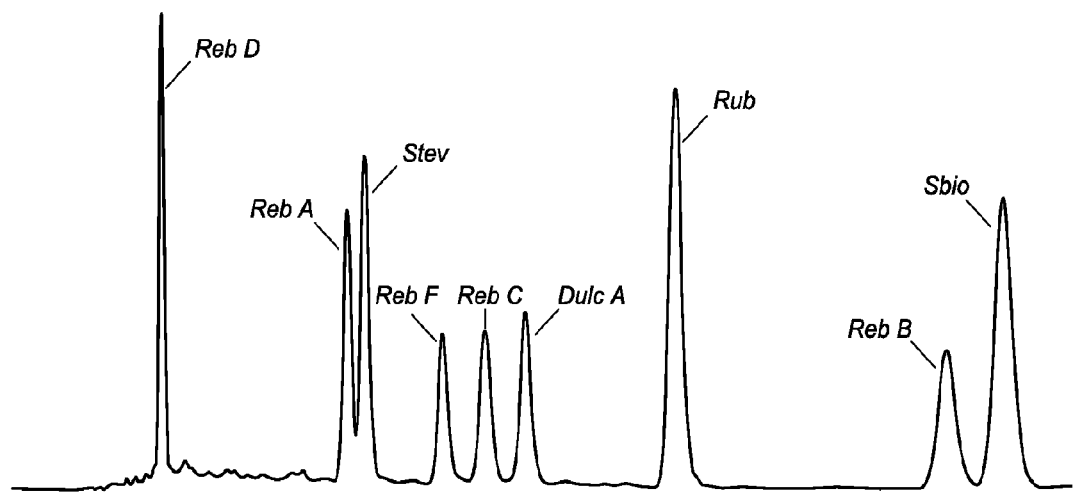
FIG. 4 shows the HPLC trace of Reb A, Reb B, Reb C, Reb D, Reb F, Stevioside, Dulcoside A, Steviolbioside and Rubusoside reference standards (HPLC conditions provided in "Eluting the adsorbed steviol glycosides" section).
Figure 5:
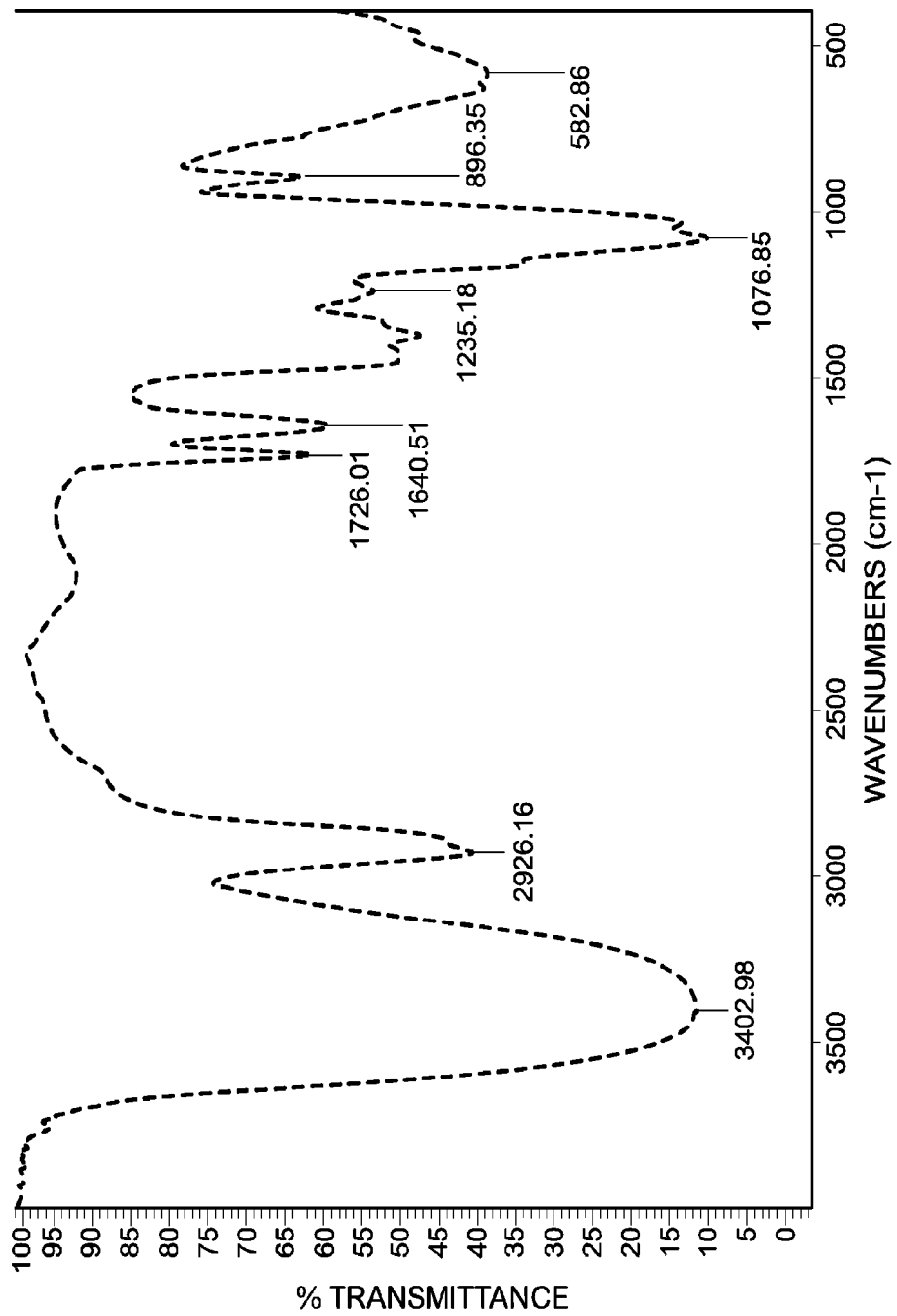
FIG. 5. shows the FTIR spectrum of Reb X.

As used herein, the term "steviol glycoside(s)" refers to glycosides of steviol, including, but not limited to, naturally occurring steviol glycosides, e.g. Rebaudioside A, Rebaudioside B, Rebaudioside C, Rebaudioside D, Rebaudioside E, Rebaudioside F, Rebaudioside X, Stevioside, Steviolbioside, Dulcoside A, Rubusoside, etc. or synthetic steviol glycosides, e.g. enzymatically glucosylated steviol glycosides and combinations thereof.

As used herein, the term "total steviol glycosides" (TSG) is calculated as the sum of the content of all steviol glycosides on a dry (anhydrous) basis, including, for example, Rebaudioside A (Reb A), Rebaudioside B (Reb B), Rebaudioside C (Reb C), Rebaudioside D (Reb D), Rebaudioside E (Reb E), Rebaudioside F (Reb F), Rebaudioside X (Reb X), Stevioside, Steviolbioside, Dulcoside A and Rubusoside.

As used herein, the term "Reb X/TSG ratio" is calculated as the ratio of Reb X and TSG content on a dry basis as per the formula below:

$$\{\text{Reb X content}(\%\text{ dry basis})/\text{TSG content}(\%\text{ dry basis})\}\times 100\%$$

As used herein, the term "solution of steviol glycosides" refers to any solution containing a solvent and steviol glycosides. One example of a solution of steviol glycosides is the resin-treated filtrate obtained from purification of *Stevia rebaudiana* plant material (e.g. leaves), described below, or by-products of other steviol glycosides' isolation and purification processes. Another example of a solution of steviol glycosides is a commercially available *stevia* extract brought into solution with a solvent. Yet another example of a solution of steviol glycosides is a commercially available mixture of steviol glycosides brought into solution with a solvent.

In another aspect of the invention, a method for purifying Reb X comprises:
  (a) passing a solution of steviol glycosides through a multi-column system including a plurality of columns packed with an adsorbent resin to provide at least one column having adsorbed steviol glycosides; and
  (b) eluting fractions with high Reb X content from the at least one column having adsorbed steviol glycosides to provide an eluted solution with high Reb X content.

In another aspect of the invention, a method for purifying Reb X comprises:
  (a) passing a solution of steviol glycosides through a multi-column system including a plurality of columns packed with an adsorbent resin to provide at least one column having adsorbed steviol glycosides;
  (b) removing impurities from the multi-column system; and
  (c) eluting fractions with high Reb X content from the at least one column having adsorbed steviol glycosides to provide an eluted solution with high Reb X content.

In another embodiment, a method for purifying Reb X comprises:
  (a) passing a solution of steviol glycosides through a multi-column system including a plurality of columns packed with an adsorbent resin to provide at least one column having adsorbed steviol glycosides;
  (b) eluting fractions with high Reb X content from the at least one column having adsorbed steviol glycosides to provide an eluted solution with high Reb X content;
  (c) decolorizing the eluted solution with high Reb X content to provide a first adsorption solution; and
  (d) removing the alcoholic solvent from the first adsorption solution and passing the remaining solution through a column with a macroporous adsorbent to provide a second adsorption solution.

In another embodiment, a method for purifying Reb X comprises:
  (a) passing a solution of steviol glycosides through a multi-column system including a plurality of columns packed with an adsorbent resin to provide at least one column having adsorbed steviol glycosides;
  (b) removing impurities from the multi-column system;
  (c) eluting fractions with high Reb X content from the at least one column having adsorbed steviol glycosides to provide an eluted solution with high Reb X content;
  (d) decolorizing the eluted solution with high Reb X content to provide a first adsorption solution; and
  (e) removing the alcoholic solvent from the first adsorption solution and passing the remaining solution through a column with a macroporous adsorbent to provide a second adsorption solution.

In another embodiment, a method for purifying Reb X comprises:
  (a) passing a solution of steviol glycosides through a multi-column system including a plurality of columns packed with an adsorbent resin, to provide at least one column having adsorbed steviol glycosides;
  (b) eluting fractions with high Reb X content from the at least one column having adsorbed steviol glycosides to provide an eluted solution with high Reb X content; and
  (c) deionizing the solution.

In another embodiment, a method for purifying Reb X comprises:
  (a) passing a solution of steviol glycosides through a multi-column system including a plurality of columns packed with an adsorbent resin to provide at least one column having adsorbed steviol glycosides;
  (b) removing impurities from the multi-column system;
  (c) eluting fractions with high Reb X content from the at least one column having adsorbed steviol glycosides to provide an eluted solution with high Reb X content; and
  (c) deionizing the solution.

In another embodiment, a method for purifying Reb X comprises:
  (a) passing a solution of steviol glycosides through a multi-column system including a plurality of columns packed with an adsorbent resin to provide at least one column having adsorbed steviol glycosides;
  (b) eluting fractions with high Reb X content from the at least one column having adsorbed steviol glycosides to provide an eluted solution with high Reb X content;
  (c) decolorizing the eluted solution with high Reb X content to provide a first adsorption solution;
  (d) removing the alcoholic solvent from the first adsorption solution and passing the remaining solution through a column with a macroporous adsorbent to provide a second adsorption solution; and
  (e) deionizing the second adsorption solution.

In another embodiment, a method for purifying Reb X comprises:
  (a) passing a solution of steviol glycosides through a multi-column system including a plurality of columns packed with an adsorbent resin to provide at least one column having adsorbed steviol glycosides;
  (b) removing impurities from the multi-column system;
  (c) eluting fractions with high Reb X content from the at least one column having adsorbed steviol glycosides to provide an eluted solution with high Reb X content;
  (d) decolorizing the eluted solution with high Reb X content to provide a first adsorption solution;
  (e) removing the alcoholic solvent from the first adsorption solution and passing the remaining solution through a column with a macroporous adsorbent to provide a second adsorption solution; and
  (f) deionizing the second adsorption solution.

Removal of the alcoholic solvent from any of the above-mentioned processes relating to Reb X purification provides a high Reb X content mixture. Subsequent removal of aqueous solvent provides a high Reb X content mixture containing from about 30% to about 40% solids content, as discussed in the "Concentration" section below. Alternatively, substantially all of the solvent can removed to provide a dry powder with high Reb X content.

In one embodiment, a method for purifying Reb X comprises:
(a) passing a solution of steviol glycosides through a multi-column system including a plurality of columns packed with an adsorbent resin to provide at least one column having adsorbed steviol glycosides;
(b) removing impurities from the multi-column system;
(c) eluting fractions with high Reb X content from the at least one column having adsorbed steviol glycosides to provide an eluted solution with high Reb X content;
(d) decolorizing the eluted solution with high Reb X content to provide a first adsorption solution;
(e) removing the alcoholic solvent from the first adsorption solution and passing the remaining solution through a column with a macroporous adsorbent to provide a second adsorption solution;
(f) deionizing the second adsorption solution; and
(g) removing the alcoholic solvent to provide a high Reb X content mixture.

Further removal of aqueous solvents provides a high Reb X content mixture containing from about 30% to about 40% solids content, as discussed in the "Concentration" section. Alternatively, substantially all of the solvent can removed to provide a dry powder with high Reb X content.

In one embodiment, a method for purifying steviol glycosides includes:
(a) passing a solution of steviol glycosides through a multi-column system including a plurality of columns packed with an adsorbent resin to provide at least one column having adsorbed steviol glycosides; and
(b) eluting fractions with low Reb X content from the at least one column having adsorbed steviol glycosides to provide an eluted solution of steviol glycosides.

In a more specific embodiment, a method for purifying steviol glycosides includes:
(a) passing a solution of steviol glycosides through a multi-column system including a plurality of columns packed with an adsorbent resin to provide at least one column having adsorbed steviol glycosides;
(b) removing impurities from the multi-column system; and
(c) eluting fractions with low Reb X content from the at least one column having adsorbed steviol glycosides to provide an eluted solution of steviol glycosides.

In another embodiment, a method for purifying steviol glycosides includes:
(a) passing a solution of steviol glycosides through a multi-column system including a plurality of columns packed with an adsorbent resin to provide at least one column having adsorbed steviol glycosides;
(b) eluting fractions with low Reb X content from the at least one column having adsorbed steviol glycosides to provide an eluted solution of steviol glycosides;
(c) decolorizing the eluted solution to provide a first adsorption solution; and
(d) removing the alcoholic solvent from the first adsorption solution and passing the remaining solution through a column with a macroporous adsorbent to provide a second adsorption solution.

In a more specific embodiment, a method for purifying steviol glycosides includes:
(a) passing a solution of steviol glycosides through a multi-column system including a plurality of columns packed with an adsorbent resin to provide at least one column having adsorbed steviol glycosides;
(b) removing impurities from the multi-column system;
(c) eluting fractions with low Reb X content from the at least one column having adsorbed steviol glycosides to provide an eluted solution of steviol glycosides;
(d) decolorizing the eluted solution to provide a first adsorption solution; and
(e) removing the alcoholic solvent from the first adsorption solution and passing the remaining solution through a column with a macroporous adsorbent to provide a second adsorption solution.

In still another embodiment, a method for purifying steviol glycosides includes:
(a) passing a solution of steviol glycosides through a multi-column system including a plurality of columns packed with an adsorbent resin to provide at least one column having adsorbed steviol glycosides;
(b) eluting fractions with low Reb X content from the at least one column having adsorbed steviol glycosides to provide an eluted solution of steviol glycosides; and
(c) deionizing the solution.

In a more specific embodiment, a method for purifying steviol glycosides includes:
(a) passing a solution of steviol glycosides through a multi-column system including a plurality of columns packed with an adsorbent resin to provide at least one column having adsorbed steviol glycosides;
(b) removing impurities from the multi-column system;
(c) eluting fractions with low Reb X content from the at least one column having adsorbed steviol glycosides to provide an eluted solution of steviol glycosides; and
(d) deionizing the solution.

In yet another embodiment, a method for purifying steviol glycosides includes:
(a) passing a solution of steviol glycosides through a multi-column system including a plurality of columns packed with an adsorbent resin to provide at least one column having adsorbed steviol glycosides;
(b) eluting fractions with low Reb X content from the at least one column having adsorbed steviol glycosides to provide an eluted solution of steviol glycosides;
(c) decolorizing the eluted solution to provide a first adsorption solution;
(d) removing the alcoholic solvent from the first adsorption solution and passing the remaining solution through a column with a macroporous adsorbent to provide a second adsorption solution; and
(e) deionizing the second adsorption solution.

In a more specific embodiment, a method for purifying steviol glycosides includes:
(a) passing a solution of steviol glycosides through a multi-column system including a plurality of columns packed with an adsorbent resin to provide at least one column having adsorbed steviol glycosides;
(b) removing impurities from the multi-column system;
(c) eluting fractions with low Reb X content from the at least one column having adsorbed steviol glycosides to provide an eluted solution of steviol glycosides;
(d) decolorizing the eluted solution to provide a first adsorption solution;
(e) removing the alcoholic solvent from the first adsorption solution and passing the remaining solution through a column with a macroporous adsorbent to provide a second adsorption solution; and
(f) deionizing the second adsorption solution.

The eluted solution of steviol glycosides (decolorized and/or deionized) can be partially or fully dried, i.e. the solvent can be partially or completely removed to provide a semi- or entirely dry powder, as provided below in the "Concentration" section. In one embodiment, complete removal of the solvent provides a purified mixture of steviol glycosides with total steviol glycoside content greater than about 95% on a dry basis.

In yet another embodiment, a method for purifying steviol glycosides includes:

(a) passing a solution of steviol glycosides through a multi-column system including a plurality of columns packed with an adsorbent resin to provide at least one column having adsorbed steviol glycosides;
(b) removing impurities from the multi-column system;
(c) eluting fractions with low Reb X content from the at least one column having adsorbed steviol glycosides to provide an eluted solution of steviol glycosides;
(d) decolorizing the eluted solution to provide a first adsorption solution;
(e) removing the alcoholic solvent from the first adsorption solution and passing the remaining solution through a column with a macroporous adsorbent to provide a second adsorption solution;
(f) deionizing the second adsorption solution; and
(g) removing the solvent from the solution to provide a purified steviol glycoside mixture with at least about 95% by weight total steviol glycosides.

Preparing the Solution of Steviol Glycosides

Although the process for obtaining Reb X from *Stevia rebaudiana* leaves is provided herein, those of skill in the art will recognize that the techniques described hereafter also apply to other starting materials containing Reb X, including, but not limited to, commercially available *stevia* extracts, commercially available steviol glycoside mixtures, by-products of other steviol glycosides' isolation and purification processes of the same.

Those of skill in the art will also recognize that certain steps described below, such as "separating insoluble material", "removal of high molecular weight compounds and insoluble particles" and "removing salts" may be omitted when the starting materials do not contain insoluble material and/or high molecular weight compounds and/or salts. For example, in cases when already purified starting materials are used, such as commercially available *stevia* extracts, commercially available steviol glycoside mixtures, by-products of other steviol glycosides' isolation and purification processes of the same, one or more of the aforementioned steps may be omitted.

Those experienced in art will also understand that although the process described below assumes certain order of the described steps this order can be altered in some cases.

The process of the present invention provides for complete retreatment of *Stevia rebaudiana* Bertoni plant extract, with isolation and purification of a highly purified steviol glycoside mixture or highly purified individual sweet glycosides, such as Rebaudioside X. The plant extract can be obtained using any method such as, but not limited to, the extraction methods described in U.S. Pat. No. 7,862,845, the entire contents of which are incorporated by reference herein, as well as membrane filtration, supercritical fluid extraction, enzyme-assisted extraction, microorganism-assisted extraction, ultrasound-assisted extraction, microwave-assisted extraction, etc.

The solution of steviol glycosides may be prepared from *Stevia rebaudiana* Bertoni leaves by contacting the *Stevia rebaudiana* Bertoni plant material with solvent to produce a crude extract, separating insoluble material from the crude extract to provide a first filtrate containing steviol glycosides, treating the first filtrate to remove high molecular weight compounds and insoluble particles, thereby providing a second filtrate containing steviol glycosides and treating the second filtrate with an ion-exchange resin to remove salts to provide a resin-treated filtrate.

In one embodiment, the *Stevia rebaudiana* plant material (e.g. leaves) may be dried at temperatures between about 20° C. to about 60° C. until a moisture content between about 5% and about 8% is reached. In a particular embodiment, the plant material may be dried between about 20° C. and about 60° C. for a period of time from about 1 to about 24 hours, such as, for example, between about 1 to about 12 hours, between about 1 to about 8 hours, between about 1 to about 5 hours or between about 2 hours to about 3 hours. In other particular embodiments, the plant material may be dried at temperatures between about 40° C. to about 45° C. to prevent decomposition.

In some embodiments, the dried plant material is optionally milled. Particle sizes may be between about 10 to about 20 mm.

The amount of Reb X in the plant material of the *Stevia rebaudiana* Bertoni can vary. Generally speaking, Reb X should be present in an amount of at least about 0.001% by weight on an anhydrous basis.

The plant material (milled or unmilled) may be extracted by any suitable extraction process, such as, for example, continuous or batch reflux extraction, supercritical fluid extraction, enzyme-assisted extraction, microorganism-assisted extraction, ultrasound-assisted extraction, microwave-assisted extraction, etc. The solvent used for the extraction can be any suitable solvent, such as for example, polar organic solvents (degassed, vacuumed, pressurized or distilled), non-polar organic solvents, water (degassed, vacuumed, pressurized, deionized, distilled, carbon-treated or reverse osmosis) or a mixture thereof. In a particular embodiment, the solvent comprises water and one or more alcohols. In another embodiment, the solvent is water. In another embodiment, the solvent is one or more alcohols.

In a particular embodiment, the plant material is extracted with water in a continuous reflux extractor. One of skill in the art will recognize the ratio of extraction solvent to plant material will vary based on the identity of the solvent and the amount of plant material to be extracted. Generally, the ratio of extraction solvent to kilogram of dry plant material is from about 20 liters to about 25 liters to about one kilogram of leaves.

The pH of the extraction solvent can be between about pH 2.0 and 7.0, such as, for example, between about pH 2.0 and about pH 5.0, between about pH 2.0 and about pH 4.0 or between about pH 2.0 and about pH 3.0. In a particular embodiment, the extraction solvent is aqueous, e.g. water and, optionally, acid and/or base in an amount to provide a pH between about pH 2.0 and 7.0, such as, for example, between about pH 2.0 and about pH 5.0, between about pH 2.0 and about pH 4.0 or between about pH 2.0 and about pH 3.0. Any suitable acid or base can be used to provide the desired pH for the extraction solvent, such as, for example, HCl, NaOH, citric acid, and the like.

The extraction may be carried out at temperatures between about 25° C. and about 90° C., such as, for example, between about 30° C. and about 80° C., between about 35° C. and about 75° C., between about 40° C. and about 70° C., between about 45° C. and about 65° C. or between about 50° C. and about 60° C.

In embodiments where the extraction process is a batch extraction process, the duration of extraction may range from about 0.5 hours to about 24 hours, such as, for example, from about 1 hour to about 12 hours, from about 1 hour to about 8 hours, or from about 1 hour to about 6 hours.

In embodiments where the extraction process is a continuous process, the duration of extraction may range from about 1 hour to about 5 hours, such as, for example, from about 2.5 hours to about 3 hours.

After extraction, the insoluble plant material may be separated from the solution by filtration to provide a filtrate containing steviol glycosides, referred to herein as a "first filtrate containing steviol glycosides". Separation can be achieved by any suitable means including, but not limited to, gravity filtration, a plate-and-frame filter press, cross flow filters, screen filters, Nutsche filters, belt filters, ceramic filters, membrane filters, microfilters, nanofilters, ultrafilters or centrifugation. Optionally various filtration aids such as diatomaceous earth, bentonite, zeolite etc, may also be used in this process.

After separation, the pH of the first filtrate containing steviol glycosides may be adjusted to remove additional impurities. In one embodiment, the pH of the first filtrate containing steviol glycosides can be adjusted to between about 8.5 and about 10.0 by treatment with a base, such as, for example, calcium oxide or hydroxide (about 1.0% from the volume of filtrate) with slow agitation.

Treatment of the first filtrate with the base, as set forth above, results in a suspension, the pH of which can be adjusted to about 3.0 to about 4.0 by treatment with any suitable flocculation/coagulation agent. Suitable flocculation/coagulation agents include, for example, potassium alum, aluminum sulfate, aluminum hydroxide, aluminum oxide, $CO_2$, $H_3PO_4$, $P_2O_5$, MgO, $SO_2$, anionic polyacrylamides, quaternary ammonium compounds with long-chain fatty acid substitutents, bentonite, diatomaceous earth, KemTab Sep series, Superfloc series, KemTab Flote series, Kemtalo MeI series, Midland PCS-3000, Magnafloc LT-26, Zuclar 100, Prastal 2935, Talofloc, Magox, soluble ferrous salts or a combination thereof. Exemplary ferrous salts include, but are not limited to, $FeSO_4$, $FeCl_2$, $Fe(NO_3)_3$, $Fe(SO_4)_3$, $FeCl_3$ and combinations thereof. In a particular embodiment, the ferrous salt is $FeCl_3$. The filtrate may be treated with the flocculation/coagulation agent for a duration of time between about 5 minutes to about 1 hour, such as, for example, from about 5 minutes to about 30 minutes, from about 10 minutes to about 20 minutes or from about 10 minutes to about 15 minutes. Stirred or slow agitation can also be used to facilitate treatment. Optionally, the pH of resultant mixture may then be adjusted to between about 8.5 and about 9.0 with a base, such as, for example, calcium oxide or sodium hydroxide. The duration of time for treatment with base, and optionally, with agitation, is between about 5 minutes to about 1 hour, such as, for example, from about 10 minutes to about 50 minutes, from about 15 minutes to about 45 minutes, from about 20 minutes to about 40 minutes or from about 25 minutes to about 35 minutes. In a particular embodiment, the base is calcium oxide used for a between about 15 and about 40 minutes with slow agitation.

Precipitated high molecular weight compounds and insoluble particles are separated from the mixture to provide second filtrate containing steviol glycosides. Separation can be achieved by any suitable means including, but not limited to, gravity filtration, a plate-and-frame filter press, cross flow filters, screen filters, Nutsche filters, belt filters, ceramic filters, membrane filters, microfilters, nanofilters, ultrafilters or centrifugation. Optionally various filtration aids such as diatomaceous earth, bentonite, zeolite etc, may be used in this process.

The second filtrate containing steviol glycosides may then be subjected to preliminary deionization by any suitable method including, for example, electrodialysis, filtration (nano- or ultra-filtration), reverse osmosis, ion exchange, mixed bed ion exchange or a combination of such methods. In one embodiment, the second filtrate containing steviol glycosides is deionized by treatment with one or more ion exchange resins to provide a resin-treated filtrate. In one embodiment, the second filtrate containing steviol glycosides is passed through a strong acid cation exchange resin. In another embodiment, the second filtrate containing steviol glycosides is passed through a weak base anion-exchange resin. In still another embodiment, the second filtrate containing steviol glycosides is passed through a strong acid cation-exchange resin followed by a weak base anion-exchange resin. In yet another embodiment, the second filtrate containing steviol glycosides is passed through a weak base anion-exchange resin followed by a strong acid cation-exchange resin.

The cation-exchange resin can be any strong acid cation-exchanger where the functional group is, for example, sulfonic acid. Suitable strong acid cation-exchange resins are known in the art and include, but are not limited to, Rohm & Haas Amberlite® 10 FPC22H resin, which is a sulfonated divinyl benzene styrene copolymer, Dowex® ion exchange resins available from Dow Chemical Company, Serdolit® ion exchange resins available from Serva Electrophoresis GmbH, T42 strong acidic cation exchange resin and A23 strong base an ion exchange resin available from Qualichem, Inc., and Lewatit strong ion exchange resins available from Lanxess. In a particular embodiment, the strong acid cation-exchange resin is Amberlite® 10 FPC22H resin ($H^+$). As would be known to those skilled in the art, other suitable strong acid cation-exchange resins for use with embodiments of this invention are commercially available.

The anion-exchange resin can be any weak base anion-exchanger where the functional group is, for example, a tertiary amine. Suitable weak base anion exchange resins are known in the art and include, but are not limited to, resins such as Amberlite-FPA53 ($OH^-$), Amberlite IRA-67, Amberlite IRA-95, Dowex 67, Dowex 77 and Diaion WA 30 may be used. In a particular embodiment, the strong acid cation-exchange resin is Amberlite-FPA53 ($OH^-$) resin. As would be known to those skilled in the art, other suitable weak base anion-exchange resins for use with embodiments of this invention are commercially available.

In a particular embodiment, the second filtrate containing steviol glycosides is passed through a strong acid cation-exchange resin, e.g. Amberlite® 10 FPC22H resin ($H^+$), followed by a weak base anion-exchange resin, e.g. Amberlite-FPA53 ($OH^-$), to provide a resin-treated filtrate. The specific velocity (SV) through one or more of the ion exchange columns can be between about 0.01 to about 5 $hour^{-1}$, such as, for example between about 0.05 to about 4 $hour^{-1}$, between about 1 and about 3 $hour^{-1}$ or between about 2 and about 3 $hour^{-1}$. In a particular embodiment, the specific velocity through the one or more ion exchange columns is about 0.8 $hour^{-1}$. Following completion of passing the second filtrate containing steviol glycosides through one or more ion exchange columns, the one or more ion exchange columns are washed with water, preferably reverse osmosis (RO) water. The solution obtained from the water wash and the resin-treated filtrate may be combined before proceeding to the multi-column step.

Adsorption of the Solution of Steviol Glycosides

In certain embodiment, the solution of steviol glycosides is the resin-treated filtrate obtained from purification of *Stevia rebaudiana* leaf, described above. In another embodiment, the solution of steviol glycosides is a commercially available *stevia* extract dissolved in a solvent. In yet another embodiment, the solution of steviol glycosides is a commercially available extract where insoluble material and/or high molecular weight compounds and/or salts have been removed.

Reb X content in the solution of steviol glycosides may vary depending on the source of the solution of steviol glycosides. For example, in embodiments where the source of steviol glycosides is plant material, the concentration of Reb X can be between about 5 ppm to about 50,000 ppm, such as, for example, from about 10,000 ppm to about 50,000 ppm. In a particular embodiment, the concentration of Reb X in the solution of steviol glycosides, where the source of steviol glycosides is plant material, is from about 5 ppm to about 50 ppm.

In embodiments where the source is non-plant material, the concentration of Reb X in the solution of steviol glycosides can also vary. In exemplary embodiments, the concentration of Reb X in the solution of steviol glycosides can be between about 5 ppm to about 50,000 ppm, such as, for example, from about 5,000 ppm to about 10,000 ppm.

The Reb X/TSG ratio in the solution of steviol glycosides will also vary depending on the source of the steviol glycosides. In one embodiment, the Reb X/TSG in the solution of steviol glycosides is from about 0.5% to about 99%, such as, for example, from about 0.5% to about 10%, from about 0.5% to about 20%, from about 0.5% to about 30%, from about 0.5% to about 40%, from about 0.5% to about 50%, from about 0.5% to about 60%, from about 0.5% to about 70%, from about 0.5% to about 80%, from about 0.5% to about 90%. In more particular embodiments, the Reb X/TSG in the solution of steviol glycosides is from about 0.5% to about 5%.

The solution of steviol glycosides may be passed through one or more consecutively connected columns (connected serially or in parallel) packed with polar macroporous polymeric adsorbent to provide at least one column having adsorbed steviol glycosides. In some embodiments, the number of columns can be greater than 3, such as, for example, 5 columns, 6 columns, 7 columns, 8 columns, 9 columns, 10 columns, 11 column, 12 columns, 13 columns, 14 columns or 15 columns. In a particular embodiment, the resin-treated filtrate is passed through 7 columns.

In certain embodiments, the first column in the sequence can be a "catcher column", which is used to adsorb certain impurities, such as sterebins, that have higher adsorption rates and faster desorption rates than most steviol glycosides. In some embodiments, the "catcher column" size can be about one-third the size of the remaining columns. The ratio of internal diameter to column height or so-called "diameter:height ratio" of the columns shall be between about 1:1 to about 1:100, such as, for example, about 1:2, about 1:6, about 1:10, about 1:13, about 1:16, or about 1:20. In a particular embodiment, the diameter:height ratio of the column is about 1:3. In yet another embodiment, the diameter:height ratio is about 1:8. In still another embodiment, the diameter:height ratio is about 1:15.

The polar macroporous polymeric adsorbent may be any macroporous polymeric adsorption resins capable of adsorbing steviol glycosides, such as, for example, the Amberlite® XAD series (Rohm and Haas), Diaion® HP series (Mitsubishi Chemical Corp), Sepabeads® SP series (Mitsubishi Chemical Corp), Cangzhou Yuanwei YWD series (Cangzhou Yuanwei Chemical Co. Ltd., China), or the equivalent. The individual columns may be packed with the same resin or with different resins. The columns may be packed with sorbent up to from about 75% to about 100% of their total volume.

In embodiments wherein the multi-column system is connected in parallel, the inlet of each column may connect to a separate feed source while the outlet of each column connects to a separate receiver. The ratio of the volume of the first column to the volume of the second column is preferably in the range of about 1:1 to 1:10. The ratio of the volume of the last column to the volume of the previous, or penultimate, column is preferably in the range of about 3:1 to 1:10. The columns may be maintained at a temperature in the range of about 5-80° C., and preferably in the range of about 15-25° C.

The solvent that carries the steviol glycoside solution through the column system can comprise alcohol, water, or a combination thereof (an aqueous alcoholic solvent). The water to alcohol ratio (vol/vol) in the aqueous alcoholic solvent may be in the range of about 99.9:0.1 to about 60:40, such as, for example, about 99:1 to about 90:10. The specific velocity (SV) can be from about $0.3^{-1}$ to about $1.5^{-1}$, such as, for example, about 1.0 hour$^{-1}$.

The alcohol can be selected from, for example, methanol, ethanol, n-propanol, 2-propanol, 1-butanol, 2-butanol and mixtures thereof.

Impurities and different steviol glycosides are retained in different sections of the column system. Impurities with higher affinities to the sorbent are retained in the first column, impurities with lower affinities to the sorbent are retained in the last column, and different steviol glycosides are retained in different sections of the system at different concentrations, depending on their affinities to the sorbent. Generally Reb X is retained in later columns. "Columns" is used interchangeably herein with "fractions", both of which refer to columns, or sections of columns with the desirable content (e.g. Reb X). As a result, the initial mixture of steviol glycosides separates into different portions retained on different columns. The portions differ from each other both by total steviol glycoside content and individual glycoside (particularly Reb X) content.

Removing Impurities from the Multi-Column System

Upon complete passage through the one or more columns, the resins can optionally be washed with a washing solution to remove impurities from the one or more columns. Suitable washing solutions include an aqueous or alcoholic solution, where the aqueous solution can contain any suitable acid or base to arrive at the desired pH. The water to alcohol ratio (vol/vol) in the aqueous alcoholic solution is in the range of about 99.9:0.1 to about 60:40. Multiple washes of the columns with the same, or different, wash solutions can be performed, followed by wash(es) with water until the pH of the effluent from the one or more columns is about neutral (i.e., has a pH from about 6.0 to about 7.0). In a particular embodiment, the resins of the one or more columns is washed sequentially with one volume of water, two volumes of NaOH, one volume of water, two volumes of HCl, and finally with two volumes of water until it reached a neutral pH. The elution of impurities is carried out either from each column separately (parallel connection) or from two or more consecutively (serially) connected columns.

Eluting the Adsorbed Steviol Glycosides

Desorption can be carried out with an aqueous alcohol solution. Suitable alcohols include methanol, ethanol, n-propanol, 2-propanol, 1-butanol, 2-butanol and mixtures thereof. In a particular embodiment, the aqueous alcoholic solution can contain between about 30% to about 70% alcohol content, such as, for example, between about 40% to about 60%, about 50% to about 60%, about 51%, about 52%, about 53%, about 54%, about 55%, about 56%, about 57%, about 58% or about 59%. In a particular embodiment, the aqueous alcoholic solution contains between about 50% to about 52% ethanol. A SV between about 0.5 hour$^{-1}$ to about 3.0 hour$^{-1}$, such as, for example, between about 1.0 hour$^{-1}$ and about 1.5 hour$^{-1}$ can be used. Desorption of the first "catcher column", which is optional, can be carried out separately from the non-"catcher column" columns.

In one embodiment, fractions with high Reb X content are eluted with an aqueous alcohol solution to provide an eluted solution with high Reb X content. "High Reb X content", as used herein, refers to any material which has a higher Reb X/TSG ratio compared to the solution of steviol glycosides prior to passing through the multi-column system. In one embodiment, the Reb X/TSG ratio is greater than about 1% higher than the Reb X/TSG ratio of the solution of steviol glycosides. In another embodiment, the Reb X/TSG ratio is greater than about 2% higher, about 3% higher, about 4% higher, about 5% higher, about 10% higher, about 15% higher, about 20% higher, about 25% higher, about 30% higher, about 35% higher, about 40% higher, about 45% higher, about 50% higher, about 55% higher, about 60% higher about 65% higher about 70% higher, about 75% higher, about 80% higher, about 85% higher, about 90% higher or about 95% higher. Generally speaking, the later columns will contain "high Reb X content" fractions.

In a particular embodiment, the remaining columns (excluding the "catcher column") can also be eluted with an aqueous alcohol solution and their eluates combined to provide an eluted solution of steviol glycosides with low Reb X content. "Low Reb X content", as used herein, refers to any material which has a lower Reb X/TSG ratio compared to the solution of steviol glycosides prior to passing through the multi-column system. "Low Reb X content" also refers to any material which has zero Reb X content. Generally speaking, the initial columns will contain "low Reb X content".

The Reb X/TSG ratio can be determined experimentally by HPLC or HPLC/MS. For example, chromatographic analysis can be performed on a HPLC/MS system comprising an Agilent 1200 series (USA) liquid chromatograph equipped with binary pump, autosampler, thermostatted column compartment, UV detector (210 nm), and Agilent 6110 quadrupole MS detector interfaced with Chemstation data acquisition software. The column can be a "Phenomenex Prodigy 5u ODS3 250×4.6 mm; 5 µm (P/No. 00G-4097-E0)" column maintained at 40° C. The mobile phase can be 30:70 (vol/vol.) acetonitrile and water (containing 0.1% formic acid) and the flow rate through the column can be 0.5 mL/min. The steviol glycosides can be identified by their retention times in such a method, which are generally around 2.5 minutes for Reb D, around 2.9 minutes for Reb X, 5.5 minutes for Reb A, 5.8 minutes for Stevioside, 7.1 minutes for Reb F, 7.8 minutes for Reb C, 8.5 minutes for Dulcoside A, 11.0 minutes for Rubusoside, 15.4 minutes for Reb B and 16.4 minutes for Steviolbioside. One of skill in the art will appreciate that the retention times for the various steviol glycosides given above can vary with changes in solvent and/or equipment.

Those of skill in the art will also recognize that one or more of the "decolorizing", "second adsorption" and "deionization" steps, described below, may be omitted, e.g. where generally higher purity starting material solutions of steviol glycosides are used. Those experienced in art will also understand that although the process described below assumes certain order of the described steps, this order can be altered in some cases.

Decolorizing

Decolorization can be achieved with any known method, such as, for example, treatment with activated carbon. The quantity of the activated carbon can be from about 0.1% (wt/vol) to about 0.8% (wt/vol). In a particular embodiment, the quantity of activated carbon is from about 0.25% (wt/vol) to about 0.30% (wt/vol). The suspension may be continuously agitated. The temperature of the treatment can be between about 20° C. and about 30° C., such as, for example, about 25° C. The treatment can be for any duration sufficient to decolorize the eluted solution, such as, for example, between about 20 minutes and about 3 hours, between 20 minutes and about 2 hours, between about 30 minutes and 1.5 hours or between about 1 hour and about 1.5 hours. Following treatment, separation of used carbon can be conducted by any known separation means, such as, for example, gravity or suction filtration, centrifugation or plate-and-frame press filter.

The eluted solution with high Reb X content can optionally be decolorized separately from the eluted solution of steviol glycosides with low Reb X content.

Second Adsorption

The decolorized solution (also referred to herein as "the first adsorption solution") can be distilled or evaporated with vacuum to remove alcoholic solvent and then passed through macroporous adsorbent second time to provide a second adsorption solution. The second adsorption solution contains aqueous solvent.

Deionization

Generally any type of strong acid cation-exchanger and weak anion-exchangers can be used at this stage. In one embodiment, the eluted solution (e.g. the eluted solution with high Reb X content—optionally decolorized or the eluted solution of steviol glycosides—optionally decolorized) can be passed through a strong acid cation exchange resin. In another embodiment, the eluted solution is passed through a weak base anion-exchange resin. In still another embodiment, the eluted solution is passed through a strong acid cation-exchange resin followed by a weak base anion-exchange resin. In yet another embodiment, the eluted solution is passed through a weak base anion-exchange resin followed by a strong acid cation-exchange resin. Suitable strong acid cation-exchange columns, weak base anion-exchange columns and flow rates are provided above with respect to production of the resin-treated filtrate. In a particular embodiment, the eluted solution can be passed through columns packed with cation-exchange resin Amberlite FPC22H(H$^+$) followed with anion-exchange resin Amberlite FPA53 (OH$^-$).

In one embodiment, the second adsorption solution can be passed through a strong acid cation exchange resin. In another embodiment, the second adsorption solution is passed through a weak base anion-exchange resin. In still another embodiment, the second adsorption solution is passed through a strong acid cation-exchange resin followed by a weak base anion-exchange resin. In yet another embodiment, the second adsorption solution is passed through a weak base anion-exchange resin followed by a strong acid cation-exchange resin. Suitable strong acid cation-exchange columns, weak base anion-exchange columns and flow rates are provided above with respect to production of the resin-treated filtrate. In a particular embodiment, the second adsorption solution can be passed through columns packed with cation-exchange resin Amberlite FPC22H(H$^+$) followed with anion-exchange resin Amberlite FPA53 (OH$^-$).

Those experienced in art will recognize that deionization may be alternatively conducted by means of mixed bed ion exchange, electrodialysis or various membranes such as, for example, reverse osmosis membranes, nanofiltration membranes or ultrafiltration membranes.

Concentration

The eluted solution (e.g. the eluted solution with high Reb X content—optionally decolorized and/or deionized, the eluted solution of steviol glycosides—optionally decolorized and/or deionized) or the second adsorption solution (optionally deionized) can be distilled or evaporated with vacuum to remove alcoholic solvent.

Once the alcoholic solvent is removed, the remaining aqueous solvent from the concentrate of steviol glycosides, or concentrated second adsorption solution, can be removed by any suitable means, including, but not limited to, evaporation or vacuum, to provide a dry purified steviol glycoside mixture with greater than 95% by weight total steviol glycosides on a dry basis.

Removal of alcoholic solvents from the eluted solution with high Reb X content provides a high Reb X content mixture. Further concentration to remove aqueous solvent can then be carried out by any suitable method, such as, for example, nano-filtration or evaporation under reduced pressure conditions to provide a high Reb X content mixture containing from about 30% to about 40% solids content, such as, for example, from about 30% to about 35% solids content or from about 33% to about 35% solids content. The high Reb X content mixture containing from about 30% to about 40% solids content contains aqueous solvent.

Alternatively, all solvent from the eluted solution with high Reb X content can be removed by any suitable method, such as, for example, nano-filtration or evaporation under reduced pressure, freeze drying, flash drying, spray drying or a combination thereof to provide a dry powder with high Reb X content.

Purification of Reb X

In one embodiment, purification of Reb X from a high Reb X content mixture containing from about 30% to about 40% solids content can be achieved by mixing a high Reb X content mixture containing from about 30% to about 40% solids content with a first alcoholic solvent to provide a Reb X solution and inducing crystallization. Generally, the ratio of solvent to solids is from about 0.5 liters to about 100 liters per one kilogram of solid. In particular embodiments, the ratio of solvent to solids can be from about 3 to about 10 liters of solvent per one kilogram of solid. The alcohol can be any suitable alcohol, such as, for example, methanol, ethanol, n-propanol, 2-propanol, 1-butanol, 2-butanol and mixtures thereof. The alcohol can contain small amounts of water or be anhydrous. In a particular embodiment, the alcohol is anhydrous methanol.

In another embodiment, purification of a high Reb X content mixture containing more than about 40% solids content can be achieved by diluting the mixture with water to provide a high Reb X content mixture containing from about 30% to about 40% solids content, mixing the mixture with an alcoholic solvent to provide a Reb X solution and inducing crystallization.

In yet another embodiment, a dry powder with high Reb X content can be mixed with an aqueous alcoholic solvent to provide a Reb X solution (preferably containing from about 30% to about 40% solids content) and inducing crystallization.

To induce crystallization, the Reb X solution is maintained at a temperature between about 20° C. and about 25° C., such as, for example, between about 20° C. and about 22° C., and, if necessary, seeded with Reb X crystals. The duration of mixing can be between about 1 hour and about 48 hours, such as, for example, about 24 hours.

Reb X crystals having a purity greater than about 60% by weight on a dry basis (referred to herein as the "first crystals of Reb X") in a mixture of steviol glycosides can be obtained after separation of the crystals from the solution. In a particular embodiment, Reb X with a purity greater than about 60%, about 65%, about 75%, about 80%, about 85%, about 90% or about 95% is obtained by this process.

Those of skill in the art will recognize that the purity of the first crystals of Reb X will depend on the Reb X content of the initial solution of steviol glycosides among other variables. Accordingly, if needed, further wash steps can be performed to provide Reb X crystals with higher purity. To produce Reb X with greater purity, the first crystals of Reb X can combined with a aqueous alcohol solution (referred to herein as the "second aqueous alcohol solution") to provide second crystals of Reb X and a third aqueous alcohol solution. Separation of the second crystals of Reb X crystals from the third aqueous alcohol solution provides second crystals of Reb X having a purity greater than about 90% by weight on a dry basis. In certain embodiments, Reb X with purities greater than about 91%, about 92%, about 93%, about 94%, about 95%, about 96%, about 97%, about 98% or about 99% can be obtained. This process can be repeated, as necessary, until the desired purity level is achieved. The cycle can be repeated two times, three times, four times or five times. In some embodiments, water can be used instead of an aqueous alcohol solution.

The solution or suspension can be maintained at temperatures between about 40° C. to about 75° C., such as, for example, from about 50° C. to about 60° C. or about 55° C. to about 60° C. The duration that the mixture can be maintained at a temperature between about 40° C. to about 75° C. may vary, but can last between about 5 minutes and about 1 hour, such as, for example, between about 15 and about 30 minutes. The mixture can then be cooled to a temperature between about 20° C. to about 22° C., for example. The duration that the mixture can be maintained at the cool temperature may vary, but can last between about 1 hour and about 5 hours, such as, for example, between about 1 hour and about 2 hours. Agitation can optionally be used during the wash cycle.

Separation of Reb X crystals from the solution or suspension can be achieved by any known separation method, including, but not limited to, centrifugation, gravity or vacuum filtration, or drying. Different type of dryers such as fluid bed dryers, rotary tunnel dryers, or plate dryers may be used.

In some embodiments, when Reb X crystals are combined with water or aqueous alcohol solution, the Reb X may dissolve and accumulate in liquid phase. In that case the higher purity Reb X crystals may be obtained by drying or evaporative crystallization of liquid phase.

Sweetener Compositions

Sweetener compositions, as used herein, mean compositions that contain at least one sweet component in combination with at least one other substance, such as, for example, another sweetener or an additive.

Sweetenable compositions, as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

Sweetened compositions, as used herein, mean substances that contain both a sweetenable composition and a sweetener or sweetener composition.

For example, a beverage with no sweetener component is a type of sweetenable composition. A sweetener composition comprising Reb X and erythritol can be added to the unsweetened beverage, thereby providing a sweetened beverage. The sweetened beverage is a type of sweetened composition.

The sweetener compositions of the present invention include Reb X, 13-[(2-O-β-D-glucopyranosyl-3-O-β-D-glucopyranosyl-β-D-glucopyranosyl)oxy]ent kaur-16-en-19-oic acid-[(2-O-β-D-glucopyranosyl-3-O-β-D-glucopyranosyl-β-D-glucopyranosyl)ester] having the formula:

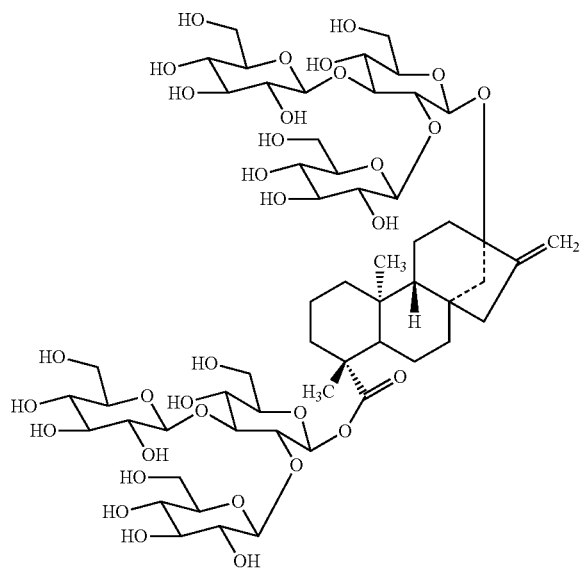

Reb X may be provided in a purified form or as a component of a mixture containing Reb X and one or more additional components (i.e. a sweetener composition comprising Reb X). In one embodiment, Reb X is provided as a component of a mixture. In a particular embodiment, the mixture is a *Stevia* extract. The *Stevia* extract may contain Reb X in an amount that ranges from about 5% to about 99% by weight on a dry basis, such as, for example, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In still further embodiments, the *Stevia* extract contains Reb X in an amount greater than about 90% by weight on a dry basis, for example, greater than about 91%, greater than about 92%, greater than about 93%, greater than about 94%, greater than about 95%, greater than about 96%, greater than about 97%, greater than about 98% and greater than about 99%.

In one embodiment, Reb X is provided as a component of a steviol glycoside mixture in a sweetener composition, i.e., a mixture of steviol glycosides wherein the remainder of the non-Reb X portion of the mixture is comprised entirely of steviol glycosides. The identities of steviol glycosides are known in the art and include, but are not limited to, steviol monoside, rubososide, steviolbioside, stevioside, rebaudioside A, rebaudioside B, rebaudioside C, rebaudioside D, rebaudioside E, rebaudioside F and dulcoside A. The steviol glycoside mixture may contain from about 5% to about 99% Reb X by weight on a dry basis. For example, a steviol glycoside mixture may contain from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99% Reb X by weight on a dry basis. In still further embodiments, the steviol glycoside mixture may contain greater than about 90% Reb X by weight on a dry basis, for example, greater than about 91%, greater than about 92%, greater than about 93%, greater than about 94%, greater than about 95%, greater than about 96%, greater than about 97%, greater than about 98% and greater than about 99%.

In one embodiment, Reb X is the sole sweetener in the sweetener composition, i.e. Reb X is the only compound present in the sweetener composition that provides sweetness. In another embodiment, Reb X is one of two or more sweetener compounds present in the sweetener composition.

The amount of sucrose in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, a sweetener composition contains Reb X in an amount effective to provide sweetness equivalent from about 0.50 to 14 degrees Brix of sugar when present in a sweetened composition, such as, for example, from about 5 to about 11 degrees Brix, from about 4 to about 7 degrees Brix, or about 5 degrees Brix. In another embodiment, Reb X is present in an amount effective to provide sweetness equivalent to about 10 degrees Brix when present in a sweetened composition.

The sweetness of a non-sucrose sweetener can also be measured against a sucrose reference by determining the non-sucrose sweetener's sucrose equivalence. Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose.

In one embodiment, Reb X is present in an effective amount to provide a sucrose equivalence of greater than about 10% (w/v) when present in a sweetened composition, such as, for example, greater than about 11%, greater than about 12%, greater than about 13% or greater than about 14%.

The amount of Reb X in the sweetener composition may vary. In one embodiment, Reb X is present in a sweetener composition in any amount to impart the desired sweetness when the sweetener composition is present in a sweetened composition. For example, Reb X is present in the sweetener composition in an amount effective to provide a Reb X concentration from about 1 ppm to about 10,000 ppm when present in a sweetened composition, such as, for example, from about 1 ppm to about 4,000 ppm, from about 1 ppm to about 3,000 ppm, from about 1 ppm to about 2,000 ppm, from about 1 ppm to about 1,000 ppm. In another embodiment, Reb X is present in the sweetener composition in an amount effective to provide a Reb X concentration from about 10 ppm to about 1,000 ppm when present in a sweetened composition, such as, for example, from about 10 ppm to about 800 ppm, from about 50 ppm to about 800 ppm, from about 50 ppm to about 600 ppm or from about 200 ppm to about 250 ppm. In a particular embodiment, Reb X is present in the sweetener composition in an amount effective to provide a Reb X concentration from about 300 ppm to about 600 ppm.

In some embodiments, sweetener compositions contain one or more additional sweeteners. The additional sweetener can be any type of sweetener, for example, a natural, non-natural, or synthetic sweetener. In at least one embodiment, the at least one additional sweetener is chosen from natural sweeteners other than *Stevia* sweeteners. In another embodiment, the at least one additional sweetener is chosen from synthetic high potency sweeteners.

For example, the at least one additional sweetener may be a carbohydrate sweetener. Non-limiting examples of suitable carbohydrate sweeteners include sucrose, fructose, glucose, erythritol, maltitol, lactitol, sorbitol, mannitol, xylitol, tagatose, trehalose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof. D- or L-configurations can be used when applicable.

In other embodiments, the additional sweetener is a carbohydrate sweetener selected from the group consisting of glucose, fructose, sucrose and combinations thereof.

In another embodiment, the additional sweetener is a carbohydrate sweetener selected from D-allose, D-psicose, L-ribose, D-tagatose, L-glucose, L-fucose, L-Arbinose, Turanose and combinations thereof.

The Reb X and carbohydrate sweetener may be present in any weight ratio, such as, for example, from about 0.001:14 to about 1:0.01, such as, for example, about 0.06:6. Carbohydrates are present in the sweetener composition in an amount effective to provide a concentration from about 100 ppm to about 140,000 ppm when present in a sweetened composition, such as, for example, a beverage.

In yet other embodiments, the at least one additional sweetener is a synthetic sweetener. As used herein, the phrase "synthetic sweetener" refers to any composition which is not found naturally in nature and characteristically has a sweetness potency greater than sucrose, fructose, or glucose, yet has less calories. Non-limiting examples of synthetic high-potency sweeteners suitable for embodiments of this disclosure include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof. The synthetic sweetener is present in the sweetener composition in an amount effective to provide a concentration from about 0.3 ppm to about 3,500 ppm when present in a sweetened composition, such as, for example, a beverage.

In still other embodiments, the additional sweetener can be a natural high potency sweetener. Suitable natural high potency sweeteners include, but are not limited to, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside 0, dulcoside A, dulcoside B, rubusoside, stevia, stevioside, mogroside IV, mogroside V, Luo Han Guo, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobtain, baiyunoside, osladin, polypodoside A, pterocaryoside A, pterocaryoside B, mukurozioside, phlomisoside I, periandrin I, abrusoside A, steviolbioside and cyclocarioside I. The natural high potency sweetener can be provided as a pure compound or, alternatively, as part of an extract. For example, rebaudioside A can be provided as a sole compound or as part of a Stevia extract. The natural high potency sweetener is present in the sweetener composition in an amount effective to provide a concentration from about 0.1 ppm to about 3,000 ppm when present in a sweetened composition, such as, for example, a beverage.

In still other embodiments, the additional sweetener can be chemically or enzymatically modified natural high potency sweetener. Modified natural high potency sweeteners include glycosylated natural high potency sweetener such as glucosyl-, galactosyl-, fructosyl-derivatives containing 1-50 glycosidic residues. Glycosylated natural high potency sweeteners may be prepared by enzymatic transglycosylation reaction catalyzed by various enzymes possessing transglycosylating activity.

In another particular embodiment, a sweetener compositions comprises Reb X and at least one other sweetener that functions as the sweetener component (i.e. the substance or substances that provide sweetness) of a sweetener composition. The sweetener compositions often exhibit synergy when combined and have improved flavor and temporal profiles compared to each sweetener alone. One or more additional sweetener can be used in the sweetener compositions. In one embodiment, a sweeteners composition contains Reb X and one additional sweetener. In other embodiments, a sweetener composition contains Reb X and more than one additional sweetener. The at least one other sweetener can be selected from the group consisting of erythritol, Reb B, NSF-02, mogroside V, Reb A, Reb D and combinations thereof.

In one embodiment, a sweetener composition comprises Reb X and erythritol as the sweetener component. The relative weight percent of Reb X and erythritol can vary. Generally, erythritol can comprise from about 0.1% to about 3.5% by weight of the sweetener component.

In another embodiment, a sweetener composition comprises Reb X and Reb B as the sweetener component. The relative weight percent of Reb X and Reb B can each vary from about 1% to about 99%, such as for example, about 95% Reb X/5% Reb B, about 90% Reb X/10% Reb B, about 85% Reb X/15% Reb B, about 80% Reb X/20% Reb B, about 75% Reb X/25% Reb B, about 70% Reb X/30% Reb B, about 65% Reb X/35% Reb B, about 60% Reb X/40% Reb B, about 55% Reb X/45% Reb B, about 50% Reb X/50% Reb B, about 45% Reb X/55% Reb B, about 40% Reb X/60% Reb B, about 35% Reb X/65% Reb B, about 30% Reb X/70% Reb B, about 25% Reb X/75% Reb B, about 20% Reb X/80% Reb B, about 15% Reb X/85% Reb B, about 10% Reb X/90% Reb B or about 5% Reb X/10% Reb B. In a particular embodiment, Reb B comprises from about 5% to about 40% of the sweetener component, such as, for example, from about 10% to about 30% or about 15% to about 25%.

In yet another embodiment, a sweetener composition comprises Reb X and NSF-02 (a GSG-type sweetener, available from PureCircle) as the sweetener component. The relative weight percent of Reb X and NSF-02 can each vary from about 1% to about 99%, such as for example, about 95% Reb X/5% NSF-02, about 90% Reb X/10% NSF-02, about 85% Reb X/15% NSF-02, about 80% Reb X/20% NSF-02, about 75% Reb X/25% NSF-02, about 70% Reb X/30% NSF-02, about 65% Reb X/35% NSF-02, about 60% Reb X/40% NSF-02, about 55% Reb X/45% NSF-02, about 50% Reb X/50% NSF-02, about 45% Reb X/55% NSF-02, about 40%

Reb X/60% NSF-02, about 35% Reb X/65% NSF-02, about 30% Reb X/70% NSF-02, about 25% Reb X/75% NSF-02, about 20% Reb X/80% NSF-02, about 15% Reb X/85% NSF-02, about 10% Reb X/90% NSF-02 or about 5% Reb X/10% NSF-02. In a particular embodiment, NSF-02 comprises from about 5% to about 50% of the sweetener component, such as, for example, from about 10% to about 40% or about 30% to about 30%.

In still another embodiment, a sweetener composition comprises Reb X and mogroside V as the sweetener component. The relative weight percent of Reb X and mogroside V can each vary from about 1% to about 99%, such as for example, about 95% Reb X/5% mogroside V, about 90% Reb X/10% mogroside V, about 85% Reb X/15% mogroside V, about 80% Reb X/20% mogroside V, about 75% Reb X/25% mogroside V, about 70% Reb X/30% mogroside V, about 65% Reb X/35% mogroside V, about 60% Reb X/40% mogroside V, about 55% Reb X/45% mogroside V, about 50% Reb X/50% mogroside V, about 45% Reb X/55% mogroside V, about 40% Reb X/60% mogroside V, about 35% Reb X/65% mogroside V, about 30% Reb X/70% mogroside V, about 25% Reb X/75% mogroside V, about 20% Reb X/80% mogroside V, about 15% Reb X/85% mogroside V, about 10% Reb X/90% mogroside V or about 5% Reb X/10% mogroside V. In a particular embodiment, mogroside V comprises from about 5% to about 50% of the sweetener component, such as, for example, from about 10% to about 40% or about 30% to about 30%.

In another embodiment, a sweetener composition comprises Reb X and Reb A as the sweetener component. The relative weight percent of Reb X and Reb A can each vary from about 1% to about 99%, such as for example, about 95% Reb X/5% Reb A, about 90% Reb X/10% Reb A, about 85% Reb X/15% Reb A, about 80% Reb X/20% Reb A, about 75% Reb X/25% Reb A, about 70% Reb X/30% Reb A, about 65% Reb X/35% Reb A, about 60% Reb X/40% Reb A, about 55% Reb X/45% Reb A, about 50% Reb X/50% Reb A, about 45% Reb X/55% Reb A, about 40% Reb X/60% Reb A, about 35% Reb X/65% Reb A, about 30% Reb X/70% Reb A, about 25% Reb X/75% Reb A, about 20% Reb X/80% Reb A, about 15% Reb X/85% Reb A, about 10% Reb X/90% Reb A or about 5% Reb X/10% Reb A. In a particular embodiment, Reb A comprises from about 5% to about 40% of the sweetener component, such as, for example, from about 10% to about 30% or about 15% to about 25%.

In another embodiment, a sweetener composition comprises Reb X and Reb D as the sweetener component. The relative weight percent of Reb X and Reb D can each vary from about 1% to about 99%, such as for example, about 95% Reb X/5% Reb D, about 90% Reb X/10% Reb D, about 85% Reb X/15% Reb D, about 80% Reb X/20% Reb D, about 75% Reb X/25% Reb D, about 70% Reb X/30% Reb D, about 65% Reb X/35% Reb D, about 60% Reb X/40% Reb D, about 55% Reb X/45% Reb D, about 50% Reb X/50% Reb D, about 45% Reb X/55% Reb D, about 40% Reb X/60% Reb D, about 35% Reb X/65% Reb D, about 30% Reb X/70% Reb D, about 25% Reb X/75% Reb D, about 20% Reb X/80% Reb D, about 15% Reb X/85% Reb D, about 10% Reb X/90% Reb D or about 5% Reb X/10% Reb D. In a particular embodiment, Reb D comprises from about 5% to about 40% of the sweetener component, such as, for example, from about 10% to about 30% or about 15% to about 25%.

In another embodiment, a sweetener composition comprises Reb X, Reb A and Reb D as the sweetener component. The relative weight percent of Reb X, Reb D and Reb A can each vary from about 1% to about 99%.

In still another embodiment, a sweetener composition comprises Reb X, Reb B and Reb D as the sweetener component. The relative weight percent of Reb X, Reb B and Reb D can each vary from about 1% to about 99%.

The sweetener compositions can be customized to provide the desired calorie content. For example, sweetener compositions can be "full-calorie", such that they impart the desired sweetness when added to a sweetenable composition (such as, for example, a beverage) and have about 120 calories per 8 oz serving. Alternatively, sweetener compositions can be "mid-calorie", such that they impart the desired sweetness when added to a sweetenable composition (such as, for example, as beverage) and have less than about 60 calories per 8 oz serving. In other embodiments, sweetener compositions can be "low-calorie", such that they impart the desired sweetness when added to a sweetenable composition (such as, for example, as beverage) and have less than 40 calories per 8 oz serving. In still other embodiments, the sweetener compositions can be "zero-calorie", such that they impart the desired sweetness when added to a sweetenable composition (such as, for example, a beverage) and have less than 5 calories per 8 oz. serving.

Additives

In addition to Reb X and, optionally, other sweeteners, the sweetener compositions can optionally include additional additives, detailed herein below. In some embodiments, the sweetener composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile of the sweetener to provide a sweetener composition with a taste similar to sucrose.

In one embodiment, the sweetener compositions contain one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the sweetener composition.

In certain embodiments, the polyol is present in the sweetener composition in an amount effective to provide a concentration from about 100 ppm to about 250,000 ppm when present in a sweetened composition, such as, for example, a beverage. In other embodiments, the polyol is present in the sweetener composition in an amount effective to provide a concentration from about 400 ppm to about 80,000 ppm when present in a sweetened composition, such as, for example, from about 5,000 ppm to about 40,000 ppm.

In other embodiments, Reb X and the polyol are present in the sweetener composition in a weight ratio from about 1:1 to about 1:800, such as, for example, from about 1:4 to about 1:800, from about 1:20 to about 1:600, from about 1:50 to about 1:300 or from about 1:75 to about 1:150.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise copolymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

In particular embodiments, the amino acid is present in the sweetener composition in an amount effective to provide a concentration from about 10 ppm to about 50,000 ppm when present in a sweetened composition, such as, for example, a beverage. In another embodiment, the amino acid is present in the sweetener composition in an amount effective to provide a concentration from about 1,000 ppm to about 10,000 ppm when present in a sweetened composition, such as, for example, from about 2,500 ppm to about 5,000 ppm or from about 250 ppm to about 7,500 ppm.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

The nucleotide is present in the sweetener composition in an amount effective to provide a concentration from about 5 ppm to about 1,000 ppm when present in sweetened composition, such as, for example, a beverage.

Suitable organic acid additives include any compound which comprises a—COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in the sweetener composition in an amount from about 10 ppm to about 5,000 ppm.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

The inorganic acid additive is present in the sweetener composition in an amount effective to provide a concentration from about 25 ppm to about 25,000 ppm when present in a sweetened composition, such as, for example, a beverage.

Suitable bitter compound additives include, but are not limited to, caffeine, quinine, urea, bitter orange oil, naringin, quassia, and salts thereof.

The bitter compound is present in the sweetener composition in an amount effective to provide a concentration from about 25 ppm to about 25,000 ppm when present in a sweetened composition, such as, for example, a beverage.

Suitable flavorant and flavoring ingredient additives for include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

The flavorant is present in the sweetener composition in an amount effective to provide a concentration from about 0.1 ppm to about 4,000 ppm when present in a sweetened composition, such as, for example, a beverage.

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

The polymer is present in the sweetener composition in an amount effective to provide a concentration from about 30 ppm to about 2,000 ppm when present in a sweetened composition, such as, for example, a beverage.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

The protein hydrosylate is present in the sweetener composition in an amount effective to provide a concentration from about 200 ppm to about 50,000 ppm when present in a sweetened composition, such as, for example, a beverage.

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

The surfactant additive is present in the sweetener composition in an amount effective to provide a concentration from about 30 ppm to about 2,000 ppm when present in a sweetened composition, such as, for example, a beverage.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

The flavonoid additive is present in the sweetener composition in an amount effective to provide a concentration from about 0.1 ppm to about 1,000 ppm when present in sweetened composition, such as, for example, a beverage.

Suitable alcohol additives include, but are not limited to, ethanol. In particular embodiments, the alcohol additive is present in the sweetener composition in an amount effective to provide a concentration from about 625 ppm to about 10,000 ppm when present in a sweetened composition, such as, for example, a beverage.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols). The astringent additive is present in the sweetener composition in an amount effective to provide a concentration from about 10 ppm to about 5,000 ppm when present in a sweetened composition, such as, for example, a beverage.

In particular embodiments, a sweetener composition comprises Reb X; a polyol selected from erythritol, maltitol, mannitol, xylitol, sorbitol, and combinations thereof; and optionally at least one additional sweetener and/or functional ingredient. The Reb X can be provided as a pure compound or as part of a *Stevia* extract or steviol glycoside mixture, as described above. Reb X can be present in an amount from about 5% to about 99% by weight on a dry basis in either a steviol glycoside mixture or a *Stevia* extract. In one embodiment, Reb X and the polyol are present in a sweetener composition in a weight ratio from about 1:1 to about 1:800, such as, for example, from about 1:4 to about 1:800, from about 1:20 to about 1:600, from about 1:50 to about 1:300 or from about 1:75 to about 1:150. In another embodiment, Reb X is present in the sweetener composition in an amount effective to provide a concentration from about 1 ppm to about 10,000 ppm when present in a sweetened composition, such as, for example, about 300 ppm. The polyol, such as, for example, erythritol, can be present in the sweetener composition in an amount effective to provide a concentration from about 100 ppm to about 250,000 ppm when present in a sweetened composition, such as, for example, from about 5,000 ppm to about 40,000 ppm, from about 1,000 ppm to about 35,000 ppm.

In particular embodiments, a sweetener composition comprises Reb X; a carbohydrate sweetener selected from sucrose, fructose, glucose, maltose and combinations thereof; and optionally at least one additional sweetener and/or functional ingredient. The Reb X can be provided as a pure compound or as part of a *Stevia* extract or steviol glycoside mixture, as described above. Reb X can be present in an amount from about 5% to about 99% by weight on a dry basis in either a steviol glycoside mixture or a *Stevia* extract. In one embodiment, Reb X and the carbohydrate are present in a sweetener composition in a weight ratio from about 0.001:14 to about 1:0.01, such as, for example, about 0.06:6. In one embodiment, Reb X is present in the sweetener composition in an amount effective to provide a concentration from about 1 ppm to about 10,000 ppm when present in a sweetened composition, such as, for example, about 500 ppm. The carbohydrate, such as, for example, sucrose, can be present in the sweetener composition in an amount effective to provide a concentration from about 100 ppm to about 140,000 ppm when present in a sweetened composition, such as, for example, from about 1,000 ppm to about 100,000 ppm, from about 5,000 ppm to about 80,000 ppm.

In particular embodiments, a sweetener composition comprises Reb X; an amino acid selected from glycine, alanine, proline and combinations thereof; and optionally at least one additional sweetener and/or functional ingredient. The Reb X can be provided as a pure compound or as part of a *Stevia* extract or steviol glycoside mixture, as described above. Reb X can be present in an amount from about 5% to about 99% by weight on a dry basis in either a steviol glycoside mixture or a *Stevia* extract. In another embodiment, Reb X is present in the sweetener composition in an amount effective to provide a concentration from about 1 ppm to about 10,000 ppm when present in a sweetened composition, such as, for example, about 500 ppm. The amino acid, such as, for example, glycine, can be present in the sweetener composition in an amount effective to provide a concentration from about 10 ppm to about 50,000 ppm when present in a sweetened composition, such as, for example, from about 1,000 ppm to about 10,000 ppm, from about 2,500 ppm to about 5,000 ppm In particular embodiments, a sweetener composition comprises Reb X; a salt selected from sodium chloride, magnesium chloride, potassium chloride, calcium chloride and combinations thereof; and optionally at least one additional sweetener and/or functional ingredient. The Reb X can be provided as a pure compound or as part of a *Stevia* extract or steviol glycoside mixture, as described above. Reb X can be present in an amount from about 5% to about 99% by weight on a dry basis in either a steviol glycoside mixture or a *Stevia* extract. In one embodiment, Reb X is present in the sweetener composition in an amount effective to provide a concentration from about 1 ppm to about 10,000 ppm, such as, for example, about 100 to about 1,000 ppm. The inorganic salt, such as, for example, magnesium chloride, is present in the sweetener composition in an amount effective to provide a concentration from about 25 ppm to about 25,000 ppm when present in a sweetened composition, such as, for example, from about 100 ppm to about 4,000 ppm or from about 100 ppm to about 3,000 ppm.

Functional Ingredients

The sweetener composition can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponin

In certain embodiments, the functional ingredient is at least one saponin. In one embodiment, a sweetener composition comprises at least one saponin, Reb X, and optionally at least one additive. In another embodiment, a sweetened composition comprises a sweetenable composition, at least one saponin, Reb X, and optionally at least one additive. In still another embodiment, a sweetened composition comprises a sweetenable composition and a sweetener composition, wherein the sweetener composition comprises at least one saponin, Reb X, and optionally at least one additive.

As used herein, the at least one saponin may comprise a single saponin or a plurality of saponins as a functional ingredient for the sweetener composition or sweetened compositions provided herein. Generally, according to particular embodiments of this invention, the at least one saponin is present in the sweetener composition or sweetened composition in an amount sufficient to promote health and wellness.

Saponins are glycosidic natural plant products comprising an aglycone ring structure and one or more sugar moieties. The combination of the nonpolar aglycone and the water soluble sugar moiety gives saponins surfactant properties, which allow them to form a foam when shaken in an aqueous solution.

The saponins are grouped together based on several common properties. In particular, saponins are surfactants which display hemolytic activity and form complexes with cholesterol. Although saponins share these properties, they are structurally diverse. The types of aglycone ring structures forming the ring structure in saponins can vary greatly. Non-limiting examples of the types of aglycone ring structures in saponin for use in particular embodiments of the invention include steroids, triterpenoids, and steroidal alkaloids. Non-limiting examples of specific aglycone ring structures for use in particular embodiments of the invention include soyasapogenol A, soyasapogenol B and soyasopogenol E. The number and type of sugar moieties attached to the aglycone ring structure can also vary greatly. Non-limiting examples of sugar moieties for use in particular embodiments of the invention include glucose, galactose, glucuronic acid, xylose, rhamnose, and methylpentose moieties. Non-limiting examples of specific saponins for use in particular embodiments of the invention include group A acetyl saponin, group B acetyl saponin, and group E acetyl saponin.

Saponins can be found in a large variety of plants and plant products, and are especially prevalent in plant skins and barks where they form a waxy protective coating. Several common sources of saponins include soybeans, which have approximately 5% saponin content by dry weight, soapwort plants (*Saponaria*), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

Antioxidant

In certain embodiments, the functional ingredient is at least one antioxidant. In one embodiment, a sweetener composition comprises at least one antioxidant, Reb X, and optionally at least one additive. In another embodiment, a sweetened composition comprises a sweetenable composition, at least one antioxidant, Reb X, and optionally at least one additive. In still another embodiment, a sweetened composition comprises a sweetenable composition and a sweetener composition, wherein the sweetener composition comprises at least one antioxidant, Reb X, and optionally, at least one additive.

As used herein, the at least one antioxidant may comprise a single antioxidant or a plurality of antioxidants as a functional ingredient for the sweetener composition or sweetened compositions provided herein. Generally, according to particular embodiments of this invention, the at least one antioxidant is present in the sweetener composition or sweetened composition in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention, include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is an anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is resveratrol. Suitable sources of resveratrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa spouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In some embodiments, the antioxidant is a citrus flavonoid, such as hesperidin or naringin. Suitable sources of citrus flavonids, such as hesperidin or naringin, for embodiments of this invention include, but are not limited to, oranges, grapefruits, and citrus juices.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, Echinacea, pycnogenol, and apple peel.

Dietary Fiber

In certain embodiments, the functional ingredient is at least one dietary fiber source. In one embodiment, a sweetener composition comprises at least one dietary fiber source, Reb X, and optionally at least one additive. In another embodiment, a sweetened composition comprises a sweetenable composition, at least one dietary fiber source, Reb X, and optionally at least one additive. In still another embodiment, a sweetened composition comprises a sweetenable composition and a sweetener composition, wherein the sweetener composition comprises at least one dietary fiber source, Reb X, and optionally at least one additive.

As used herein, the at least one dietary fiber source may comprise a single dietary fiber source or a plurality of dietary fiber sources as a functional ingredient for the sweetener compositions or sweetened compositions provided herein. Generally, according to particular embodiments of this invention, the at least one dietary fiber source is present in the sweetener composition or sweetened composition in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Polysaccharides are complex carbohydrates composed of monosaccharides joined by glycosidic linkages. Non-starch polysaccharides are bonded with β-linkages, which humans are unable to digest due to a lack of an enzyme to break the β-linkages. Conversely, digestible starch polysaccharides generally comprise α(1-4) linkages.

Lignin is a large, highly branched and cross-linked polymer based on oxygenated phenylpropane units. Cellulose is a linear polymer of glucose molecules joined by a β(1-4) linkage, which mammalian amylases are unable to hydrolyze. Methylcellulose is a methyl ester of cellulose that is often used in foodstuffs as a thickener, and emulsifier. It is commercially available (e.g., Citrucel by GlaxoSmithKline, Celevac by Shire Pharmaceuticals). Hemicelluloses are highly branched polymers consisting mainly of glucurono- and 4-O-methylglucuroxylans. β-Glucans are mixed-linkage (1-3), (1-4) β-D-glucose polymers found primarily in cereals, such as oats and barley. Pectins, such as beta pectin, are a group of polysaccharides composed primarily of D-galacturonic acid, which is methoxylated to variable degrees.

Gums and mucilages represent a broad array of different branched structures. Guar gum, derived from the ground endosperm of the guar seed, is a galactomannan. Guar gum is commercially available (e.g., Benefiber by Novartis AG). Other gums, such as gum arabic and pectins, have still different structures. Still other gums include xanthan gum, gellan gum, tara gum, psyllium seed husk gum, and locust been gum.

Waxes are esters of ethylene glycol and two fatty acids, generally occurring as a hydrophobic liquid that is insoluble in water.

Inulins comprise naturally occurring oligosaccharides belonging to a class of carbohydrates known as fructans. They generally are comprised of fructose units joined by β(2-1) glycosidic linkages with a terminal glucose unit. Oligosaccharides are saccharide polymers containing typically three to six component sugars. They are generally found either O- or N-linked to compatible amino acid side chains in proteins or to lipid molecules. Fructooligosaccharides are oligosaccharides consisting of short chains of fructose molecules.

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Sources of dietary fiber often are divided into categories of soluble and insoluble fiber based on their solubility in water. Both soluble and insoluble fibers are found in plant foods to varying degrees depending upon the characteristics of the plant. Although insoluble in water, insoluble fiber has passive hydrophilic properties that help increase bulk, soften stools, and shorten transit time of fecal solids through the intestinal tract.

Unlike insoluble fiber, soluble fiber readily dissolves in water. Soluble fiber undergoes active metabolic processing via fermentation in the colon, increasing the colonic microflora and thereby increasing the mass of fecal solids. Fermentation of fibers by colonic bacteria also yields end-products with significant health benefits. For example, fermentation of the food masses produces gases and short-chain fatty acids. Acids produced during fermentation include butyric, acetic, propionic, and valeric acids that have various beneficial properties such as stabilizing blood glucose levels by acting on pancreatic insulin release and providing liver control by glycogen breakdown. In addition, fiber fermentation may reduce atherosclerosis by lowering cholesterol synthesis by the liver and reducing blood levels of LDL and triglycerides. The acids produced during fermentation lower colonic pH, thereby protecting the colon lining from cancer polyp formation. The lower colonic pH also increases mineral absorption, improves the barrier properties of the colonic mucosal layer, and inhibits inflammatory and adhesion irritants. Fermentation of fibers also may benefit the immune system by stimulating production of T-helper cells, antibodies, leukocytes, splenocytes, cytokinins and lymphocytes.

Fatty Acid

In certain embodiments, the functional ingredient is at least one fatty acid. In one embodiment, a sweetener composition comprises at least one fatty acid, Reb X, and optionally at least one additive. In another embodiment, a sweetened composition comprises a sweetenable composition, at least one fatty acid, Reb X, and optionally at least one additive. In still another embodiment, a sweetened composition comprises a sweetenable composition and a sweetener composition, wherein the sweetener composition comprises at least one fatty acid, Reb X, and optionally at least one additive.

As used herein, the at least one fatty acid may be single fatty acid or a plurality of fatty acids as a functional ingredient for the sweetener composition or sweetened compositions provided herein. Generally, according to particular embodiments of this invention, the at least one fatty acid is present in the sweetener composition or sweetened composition in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin. In one embodiment, a sweetener composition comprises at least one vitamin, Reb X, and optionally at least one additive. In another embodiment, a sweetened composition comprises a sweetenable composition, at least one vitamin, Reb X, and optionally at least one additive. In still another embodiment, a sweetened composition comprises a sweetenable composition and a sweetener composition, wherein the sweetener composition comprises at least one vitamin, Reb X, and optionally at least one additive. As used herein, the at least one vitamin may be single vitamin or a plurality of vitamins as a functional ingredient for the sweetener and sweetened compositions provided herein. Generally, according to particular embodiments of this invention, the at least one vitamin is present in the sweetener composition or sweetened composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the functional sweetener and sweetened compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C. Many of vitamins also have alternative chemical names, non-limiting examples of which are provided below.

| Vitamin | Alternative names |
| --- | --- |
| Vitamin A | Retinol |
| | Retinaldehyde |
| | Retinoic acid |
| | Retinoids |
| | Retinal |
| | Retinoic ester |
| Vitamin D (vitamins D1-D5) | Calciferol |
| | Cholecalciferol |
| | Lumisterol |
| | Ergocalciferol |
| | Dihydrotachysterol |
| | 7-dehydrocholesterol |
| Vitamin E | Tocopherol |
| | Tocotrienol |
| Vitamin K | Phylloquinone |
| | Naphthoquinone |
| Vitamin B1 | Thiamin |
| Vitamin B2 | Riboflavin |
| | Vitamin G |
| Vitamin B3 | Niacin |
| | Nicotinic acid |
| | Vitamin PP |
| Vitamin B5 | Pantothenic acid |
| Vitamin B6 | Pyridoxine |
| | Pyridoxal |
| | Pyridoxamine |
| Vitamin B7 | Biotin |
| | Vitamin H |
| Vitamin B9 | Folic acid |
| | Folate |
| | Folacin |
| | Vitamin M |
| | Pteroyl-L-glutamic acid |
| Vitamin B12 | Cobalamin |
| | Cyanocobalamin |
| Vitamin C | Ascorbic acid |

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine. In one embodiment, a sweetener composition comprises glucosamine, Reb X, and optionally at least one additive. In another embodiment, a sweetened composition comprises a sweetenable composition, glucosamine, Reb X, and optionally at least one additive. In still another embodiment, a sweetened composition comprises a sweetenable composition and a sweetener composition, wherein the sweetener composition comprises glucosamine, Reb X, and optionally at least one additive.

Generally, according to particular embodiments of this invention, glucosamine is present in the functional sweetener composition or sweetened composition in an amount sufficient to promote health and wellness.

Glucosamine, also called chitosamine, is an amino sugar that is believed to be an important precursor in the biochemical synthesis of glycosylated proteins and lipids. D-glucosamine occurs naturally in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof. Glucosamine may be obtained by acid hydrolysis of the shells of lobsters, crabs, shrimps, or prawns using methods well known to those of ordinary skill in the art. In a particular embodiment, glucosamine may be derived from fungal biomass containing chitin, as described in U.S. Patent Publication No. 2006/0172392.

The sweetener compositions or sweetened composition can further comprise chondroitin sulfate.

Mineral

In certain embodiments, the functional ingredient is at least one mineral. In one embodiment, a sweetener composition comprises at least one mineral, Reb X, and optionally at least one additive. In another embodiment, a sweetened composition comprises a sweetenable composition, at least one mineral, Reb X, and optionally at least one additive. In still another embodiment, a sweetened composition comprises a sweetenable composition and a sweetener composition, wherein the sweetener composition comprises at least one mineral, Reb X, and optionally at least one additive.

As used herein, the at least one mineral may be single mineral or a plurality of minerals as a functional ingredient for the sweetener compositions or sweetened compositions provided herein. Generally, according to particular embodiments of this invention, the at least one mineral is present in the sweetener composition or sweetened composition in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative. In one embodiment, a sweetener composition comprises at least one preservative, Reb X, and optionally at least one additive. In another embodiment, a sweetened composition comprises a sweetenable composition, at least one preservative, Reb X, and optionally at least one additive. In still another embodiment, a sweetened composition comprises a sweetenable composition and a sweetener composition, wherein the sweetener composition comprises at least one preservative, Reb X, and optionally at least one additive.

As used herein, the at least one preservative may be single preservative or a plurality of preservatives as a functional ingredient for the sweetener compositions or sweetened composition provided herein. Generally, according to particular embodiments of this invention, the at least one preservative is present in the sweetener composition or sweetened composition in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent. In one embodiment, a sweetener composition comprises at least one hydration agent, Reb X, and optionally at least one additive. In another embodiment, a sweetened composition comprises a sweetenable composition, at least one hydration agent, Reb X, and optionally at least one additive. In still another embodiment, a sweetened composition comprises a sweetenable composition and a sweetener composition, wherein the sweetener composition comprises at least one hydration gent, Reb X, and optionally at least one additive.

As used herein, the at least one hydration agent may be single hydration agent or a plurality of hydration agents as a functional ingredient for the sweetener compositions or sweetened composition provided herein. Generally, according to particular embodiments of this invention, the at least one hydration agent is present in the sweetener composition or sweetened composition in an amount sufficient to promote health and wellness.

Hydration products help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartates, sorbates, citrates, benzoates, or combinations thereof. In other embodiments, the electrolytes are provided by juice, fruit extracts, vegetable extracts, tea, or teas extracts.

In particular embodiments of this invention, the hydration product is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration product is a glycerol solution to enhance exercise endurance. The ingestion of a glycerol containing solution has been shown to provide beneficial physiological effects, such as expanded blood volume, lower heart rate, and lower rectal temperature.

Probiotics/Prebiotics

In certain embodiments, the functional ingredient is chosen from at least one probiotic, prebiotic and combination thereof. In one embodiment, a sweetener composition comprises at least one probiotic, prebiotic and combination thereof. Reb X; and optionally at least one additive. In another embodiment, a sweetened composition comprises a sweetenable composition, at least one at least one probiotic, prebiotic and combination thereof. Reb X; and optionally at least one additive. In still another embodiment, a sweetened composition comprises a sweetenable composition and a sweetener composition, wherein the sweetener composition comprises at least one probiotic, prebiotic and combination thereof. Reb X; and optionally at least one additive.

As used herein, the at least one probiotic or prebiotic may be single probiotic or prebiotic or a plurality of probiotics or prebiotics as a functional ingredient for the sweetener compositions or sweetened composition provided herein. Generally, according to particular embodiments of this invention, the at least one probiotic, prebiotic or combination thereof is present in the sweetener composition or sweetened composition in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus

*Lactobacilli, Bifidobacteria, Streptococci*, or combinations thereof, that confer beneficial effects to humans.

In particular embodiments of the invention, the at least one probiotic is chosen from the genus *Lactobacilli*. *Lactobacilli* (i.e., bacteria of the genus *Lactobacillus*, hereinafter "L.") have been used for several hundred years as a food preservative and for promoting human health. Non-limiting examples of species of *Lactobacilli* found in the human intestinal tract include *L. acidophilus, L. casei, L. fermentum, L. saliva roes, L. brevis, L. leichmannii, L. plantarum, L. cellobiosus, L. reuteri, L. rhamnosus, L. GG, L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum, B. animalis, B. asteroides, B. bifidum, B. bourn, B. breve, B. catenulatum, B. choerinum, B. coryneforme, B. cuniculi, B. dentium, B. gallicum, B. gallinarum, B indicum, B. longum, B. magnum, B. merycicum, B. minimum, B. pseudocatenulatum, B. pseudolongum, B. psychraerophilum, B. pullorum, B. ruminanfium, B. saeculare, B. scardovii, B. simiae, B. subtile, B. thermacidophilum, B. thermophilum, B. urinalis*, and *B. sp*.

According to other particular embodiments of this invention, the probiotic is chosen from the genus *Streptococcus*. *Streptococcus* thermophilus is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent. In one embodiment, a sweetener composition comprises at least one weight management agent, Reb X, and optionally at least one additive. In another embodiment, a sweetened composition comprises a sweetenable composition, at least one weight management agent, Reb X, and optionally at least one additive. In still another embodiment, a sweetened composition comprises a sweetenable composition and a sweetener composition, wherein the sweetener composition comprises at least one weight management agent, Reb X, and optionally at least one additive.

As used herein, the at least one weight management agent may be single weight management agent or a plurality of weight management agents as a functional ingredient for the sweetener compositions or sweetened composition provided herein. Generally, according to particular embodiments of this invention, the at least one weight management agent is present in the sweetener composition or sweetened composition in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Polyunsaturated fatty acids have been shown to have a greater satiating power than mono-unsaturated fatty acids. Accordingly, the dietary fats embodied herein desirably comprise polyunsaturated fatty acids, non-limiting examples of which include triacylglycerols.

In a particular embodiment, the weight management agents is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from Gymnema Sylvestre, Kola Nut, Citrus Aurantium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii,* and *H. triebneri*. *Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculate, C. edulis, C. adscendens, C. stalagmifera, C. umbellate, C. penicillata, C. russeliana, C. retrospicens, C. Arabica,* and *C. lasiantha*. *Carralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca,* and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

The at least one weight management agent may be utilized individually or in combination as a functional ingredient for the sweetener compositions provided in this invention.

Osteoporosis Management Agent

In certain embodiments, the functional ingredient is at least one osteoporosis management agent. In one embodiment, a sweetener composition comprises at least one osteoporosis management agent, Reb X, and optionally at least one additive. In another embodiment, a sweetened composition comprises a sweetenable composition, at least one osteoporosis management agent, Reb X, and optionally at least one additive. In still another embodiment, a sweetened composition comprises a sweetenable composition and a sweetener composition, wherein the sweetener composition comprises at least one osteoporosis management agent, Reb X, and optionally at least one additive.

As used herein, the at least one osteoporosis management agent may be single osteoporosis management agent or a plurality of osteoporosis management agent as a functional ingredient for the sweetener compositions or sweetened composition provided herein. Generally, according to particular embodiments of this invention, the at least one osteoporosis management agent is present in the sweetener composition or sweetened composition in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone micro-architecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus*, and *Anethum*, as disclosed in U.S. Patent Publication No. 2005/0079232.

Phytoestrogen

In certain embodiments, the functional ingredient is at least one phytoestrogen. In one embodiment, a sweetener composition comprises at least one phytoestrogen, Reb X, and optionally at least one additive. In another embodiment, a sweetened composition comprises a sweetenable composition, at least one phytoestrogen, Reb X, and optionally at least one additive. In still another embodiment, a sweetened composition comprises a sweetenable composition and a sweetener composition, wherein the sweetener composition comprises at least one phytoestrogen, Reb X, and optionally at least one additive.

As used herein, the at least one phytoestrogen may be single phytoestrogen or a plurality of phytoestrogens as a functional ingredient for the sweetener compositions or sweetened composition provided herein. Generally, according to particular embodiments of this invention, the at least one phytoestrogen is present in the sweetener composition or sweetened composition in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa spouts, chickpeas, peanuts, and red clover.

Long-Chain Primary Aliphatic Saturated Alcohol

In certain embodiments, the functional ingredient is at least one long chain primary aliphatic saturated alcohol. In one embodiment, a sweetener composition comprises at least one long chain primary aliphatic saturated alcohol, Reb X, and optionally at least one additive. In another embodiment, a sweetened composition comprises a sweetenable composition, at least one long chain primary aliphatic saturated alcohol, Reb X, and optionally at least one additive. In still another embodiment, a sweetened composition comprises a sweetenable composition and a sweetener composition, wherein the sweetener composition comprises at least one long chain primary aliphatic saturated alcohol, Reb X, and optionally at least one additive. As used herein, the at least one long chain primary aliphatic saturated alcohol may be single long chain primary aliphatic saturated alcohol or a plurality of long chain primary aliphatic saturated alcohols as a functional ingredient for the sweetener compositions or sweetened composition provided herein. Generally, according to particular embodiments of this invention, the at least one long chain primary aliphatic saturated alcohol is present in the sweetener composition or sweetened composition in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Long-chain primary aliphatic saturated alcohols are derived from natural fats and oils. They may be obtained from these sources by using extraction techniques well known to those of ordinary skill in the art. Policosanols can be isolated from a variety of plants and materials including sugar cane (*Saccharum officinarium*), yams (e.g. *Dioscorea opposite*), bran from rice (e.g. *Oryza sativa*), and beeswax. Policosanols may be obtained from these sources by using extraction techniques well known to those of ordinary skill in the art. A description of such extraction techniques can be found in U.S. Pat. Appl. No. 2005/0220868, the disclosure of which is expressly incorporated by reference.

Phytosterols

In certain embodiments, the functional ingredient is at least one phytosterol, phytostanol or combination thereof. In one embodiment, a sweetener composition comprises at least one phytosterol, phytostanol or combination thereof. Reb X; and optionally at least one additive. In another embodiment, a sweetened composition comprises a sweetenable composition, at least one phytosterol, phytostanol or combination thereof. Reb X; and optionally, at least one additive. In still another embodiment, a sweetened composition comprises a sweetenable composition and a sweetener composition, wherein the sweetener composition comprises at least one phytosterol, phytostanol or combination thereof. Reb X; and optionally at least one additive.

Generally, according to particular embodiments of this invention, the at least one phytosterol, phytostanol or combination thereof is present in the sweetener composition or sweetened composition in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the sweetener composition or sweetened composition varies widely depending on the particular sweetener composition or sweetened composition and the desired functional ingredient. Those of ordinary skill in the art will readily ascertain the appropriate amount of functional ingredient for each sweetener composition or sweetened composition.

In one embodiment, a method for preparing a sweetener composition comprises combining Reb X and at least one sweetener and/or additive and/or functional ingredient. In another embodiment, a method for preparing a sweetener composition comprises combining a composition comprising Reb X and at least one sweetener and/or additive and/or functional ingredient. Reb X can be provided in its pure form as the sole sweetener in the sweetener composition, or it can be provided as part of a steviol glycoside mixture of *Stevia* extract. Any of the sweeteners, additives and functional ingredients described herein can be used the in the sweetener compositions of the present invention.

Sweetened Compositions

Reb X or sweetener compositions comprising Reb X can be incorporated in any known edible material (referred to herein as a "sweetenable composition"), such as, for example, pharmaceutical compositions, edible gel mixes and compositions, dental compositions, foodstuffs (confections, condiments, chewing gum, cereal compositions baked goods dairy products, and tabletop sweetener compositions) beverages and beverage products.

In one embodiment, sweetened composition comprises a sweetenable composition and Reb X. In another embodiment, the sweetened composition comprises a sweetener composition comprising Reb X. The sweetened compositions can optionally include additives, sweeteners, functional ingredients and combinations thereof.

In one embodiment, a method for preparing a sweetened composition comprises combining a sweetenable composition and Reb X. The method can further comprise adding and at least one sweetener and/or additive and/or functional ingredient. In another embodiment, a method for preparing a sweetened composition comprises combining a sweetenable composition and a sweetener composition comprising Reb X. Reb X can be provided in its pure form as the sole sweetener in the sweetener composition, or it can be provided as part of a steviol glycoside mixture of *Stevia* extract. Any of the sweeteners, additives and functional ingredients described herein can be used the in the sweetened compositions of the present invention. In a particular embodiment, the sweetenable composition is a beverage.

Pharmaceutical Compositions

In one embodiment, a pharmaceutical composition contains a pharmaceutically active substance and Reb X. In another embodiment, a pharmaceutical composition contains a pharmaceutically active substance and a sweetener composition comprising Reb X. The Reb X or Reb X sweetener composition can be present as an excipient material in the pharmaceutical composition, which can mask a bitter or otherwise undesirable taste of a pharmaceutically active substance or another excipient material. The pharmaceutical composition may be in the form of a tablet, a capsule, a liquid, an aerosol, a powder, an effervescent tablet or powder, a syrup, an emulsion, a suspension, a solution, or any other form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. As referred to herein, "excipient material" refers to any inactive substance used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculoskeletal disorders, for the eye, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders. Examples of suitable pharmaceutically active substances for embodiments of the present invention include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-gluacoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosphonates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutically active substance is present in the pharmaceutical composition in widely ranging amounts depending on the particular pharmaceutically active agent being used and its intended applications. An effective dose of any of the herein described pharmaceutically active substances can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular pharmaceutically active agent administered; the mode of administration; the bioavailability characteristic of the preparation administered; the dose regimen selected; and the use of concomitant medication. The pharmaceutically active substance is included in the pharmaceutically acceptable carrier, diluent, or excipient in an amount sufficient to deliver to a patient a therapeutic amount of the pharmaceutically active substance in vivo in the absence of serious toxic effects when used in generally acceptable amounts. Thus, suitable amounts can be readily discerned by those skilled in the art.

According to particular embodiments of the present invention, the concentration of pharmaceutically active substance in the pharmaceutical composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimes should be adjusted over time according to the individual need and the professional judgment of the person administering or supervising the administration of the pharmaceutical compositions, and that the dosage ranges set forth herein are exemplary only and are not intended to limit the scope or practice of the claimed composition. The pharmaceutically active substance may be administered at once, or may be divided into a number of smaller doses to be administered at varying intervals of time.

The pharmaceutical composition also may comprise other pharmaceutically acceptable excipient materials in addition to Reb X or a sweetener composition comprising Reb X. Examples of suitable excipient materials for embodiments of this invention include, but are not limited to, antiadherents, binders (e.g., microcrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

The excipient material of the pharmaceutical composition may optionally include other artificial or natural sweeteners, bulk sweeteners, or combinations thereof. Bulk sweeteners include both caloric and non-caloric compounds. In a particular embodiment, the additive functions as the bulk sweetener. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the pharmaceutical composition in widely ranging amounts depending on the degree of sweetness desired. Suitable amounts of both sweeteners would be readily discernable to those skilled in the art.

Edible Gel Mixes and Edible Gel Compositions

In one embodiment, an edible gel or edible gel mix comprises Reb X. In another embodiment, an edible gel or edible gel mix comprises a sweetener composition comprising Reb X. The edible gel or edible gel mixes can optionally include additives, functional ingredients or combinations thereof.

Edible gels are gels that can be eaten. A gel is a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives.

Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

As used herein, the term "gelling ingredient" denotes any material that can form a colloidal system within a liquid medium. Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

It is well known to those having ordinary skill in the art that the edible gel mixes and edible gels may be prepared using other ingredients in addition to Reb X, or the sweetener composition comprising Reb X, and the gelling agent. Non-limiting examples of other ingredients for use in particular embodiments include a food acid, a salt of a food acid, a buffering system, a bulking agent, a sequestrant, a cross-linking agent, one or more flavors, one or more colors, and combinations thereof. Non-limiting examples of food acids for use in particular embodiments include citric acid, adipic acid, fumaric acid, lactic acid, malic acid, and combinations thereof. Non-limiting examples of salts of food acids for use in particular embodiments include sodium salts of food acids, potassium salts of food acids, and combinations thereof. Non-limiting examples of bulking agents for use in particular embodiments include raftilose, isomalt, sorbitol, polydextrose, maltodextrin, and combinations thereof. Non-limiting examples of sequestrants for use in particular embodiments include calcium disodium ethylene tetra-acetate, glucono delta-lactone, sodium gluconate, potassium gluconate, ethylenediaminetetraacetic acid (EDTA), and combinations thereof. Non-limiting examples of cross-linking agents for use in particular embodiments include calcium ions, magnesium ions, sodium ions, and combinations thereof.

Dental Compositions

In one embodiment, a dental composition comprises Reb X. In another embodiment, a dental composition comprises a sweetener composition comprising Reb X. Dental compositions generally comprise an active dental substance and a base material. Reb X, or a sweetener composition comprising Reb X, can be used as the base material to sweeten the dental composition. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

As referred to herein, "active dental substance" means any composition which can be used to improve the aesthetic appearance and/or health of teeth or gums or prevent dental caries. As referred to herein, "base material" refers to any inactive substance used as a vehicle for an active dental substance, such as any material to facilitate handling, stability, dispersibility, wettability, foaming, and/or release kinetics of an active dental substance.

Suitable active dental substances for embodiments of this invention include, but are not limited to, substances which remove dental plaque, remove food from teeth, aid in the elimination and/or masking of halitosis, prevent tooth decay, and prevent gum disease (i.e., Gingiva). Examples of suitable active dental substances for embodiments of the present invention include, but are not limited to, anticaries drugs, fluoride, sodium fluoride, sodium monofluorophosphate, stannos fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

According to particular embodiments of the invention, the active dental substance is present in the dental composition in an amount ranging from about 50 ppm to about 3000 ppm of the dental composition. Generally, the active dental substance is present in the dental composition in an amount effective to at least improve the aesthetic appearance and/or health of teeth or gums marginally or prevent dental caries. For example, a dental composition comprising a toothpaste may include an active dental substance comprising fluoride in an amount of about 850 to 1,150 ppm.

The dental composition also may comprise other base materials in addition to the Reb X or sweetener composition comprising Reb X. Examples of suitable base materials for embodiments of this invention include, but are not limited to, water, sodium lauryl sulfate or other sulfates, humectants, enzymes, vitamins, herbs, calcium, flavorings (e.g., mint, bubblegum, cinnamon, lemon, or orange), surface-active agents, binders, preservatives, gelling agents, pH modifiers, peroxide activators, stabilizers, coloring agents, or similar type materials, and combinations thereof.

The base material of the dental composition may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the dental composition ranges widely depending on the particular embodiment of the dental composition and the desired degree of sweetness. Those of ordinary skill in the art will readily ascertain the appropriate amount of bulk sweetener. In particular embodiments, the bulk sweetener is present in the dental composition in an amount in the range of about 0.1 to about 5 weight percent of the dental composition.

According to particular embodiments of the invention, the base material is present in the dental composition in an amount ranging from about 20 to about 99 percent by weight of the dental composition. Generally, the base material is present in an amount effective to provide a vehicle for an active dental substance.

In a particular embodiment, a dental composition comprises Reb X and an active dental substance. In another particular embodiment, a dental composition comprises a sweetener composition comprising Reb X and an active dental substance. Generally, the amount of the sweetener varies widely depending on the nature of the particular dental composition and the desired degree of sweetness. Those skilled in the art will be able to discern a suitable amount of sweetener for such dental composition. In a particular embodiment, Reb X is present in the dental composition in an amount in the range of about 1 to about 5,000 ppm of the dental composition and the at least one additive is present in the dental composition in an amount in the range of about 0.1 to about 100,000 ppm of the dental composition.

Foodstuffs include, but are not limited to, confections, condiments, chewing gum, cereal, baked goods, and dairy products.

Confections

In one embodiment, a confection comprises Reb X. In another embodiment, a confection comprises a sweetener composition comprising Reb X.

As referred to herein, "confection" can mean a sweet, a lollie, a confectionery, or similar term. The confection generally contains a base composition component and a sweetener component. Reb X or a sweetener composition comprising Reb X can serve as the sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e.g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e.g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crèmes including butter crèmes, flour pastes, whipped cream and the like; jams including strawberry jam, marmalade and the like; and breads including sweet breads and the like or other starch products, and combinations thereof.

As referred to herein, "base composition" means any composition which can be a food item and provides a matrix for carrying the sweetener component.

Suitable base compositions for embodiments of this invention may include flour, yeast, water, salt, butter, eggs, milk, milk powder, liquor, gelatin, nuts, chocolate, citric acid, tartaric acid, fumaric acid, natural flavors, artificial flavors, colorings, polyols, sorbitol, isomalt, maltitol, lactitol, malic acid, magnesium stearate, lecithin, hydrogenated glucose syrup, glycerine, natural or synthetic gum, starch, and the like, and combinations thereof. Such components generally are recognized as safe (GRAS) and/or are U.S. Food and Drug Administration (FDA)-approved. According to particular embodiments of the invention, the base composition is present in the confection in an amount ranging from about 0.1 to about 99 weight percent of the confection. Generally, the base composition is present in the confection in an amount, in combination with Reb X or a sweetener composition comprising Reb X to provide a food product.

The base composition of the confection may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the confection ranges widely depending on the particular embodiment of the confection and the desired degree of sweetness. Those of ordinary skill in the art will readily ascertain the appropriate amount of bulk sweetener.

In a particular embodiment, a confection comprises Reb X, or a sweetener composition comprising Reb X, and a base composition. Generally, the amount of Reb X in the confection ranges widely depending on the particular embodiment of the confection and the desired degree of sweetness. Those of ordinary skill in the art will readily ascertain the appropriate amount of sweetener. In a particular embodiment, Reb X is present in the confection in an amount in the range of about 30 ppm to about 6000 ppm of the confection. In another embodiment, Reb X is present in the confection in an amount in the range of about 1 ppm to about 10,000 ppm of the confection. In embodiments where the confection comprises hard candy, Reb X is present in an amount in the range of about 150 ppm to about 2250 ppm of the hard candy.

Condiment Compositions

In one embodiment, a condiment comprises Reb X. In another embodiment a condiment comprises a sweetener composition comprising Reb X. Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Generally, condiments also comprise caloric sweeteners, such as sucrose, high fructose corn syrup, molasses, honey, or brown sugar. In exemplary embodiments of the condiments provided herein, Reb X or sweetener compositions comprising Reb X is used instead of traditional caloric sweeteners. Accordingly, a condiment composition desirably comprises Reb X or a sweetener composition comprising Reb X and a condiment base.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof.

Chewing Gum Compositions

In one embodiment, a chewing gum composition comprises Reb X. In another embodiment, a chewing gum composition comprises a sweetener composition comprising Reb X. Chewing gum compositions generally comprise a water-soluble portion and a water-insoluble chewable gum base portion. The water soluble portion, which typically includes the sweetener or sweetener composition, dissipates with a portion of the flavoring agent over a period of time during chewing while the insoluble gum base portion is retained in the mouth. The insoluble gum base generally determines whether a gum is considered chewing gum, bubble gum, or a functional gum.

The insoluble gum base, which is generally present in the chewing gum composition in an amount in the range of about 15 to about 35 weight percent of the chewing gum composition, generally comprises combinations of elastomers, softeners (plasticizers), emulsifiers, resins, and fillers. Such components generally are considered food grade, recognized as safe (GRA), and/or are U.S. Food and Drug Administration (FDA)-approved.

Elastomers, the primary component of the gum base, provide the rubbery, cohesive nature to gums and can include one or more natural rubbers (e.g., smoked latex, liquid latex, or guayule); natural gums (e.g., jelutong, perillo, sorva, massaranduba balata, massaranduba chocolate, nispero, rosindinha, chicle, and gutta hang kang); or synthetic elastomers (e.g., butadiene-styrene copolymers, isobutylene-isoprene copolymers, polybutadiene, polyisobutylene, and vinyl polymeric elastomers). In a particular embodiment, the elastomer is present in the gum base in an amount in the range of about 3 to about 50 weight percent of the gum base.

Resins are used to vary the firmness of the gum base and aid in softening the elastomer component of the gum base. Non-limiting examples of suitable resins include a rosin ester, a terpene resin (e.g., a terpene resin from α-pinene, β-pinene and/or d-limonene), polyvinyl acetate, polyvinyl alcohol, ethylene vinyl acetate, and vinyl acetate-vinyl laurate copolymers. Non-limiting examples of rosin esters include a glycerol ester of a partially hydrogenated rosin, a glycerol ester of a polymerized rosin, a glycerol ester of a partially dimerized rosin, a glycerol ester of rosin, a pentaerythritol ester of a partially hydrogenated rosin, a methyl ester of rosin, or a methyl ester of a partially hydrogenated rosin. In a particular embodiment, the resin is present in the gum base in an amount in the range of about 5 to about 75 weight percent of the gum base.

Softeners, which also are known as plasticizers, are used to modify the ease of chewing and/or mouthfeel of the chewing gum composition. Generally, softeners comprise oils, fats, waxes, and emulsifiers. Non-limiting examples of oils and fats include tallow, hydrogenated tallow, large, hydrogenated or partially hydrogenated vegetable oils (e.g., soybean, canola, cottonseed, sunflower, palm, coconut, corn, safflower, or palm kernel oils), cocoa butter, glycerol monostearate, glycerol triacetate, glycerol abietate, leithin, monoglycerides, diglycerides, triglycerides acetylated monoglycerides, and free fatty acids. Non-limiting examples of waxes include polypropylene/polyethylene/Fisher-Tropsch waxes, paraffin, and microcrystalline and natural waxes (e.g., candelilla, beeswas and carnauba). Microcrystalline waxes, especially those with a high degree of crystallinity and a high melting point, also may be considered as bodying agents or textural modifiers. In a particular embodiment, the softeners are present in the gum base in an amount in the range of about 0.5 to about 25 weight percent of the gum base.

Emulsifiers are used to form a uniform dispersion of the insoluble and soluble phases of the chewing gum composition and also have plasticizing properties. Suitable emulsifiers include glycerol monostearate (GMS), lecithin (Phosphatidyl choline), polyglycerol polyricinoleic acid (PPGR), mono and diglycerides of fatty acids, glycerol distearate, tracetin, acetylated monoglyceride, glycerol triactetate, and magnesium stearate. In a particular embodiment, the emulsifiers are present in the gum base in an amount in the range of about 2 to about 30 weight percent of the gum base.

The chewing gum composition also may comprise adjuvants or fillers in either the gum base and/or the soluble portion of the chewing gum composition. Suitable adjuvants and fillers include lecithin, inulin, polydextrin, calcium carbonate, magnesium carbonate, magnesium silicate, ground limestome, aluminum hydroxide, aluminum silicate, talc, clay, alumina, titanium dioxide, and calcium phosphate. In particular embodiments, lecithin can be used as an inert filler to decrease the stickiness of the chewing gum composition. In other particular embodiments, lactic acid copolymers, proteins (e.g., gluten and/or zein) and/or guar can be used to create a gum that is more readily biodegradable. The adjuvants or fillers are generally present in the gum base in an amount up to about 20 weight percent of the gum base. Other optional ingredients include coloring agents, whiteners, preservatives, and flavors.

In particular embodiments of the chewing gum composition, the gum base comprises about 5 to about 95 weight percent of the chewing gum composition, more desirably about 15 to about 50 weight percent of the chewing gum composition, and even more desirably from about 20 to about 30 weight percent of the chewing gum composition.

The soluble portion of the chewing gum composition may optionally include other artificial or natural sweeteners, bulk sweeteners, softeners, emulsifiers, flavoring agents, coloring agents, adjuvants, fillers, functional agents (e.g., pharmaceutical agents or nutrients), or combinations thereof. Suitable examples of softeners and emulsifiers are described above.

Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the chewing gum composition in an amount in the range of about 1 to about 75 weight percent of the chewing gum composition.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

In a particular embodiment, a chewing gum composition comprises or a sweetener composition comprising Reb X and a gum base. In a particular embodiment, Reb X is present in the chewing gum composition in an amount in the range of about 1 ppm to about 10,000 ppm of the chewing gum composition.

Cereal Compositions

In one embodiment, a cereal composition comprises Reb X. In another embodiment, a cereal composition comprises a sweetener composition comprising Reb X. Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, soghums, millets, oats, rye, triticale, buchwheat, fonio, quinoa, bean, soybean, amaranth, teff, spelt, and kaniwa.

In a particular embodiment, the cereal composition comprises Reb X or a sweetener composition comprising Reb X and at least one cereal ingredient. Reb X or the sweetener composition comprising Reb X may be added to the cereal composition in a variety of ways, such as, for example, as a coating, as a frosting, as a glaze, or as a matrix blend (i.e. added as an ingredient to the cereal formulation prior to the preparation of the final cereal product).

Accordingly, in a particular embodiment, Reb X or a sweetener composition comprising Reb X is added to the cereal composition as a matrix blend. In one embodiment, Reb X or a sweetener composition comprising Reb X is blended with a hot cereal prior to cooking to provide a sweetened hot cereal product. In another embodiment, Reb X or a sweetener comprising Reb X is blended with the cereal matrix before the cereal is extruded.

In another particular embodiment, Reb X or a sweetener composition comprising Reb X is added to the cereal composition as a coating, such as, for example, by combining Reb X or a sweetener comprising Reb X with a food grade oil and applying the mixture onto the cereal. In a different embodiment, Reb X or a sweetener composition comprising Reb X and the food grade oil may be applied to the cereal separately, by applying either the oil or the sweetener first. Non-limiting examples of food grade oils for use in particular embodiments include vegetable oils such as corn oil, soybean oil, cottonseed oil, peanut oil, coconut oil, canola oil, olive oil, sesame seed oil, palm oil, palm kernel oil, and mixtures thereof. In yet another embodiment, food grade fats may be used in place of the oils, provided that the fat is melted prior to applying the fat onto the cereal.

In another embodiment, the Reb X or a sweetener composition comprising Reb X is added to the cereal composition as a glaze. Non-limiting examples of glazing agents for use in particular embodiments include corn syrup, honey syrups and honey syrup solids, maple syrups and maple syrup solids, sucrose, isomalt, polydextrose, polyols, hydrogenated starch hydrosylate, aqueous solutions thereof, and mixtures thereof.

In another such embodiment, Reb X or a sweetener composition comprising Reb X is added as a glaze by combining with a glazing agent and a food grade oil or fat and applying the mixture to the cereal. In yet another embodiment, a gum system, such as, for example, gum acacia, carboxymethyl cellulose, or algin, may be added to the glaze to provide structural support. In addition, the glaze also may include a coloring agent, and also may include a flavor.

In another embodiment, Reb X or a sweetener composition comprising Reb X is added to the cereal composition as a frosting. In one such embodiment, Reb X or a sweetener composition comprising Reb X is combined with water and a frosting agent and then applied to the cereal. Non-limiting examples of frosting agents for use in particular embodiments include maltodextrin, sucrose, starch, polyols, and mixtures thereof. The frosting also may include a food grade oil, a food grade fat, a coloring agent, and/or a flavor.

Generally, the amount of Reb X in a cereal composition varies widely depending on the particular type of cereal composition and its desired sweetness. Those of ordinary skill in the art can readily discern the appropriate amount of sweetener to put in the cereal composition. In a particular embodiment, Reb X is present in the cereal composition in an amount in the range of about 0.02 to about 1.5 weight percent of the cereal composition and the at least one additive is present in the cereal composition in an amount in the range of about 1 to about 5 weight percent of the cereal composition.

Baked Goods

In one embodiment, a baked good comprises Reb X. In another embodiment, a baked good comprises a sweetener composition comprising Reb X. Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Preferred baked goods in accordance with embodiments of this invention can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, and fat. Baked goods made in accordance with many embodiments of this invention also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon. Desirably, in accordance with particular embodiments of the invention, the flour is present in the baked goods in an amount in the range of about 15 to about 60% on a dry weight basis, more desirably from about 23 to about 48% on a dry weight basis.

The type of flour may be selected based on the desired product. Generally, the flour comprises an edible non-toxic flour that is conventionally utilized in baked goods. According to particular embodiments, the flour may be a bleached bake flour, general purpose flour, or unbleached flour. In other particular embodiments, flours also may be used that have been treated in other manners. For example, in particular embodiments flour may be enriched with additional vitamins, minerals, or proteins. Non-limiting examples of flours suitable for use in particular embodiments of the invention include wheat, corn meal, whole grain, fractions of whole grains (wheat, bran, and oatmeal), and combinations thereof. Starches or farinaceous material also may be used as the flour in particular embodiments. Common food starches generally are derived from potato, corn, wheat, barley, oat, tapioca, arrow root, and sago. Modified starches and pregelatinized starches also may be used in particular embodiments of the invention.

The type of fat or oil used in particular embodiments of the invention may comprise any edible fat, oil, or combination thereof that is suitable for baking Non-limiting examples of fats suitable for use in particular embodiments of the invention include vegetable oils, tallow, lard, marine oils, and combinations thereof. According to particular embodiments, the fats may be fractionated, partially hydrogenated, and/or interesterified. In another particular embodiment, the fat desirably comprises reduced, low calorie, or non-digestible fats, fat substitutes, or synthetic fats. In yet another particular embodiment, shortenings, fats, or mixtures of hard and soft fats also may be used. In particular embodiments, shortenings may be derived principally from triglycerides derived from vegetable sources (e.g., cotton seed oil, soybean oil, peanut oil, linseed oil, sesame oil, palm oil, palm kernel oil, rapeseed oil, safflower oil, coconut oil, corn oil, sunflower seed oil, and mixtures thereof). Synthetic or natural triglycerides of fatty acids having chain lengths from 8 to 24 carbon atoms also may be used in particular embodiments. Desirably, in accordance with particular embodiments of this invention, the fat is present in the baked good in an amount in the range of about 2 to about 35% by weight on a dry basis, more desirably from about 3 to about 29% by weight on a dry basis.

Baked goods in accordance with particular embodiments of this invention also comprise water in amounts sufficient to provide the desired consistency, enabling proper forming, machining and cutting of the baked good prior or subsequent to cooking. The total moisture content of the baked good includes any water added directly to the baked good as well as water present in separately added ingredients (e.g., flour, which generally includes about 12 to about 14% by weight moisture). Desirably, in accordance with particular embodiments of this invention, the water is present in the baked good in an amount up to about 25% by weight of the baked good.

Baked goods in accordance with particular embodiments of this invention also may comprise a number of additional conventional ingredients such as leavening agents, flavors, colors, milk, milk by-products, egg, egg by-products, cocoa, vanilla or other flavoring, as well as inclusions such as nuts, raisins, cherries, apples, apricots, peaches, other fruits, citrus peel, preservative, coconuts, flavored chips such a chocolate chips, butterscotch chips, and caramel chips, and combinations thereof. In particular embodiments, the baked goods may also comprise emulsifiers, such as lecithin and monoglycerides.

According to particular embodiments of this invention, leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

In accordance with another particular embodiment of this invention, cocoa may comprise natural or "Dutched" chocolate from which a substantial portion of the fat or cocoa butter has been expressed or removed by solvent extraction, pressing, or other means. In a particular embodiment, it may be necessary to reduce the amount of fat in a baked good comprising chocolate because of the additional fat present in cocoa butter. In particular embodiments, it may be necessary to add larger amounts of chocolate as compared to cocoa in order to provide an equivalent amount of flavoring and coloring.

Baked goods generally also comprise caloric sweeteners, such as sucrose, high fructose corn syrup, erythritol, molasses, honey, or brown sugar. In exemplary embodiments of the baked goods provided herein, the caloric sweetener is replaced partially or totally with Reb X or a sweetener composition comprising Reb X. Accordingly, in one embodiment a baked good comprises Reb X or a sweetener composition comprising Reb X in combination with a fat, water, and optionally flour. In a particular embodiment, the baked good optionally may include other natural and/or synthetic high-potency sweeteners and/or bulk sweeteners.

Dairy Products

In one embodiment, a dairy product comprises Reb X. In another embodiment, a dairy product comprises a sweetener composition comprising Reb X. Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, crème fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjölk, kajmak, kephir, viili, kumiss, airag, ice milk, casein, ayran, lassi, khoa, or combinations thereof.

Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments of this invention, the dairy products are derived from the raw milk of cows, goats, sheep, horses, donkeys, camels, water buffalo, yaks, reindeer, moose, or humans.

In particular embodiments of this invention, the processing of the dairy product from raw milk generally comprises the steps of pasteurizing, creaming, and homogenizing. Although raw milk may be consumed without pasteurization, it usually is pasteurized to destroy harmful microorganisms such as bacteria, viruses, protozoa, molds, and yeasts. Pasteurizing generally comprises heating the milk to a high temperature for a short period of time to substantially reduce the number of microorganisms, thereby reducing the risk of disease.

Creaming traditionally follows pasteurization step, and involves the separation of milk into a higher-fat cream layer and a lower-fat milk layer. Milk will separate into milk and cream layers upon standing for twelve to twenty-four hours. The cream rises to the top of the milk layer and may be skimmed and used as a separate dairy product. Alternatively, centrifuges may be used to separate the cream from the milk. The remaining milk is classified according to the fat content of the milk, non-limiting examples of which include whole, 2%, 1%, and skim milk.

After removing the desired amount of fat from the milk by creaming, milk is often homogenized. Homogenization prevents cream from separating from the milk and generally involves pumping the milk at high pressures through narrow tubes in order to break up fat globules in the milk. Pasteurization, creaming, and homogenization of milk are common but are not required to produce consumable dairy products. Accordingly, suitable dairy products for use in embodiments of this invention may undergo no processing steps, a single processing step, or combinations of the processing steps described herein. Suitable dairy products for use in embodiments of this invention may also undergo processing steps in addition to or apart from the processing steps described herein.

Particular embodiments of this invention comprise dairy products produced from milk by additional processing steps. As described above, cream may be skimmed from the top of milk or separated from the milk using machine-centrifuges. In a particular embodiment, the dairy product comprises sour cream, a dairy product rich in fats that is obtained by fermenting cream using a bacterial culture. The bacteria produce lactic acid during fermentation, which sours and thickens the cream. In another particular embodiment, the dairy product comprises crème fraiche, a heavy cream slightly soured with bacterial culture in a similar manner to sour cream. Crème fraiche ordinarily is not as thick or as sour as sour cream. In yet another particular embodiment, the dairy product comprises cultured buttermilk. Cultured buttermilk is obtained by adding bacteria to milk. The resulting fermentation, in which the bacterial culture turns lactose into lactic acid, gives cultured buttermilk a sour taste. Although it is produced in a different manner, cultured buttermilk generally is similar to traditional buttermilk, which is a by-product of butter manufacture.

According to other particular embodiments of this invention, the dairy products comprise milk powder, condensed milk, evaporated milk, or combinations thereof. Milk powder, condensed milk, and evaporated milk generally are produced by removing water from milk. In a particular embodiment, the dairy product comprises a milk powder comprising dried milk solids with a low moisture content. In another particular embodiment, the dairy product comprises condensed milk. Condensed milk generally comprises milk with a reduced water content and added sweetener, yielding a thick, sweet product with a long shelf-life. In yet another particular embodiment, the dairy product comprises evaporated milk. Evaporated milk generally comprises fresh, homogenized milk from which about 60% of the water has been removed, that has been chilled, fortified with additives such as vitamins and stabilizers, packaged, and finally sterilized. According to another particular embodiment of this invention, the dairy product comprises a dry creamer and Reb X or a Reb X sweetener composition.

In another particular embodiment, the dairy product provided herein comprises butter. Butter generally is made by churning fresh or fermented cream or milk. Butter generally comprises butterfat surrounding small droplets comprising mostly water and milk proteins. The churning process damages the membranes surrounding the microscopic globules of butterfat, allowing the milk fats to conjoin and to separate from the other parts of the cream. In yet another particular embodiment, the dairy product comprises buttermilk, which is the sour-tasting liquid remaining after producing butter from full-cream milk by the churning process.

In still another particular embodiment, the dairy product comprises cheese, a solid foodstuff produced by curdling milk using a combination of rennet or rennet substitutes and acidification. Rennet, a natural complex of enzymes produced in mammalian stomachs to digest milk, is used in cheese-making to curdle the milk, causing it to separate into solids known as curds and liquids known as whey. Generally, rennet is obtained from the stomachs of young ruminants, such as calves; however, alternative sources of rennet include some plants, microbial organisms, and genetically modified bacteria, fungus, or yeast. In addition, milk may be coagulated by adding acid, such as citric acid. Generally, a combination of rennet and/or acidification is used to curdle the milk. After separating the milk into curds and whey, some cheeses are made by simply draining, salting, and packaging the curds. For most cheeses, however, more processing is needed. Many different methods may be used to produce the hundreds of available varieties of cheese. Processing methods include heating the cheese, cutting it into small cubes to drain, salting, stretching, cheddaring, washing, molding, aging, and ripening. Some cheeses, such as the blue cheeses, have additional bacteria or molds introduced to them before or during aging, imparting flavor and aroma to the finished product. Cottage cheese is a cheese curd product with a mild flavor that is drained but not pressed so that some whey remains. The curd is usually washed to remove acidity. Cream cheese is a soft, mild-tasting, white cheese with a high fat content that is produced by adding cream to milk and then curdling to form a rich curd. Alternatively, cream cheese can be made from skim milk with cream added to the curd. It should be understood that cheese, as used herein, comprises all solid foodstuff produced by the curdling milk.

In another particular embodiment of this invention, the dairy product comprises yogurt. Yogurt generally is produced by the bacterial fermentation of milk. The fermentation of lactose produces lactic acid, which acts on proteins in milk to give the yogurt a gel-like texture and tartness. In particularly desirable embodiments, the yogurt may be sweetened with a sweetener and/or flavored. Non-limiting examples of flavorings include, but are not limited to, fruits (e.g., peach, strawberry, banana), vanilla, and chocolate. Yogurt, as used herein, also includes yogurt varieties with different consistencies and viscosities, such as dahi, dadih or dadiah, labneh or labaneh, bulgarian, kefir, and matsoni. In another particular embodiment, the dairy product comprises a yogurt-based beverage, also known as drinkable yogurt or a yogurt smoothie. In particularly desirable embodiments, the yogurt-based beverage may comprise sweeteners, flavorings, other ingredients, or combinations thereof.

Other dairy products beyond those described herein may be used in particular embodiments of this invention. Such dairy products are well known to those of ordinary skill in the art, non-limiting examples of which include milk and juice, coffee, tea, vla, piima, filmjolk, kajmak, kephir, viili, kumiss, airag, ice milk, casein, ayran, lassi, and khoa.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

In a particularly desirable embodiment, the dairy composition comprises Reb X or a sweetener composition comprising Reb X in combination with a dairy product. In a particular embodiment, Reb X is present in the dairy composition in an amount in the range of about 200 to about 20,000 weight percent of the dairy composition.

Reb X or sweetener compositions comprising Reb X are also suitable for use in processed agricultural products, livestock products or seafood; processed meat products such as sausage and the like; retort food products, pickles, preserves boiled in soy sauce, delicacies, side dishes; soups; snacks such as potato chips, cookies, or the like; as shredded filler, leaf, stem, stalk, homogenized leaf cured and animal feed.

Tabletop Sweetener Compositions

Tabletop sweetener compositions containing Reb X are also contemplated herein. The tabletop composition can further include at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop functional sweetener composition in an amount from about 0.001 to about 3% by weight of the tabletop functional sweetener composition.

The tabletop sweetener compositions can be packaged in any form known in the art. Non-limiting forms include, but are not limited to, powder form, granular form, packets, tablets, sachets, pellets, cubes, solids, and liquids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). The amount of Reb X in a dry-blend tabletop sweetener formulation can vary. In a particular embodiment, a dry-blend tabletop sweetener formulation may contain Reb X in an amount from about 1% (w/w) to about 10% (w/w) of the tabletop sweetener composition.

Solid tabletop sweetener embodiments include cubes and tablets. A non-limiting example of conventional cubes are equivalent in size to a standard cube of granulated sugar, which is approximately $2.2 \times 2.2 \times 2.2$ cm$^3$ and weigh approximately 8 g. In one embodiment, a solid tabletop sweetener is in the form of a tablet or any other form known to those skilled in the art.

A tabletop sweetener composition also may be embodied in the form of a liquid, wherein Reb X is combined with a liquid carrier. Suitable non-limiting examples of carrier agents for liquid tabletop functional sweeteners include water, alcohol, polyol, glycerin base or citric acid base dissolved in water, and mixtures thereof. The sweetness equivalent of a tabletop sweetener composition for any of the forms described herein or known in the art may be varied to obtain a desired sweetness profile. For example, a tabletop sweetener composition may comprise a sweetness comparable to that of an equivalent amount of standard sugar. In another embodiment, the tabletop sweetener composition may comprise a sweetness of up to 100 times that of an equivalent amount of sugar. In another embodiment, the tabletop sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

Beverage and Beverage Products

In one embodiment, the sweetened composition is a beverage product. As used herein a "beverage product" is a ready-to-drink beverage, a beverage concentrate, a beverage syrup, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a liquid matrix, i.e. the basic ingredient in which the ingredients—including the sweetener or sweetener compositions—are dissolved. In one embodiment, a beverage comprises water of beverage quality as the liquid matrix, such as, for example deionized water, distilled water, reverse osmosis water, carbon-treated water, purified water, demineralized water and combinations thereof, can be used. Additional suitable liquid matrices include, but are not limited to phosphoric acid, phosphate buffer, citric acid, citrate buffer and carbon-treated water.

In one embodiment, a beverage contains Reb X as the sole sweetener.

In another embodiment, a beverage contains a sweetener composition comprising Reb X. Any sweetener composition comprising Reb X detailed herein can be used in the beverages.

In another embodiment, a method of preparing a beverage comprises combining a liquid matrix and Reb X. The method can further comprise addition of one or more sweeteners, additives and/or functional ingredients.

In still another embodiment, a method of preparing a beverage comprises combining a liquid matrix and a sweetener composition comprising Reb X.

In one embodiment, a beverage contains Reb X in an amount ranging from about 1 ppm to about 10,000 ppm, such as, for example, from about 25 ppm to about 800 ppm. In another embodiment, Reb X is present in a beverage in an amount ranging from about 100 ppm to about 600 ppm. In yet other embodiments, Reb X is present in a beverage in an amount ranging from about 100 to about 200 ppm, from about 100 ppm to about 300 ppm, from about 100 ppm to about 400 ppm, or from about 100 ppm to about 500 ppm. In still another embodiment, Reb X is present in a beverage in an amount ranging from about 300 to about 700 ppm, such as, for example, from about 400 ppm to about 600 ppm. In a particular embodiment, Reb X is present in a beverage an amount of about 500 ppm.

In another embodiment, a beverage contains a sweetener composition containing Reb X, wherein Reb X is present in the beverage in an amount ranging from about 1 ppm to about 10,000 ppm, such as, for example, from about 25 ppm to about 800 ppm. In another embodiment, Reb X is present in the beverage in an amount ranging from about 100 ppm to about 600 ppm. In yet other embodiments, Reb X is present in the beverage in an amount ranging from about 100 to about 200 ppm, from about 100 ppm to about 300 ppm, from about 100 ppm to about 400 ppm, or from about 100 ppm to about 500 ppm. In still another embodiment, Reb X is present in the beverage in an amount ranging from about 300 to about 700 ppm, such as, for example, from about 400 ppm to about 600 ppm. In a particular embodiment, Reb X is present in the beverage in an amount of about 500 ppm.

The beverage can further include at least one additional sweetener. Any of the sweeteners detailed herein can be used, including natural, non-natural, or synthetic sweeteners.

In one embodiment, carbohydrate sweeteners can be present in the beverage in a concentration from about 100 ppm to about 140,000 ppm. Synthetic sweeteners may be present in the beverage in a concentration from about 0.3 ppm to about 3,500 ppm. Natural high potency sweeteners may be present in the beverage in a concentration from about 0.1 ppm to about 3,000 ppm.

The beverage can further include additives including, but are not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

In one embodiment, the polyol can be present in the beverage in a concentration from about 100 ppm to about 250,000 ppm, such as, for example, from about 5,000 ppm to about 40,000 ppm.

In another embodiment, the amino acid can be present in the beverage in a concentration from about 10 ppm to about 50,000 ppm, such as, for example, from about 1,000 ppm to about 10,000 ppm, from about 2,500 ppm to about 5,000 ppm or from about 250 ppm to about 7,500 ppm.

In still another embodiment, the nucleotide can be present in the beverage in a concentration from about 5 ppm to about 1,000 ppm.

In yet another embodiment, the organic acid additive can be present in the beverage in a concentration from about 10 ppm to about 5,000 ppm.

In yet another embodiment, the inorganic acid additive can be present in the beverage in a concentration from about 25 ppm to about 25,000 ppm.

In still another embodiment, the bitter compound can be present in the beverage in a concentration from about 25 ppm to about 25,000 ppm.

In yet another embodiment, the flavorant can be present in the beverage a concentration from about 0.1 ppm to about 4,000 ppm.

In a still further embodiment, the polymer can be present in the beverage in a concentration from about 30 ppm to about 2,000 ppm.

In another embodiment, the protein hydrosylate can be present in the beverage in a concentration from about 200 ppm to about 50,000.

In yet another embodiment, the surfactant additive can be present in the beverage in a concentration from about 30 ppm to about 2,000 ppm.

In still another embodiment, the flavonoid additive can be present in the beverage a concentration from about 0.1 ppm to about 1,000 ppm.

In yet another embodiment, the alcohol additive can be present in the beverage in a concentration from about 625 ppm to about 10,000 ppm.

In a still further embodiment, the astringent additive can be present in the beverage in a concentration from about 10 ppm to about 5,000 ppm.

The beverage can further contain one or more functional ingredients, detailed above. Functional ingredients include, but are not limited to, vitamins, minerals, antioxidants, preservatives, glucosamine, polyphenols and combinations thereof. Any suitable functional ingredient described herein can be used.

It is contemplated that the pH of the sweetened composition, such as, for example, a beverage, does not materially or adversely affect the taste of the sweetener. A non-limiting example of the pH range of the sweetenable composition may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage comprising Reb X may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of a beverage comprising Reb X may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, a beverage comprises between about 200 ppm and about 500 ppm Reb X, wherein the liquid matrix of the beverage is selected from the group consisting of water, acidified water, phosphoric acid, phosphate buffer, citric acid, citrate buffer, carbon-treated water and combinations thereof. The pH of the beverage can be from about 2.5 to about 4.2. The beverage can further include additives, such as, for example, erythritol. The beverage can further include functional ingredients, such as, for example vitamins.

In particular embodiments, a beverage comprises Reb X; a polyol selected from erythritol, maltitol, mannitol, xylitol, glycerol, sorbitol, and combinations thereof and optionally at least one additional sweetener and/or functional ingredient. In a particular embodiment, the polyol is erythritol. In one embodiment, Reb X and the polyol are present in the beverage in a weight ratio from about 1:1 to about 1:800, such as, for example, from about 1:4 to about 1:800, from about 1:20 to about 1:600, from about 1:50 to about 1:300 or from about 1:75 to about 1:150. In another embodiment, Reb X is present in the beverage in a concentration from about 1 ppm to about 10,000 ppm, such as, for example, about 500 ppm. The polyol, such as, for example, erythritol, is present in the beverage in a concentration from about 100 ppm to about 250,000 ppm, such as, for example, from about 5,000 ppm to about 40,000 ppm, from about 1,000 ppm to about 35,000 ppm.

In a particular embodiment, a beverage comprises a sweetener composition comprising Reb X and erythritol as the sweetener component of the sweetener composition. Generally, erythritol can comprise from about 0.1% to about 3.5% by weight of the sweetener component. Reb X can be present in the beverage in a concentration from about 50 ppm to about 600 ppm and erythritol can be from about 0.1% to about 3.5% by weight of the sweetener component. In a particular embodiment, the concentration of Reb X in the beverage is about 300 ppm and erythritol is 0.1% to about 3.5% by weight of the sweetener component. The pH of the beverage is preferably between about 2.5 to about 4.2.

In particular embodiments, a beverage comprises Reb X; a carbohydrate sweetener selected from sucrose, fructose, glucose, maltose and combinations thereof; and optionally at least one additional sweetener and/or functional ingredient. The Reb X can be provided as a pure compound or as part of a *Stevia* extract or steviol glycoside mixture, as described above. Reb X can be present in an amount from about 5% to about 99% by weight on a dry basis in either a steviol glycoside mixture or a *Stevia* extract. In one embodiment, Reb X and the carbohydrate are present in a sweetener composition in a weight ratio from about 0.001:14 to about 1:0.01, such as, for example, about 0.06:6. In one embodiment, Reb X is present in the beverage in a concentration from about 1 ppm to about 10,000 ppm, such as, for example, about 500 ppm. The carbohydrate, such as, for example, sucrose, is present in the beverage a concentration from about 100 ppm to about 140,000 ppm, such as, for example, from about 1,000 ppm to about 100,000 ppm, from about 5,000 ppm to about 80,000 ppm.

In particular embodiments, a beverage comprises Reb X; an amino acid selected from glycine, alanine, proline, taurine and combinations thereof; and optionally at least one additional sweetener and/or functional ingredient. In one embodiment, Reb X is present in the beverage in a concentration from about 1 ppm to about 10,000 ppm, such as, for example, about 500 ppm. The amino acid, such as, for example, glycine, can be present in the beverage in a concentration from about 10 ppm to about 50,000 ppm when present in a sweetened composition, such as, for example, from about 1,000 ppm to about 10,000 ppm, from about 2,500 ppm to about 5,000 ppm In particular embodiments, a beverage comprises Reb X; a salt selected from sodium chloride, magnesium chloride, potassium chloride, calcium chloride, phosphate salts and combinations thereof; and optionally at least one additional sweetener and/or functional ingredient. In one embodiment, Reb X is present in the beverage in a concentration from about 1 ppm to about 10,000 ppm, such as, for example, about 500 ppm. The inorganic salt, such as, for example, magnesium chloride, is present in the beverage in a concentration from about 25 ppm to about 25,000 ppm, such as, for example, from about 100 ppm to about 4,000 ppm or from about 100 ppm to about 3,000 ppm.

In another embodiment, a beverage comprises a sweetener composition comprising Reb X and Reb B as the sweetener component of the sweetener composition. The relative weight percent of Reb X and Reb B can each vary from about 1% to about 99% when dry, such as for example, about 95% Reb X/5% Reb B, about 90% Reb X/10% Reb B, about 85% Reb X/15% Reb B, about 80% Reb X/20% Reb B, about 75% Reb X/25% Reb B, about 70% Reb X/30% Reb B, about 65% Reb X/35% Reb B, about 60% Reb X/40% Reb B, about 55% Reb X/45% Reb B, about 50% Reb X/50% Reb B, about 45% Reb X/55% Reb B, about 40% Reb X/60% Reb B, about 35% Reb X/65% Reb B, about 30% Reb X/70% Reb B, about 25% Reb X/75% Reb B, about 20% Reb X/80% Reb B, about 15% Reb X/85% Reb B, about 10% Reb X/90% Reb B or about 5% Reb X/10% Reb B. In a particular embodiment, Reb B comprises from about 5% to about 40% by weight of the sweetener component, such as, for example, from about 10% to about 30% or about 15% to about 25%. In another particular embodiment, Reb X is present in the beverage in a concentration from about 50 ppm to about 600 ppm, such as, for example, from about 100 to about 400 ppm, and Reb B comprises from about 5% to about 40% by weight of the sweetener component. In another embodiment, Reb X is present in a concentration from about 50 ppm to about 600 ppm and Reb B is present in a concentration from about 10 to about 150 ppm. In a more particular embodiment, Reb X is present in a concentration of about 300 ppm and Reb B is present in a concentration from about 50 ppm to about 100 ppm. The pH of the beverage is preferably between about 2.5 to about 4.2.

In another embodiment, a beverage comprises a sweetener composition comprises Reb X and NSF-02 (available from PureCircle) as the sweetener component of the sweetener composition. The relative weight percent of Reb X and NSF-02 can each vary from about 1% to about 99%, such as for example, about 95% Reb X/5% NSF-02, about 90% Reb X/10% NSF-02, about 85% Reb X/15% NSF-02, about 80% Reb X/20% NSF-02, about 75% Reb X/25% NSF-02, about 70% Reb X/30% NSF-02, about 65% Reb X/35% NSF-02, about 60% Reb X/40% NSF-02, about 55% Reb X/45% NSF-02, about 50% Reb X/50% NSF-02, about 45% Reb X/55% NSF-02, about 40% Reb X/60% NSF-02, about 35% Reb X/65% NSF-02, about 30% Reb X/70% NSF-02, about 25% Reb X/75% NSF-02, about 20% Reb X/80% NSF-02, about 15% Reb X/85% NSF-02, about 10% Reb X/90% NSF-02 or about 5% Reb X/10% NSF-02. In a particular embodiment, NSF-02 comprises from about 5% to about 50% by weight of the sweetener component, such as, for example, from about 10% to about 40% or about 20% to about 30%. In another particular embodiment, Reb X is present in the beverage in a concentration from about 50 ppm to about 600 ppm, such as, for example, from about 100 to about 400 ppm, and NSF-02 comprises from about 5% to about 50% by weight of the sweetener component. In a more particular embodiment, Reb X is present in a concentration from about 50 ppm to about 600 ppm and NSF-02 is present in a concentration from about 10 ppm about 150 ppm. In a more particular embodiment, Reb X is present in a concentration of about 300 ppm and NSF-02 is present in a concentration from about 25 ppm to about 100 ppm. The pH of the beverage is preferably between about 2.5 to about 4.2.

In still another embodiment, a beverage comprises a sweetener composition comprises Reb X and mogroside V as the sweetener component of the sweetener composition. The relative weight percent of Reb X and mogroside V can each vary from about 1% to about 99%, such as for example, about 95% Reb X/5% mogroside V, about 90% Reb X/10% mogroside V, about 85% Reb X/15% mogroside V, about 80% Reb X/20% mogroside V, about 75% Reb X/25% mogroside V, about 70% Reb X/30% mogroside V, about 65% Reb X/35% mogroside V, about 60% Reb X/40% mogroside V, about 55% Reb X/45% mogroside V, about 50% Reb X/50% mogroside V, about 45% Reb X/55% mogroside V, about 40% Reb X/60% mogroside V, about 35% Reb X/65% mogroside V, about 30% Reb X/70% mogroside V, about 25% Reb X/75% mogroside V, about 20% Reb X/80% mogroside V, about 15% Reb X/85% mogroside V, about 10% Reb X/90% mogroside V or about 5% Reb X/10% mogroside V. In a particular embodiment, mogroside V comprises from about 5% to about 50% of the sweetener component, such as, for example, from about 10% to about 40% or about 20% to about 30%. In another particular embodiment, Reb X is present in the beverage in a concentration from about 50 ppm to about 600 ppm, such as, for example, from about 100 to about 400 ppm, and mogroside V comprises from about 5% to about 50% by weight of the sweetener component. In a more particular embodiment, Reb X is present in a concentration from about 50 ppm to about 600 ppm and mogroside V is present in a concentration from about 10 ppm about 250 ppm. In a more particular embodiment, Reb X is present in a concentration of about 300 ppm and mogroside is present in a concentration from about 100 ppm to about 200 ppm. The pH of the beverage is preferably between about 2.5 to about 4.2.

In another embodiment, a beverage comprises a sweetener composition comprises Reb X and Reb A as the sweetener component of the sweetener composition. The relative weight percent of Reb X and Reb A can each vary from about 1% to about 99%, such as for example, about 95% Reb X/5% Reb A, about 90% Reb X/10% Reb A, about 85% Reb X/15% Reb A, about 80% Reb X/20% Reb A, about 75% Reb X/25% Reb A, about 70% Reb X/30% Reb A, about 65% Reb X/35% Reb A, about 60% Reb X/40% Reb A, about 55% Reb X/45% Reb A, about 50% Reb X/50% Reb A, about 45% Reb X/55% Reb A, about 40% Reb X/60% Reb A, about 35% Reb X/65% Reb A, about 30% Reb X/70% Reb A, about 25% Reb X/75% Reb A, about 20% Reb X/80% Reb A, about 15% Reb X/85% Reb A, about 10% Reb X/90% Reb A or about 5% Reb X/10% Reb A. In a particular embodiment, Reb A comprises from about 5% to about 40% of the sweetener component, such as, for example, from about 10% to about 30% or about 15% to about 25%. In another particular embodiment, Reb X is present in the beverage in a concentration from about 50 ppm to about 600 ppm, such as, for example, from about 100 to about 400 ppm, and Reb A comprises from about 5% to about 40% by weight of the sweetener component. In another embodiment, Reb X is present in a concentration from about 50 ppm to about 600 ppm and Reb A is present in a concentration from about 10 to about 500 ppm. In a more particular embodiment, Reb X is present in a concentration of about 300 ppm and Reb A is present in a concentration from of about 100 ppm. The pH of the beverage is preferably between about 2.5 to about 4.2.

In another embodiment, a beverage comprises a sweetener composition comprising Reb X and Reb D as the sweetener component of the sweetener composition. The relative weight percent of Reb X and Reb D can each vary from about 1% to about 99%, such as for example, about 95% Reb X/5% Reb D, about 90% Reb X/10% Reb D, about 85% Reb X/15% Reb D, about 80% Reb X/20% Reb D, about 75% Reb X/25% Reb D, about 70% Reb X/30% Reb D, about 65% Reb X/35% Reb D, about 60% Reb X/40% Reb D, about 55% Reb X/45% Reb D, about 50% Reb X/50% Reb D, about 45% Reb X/55% Reb D, about 40% Reb X/60% Reb D, about 35% Reb X/65% Reb D, about 30% Reb X/70% Reb D, about 25% Reb X/75% Reb D, about 20% Reb X/80% Reb D, about 15% Reb X/85% Reb D, about 10% Reb X/90% Reb D or about 5% Reb X/10% Reb D. In a particular embodiment, Reb D comprises from about 5% to about 40% of the sweetener component, such as, for example, from about 10% to about 30% or about 15% to about 25%. In another particular embodiment, Reb X is present in the beverage in a concentration from about 50 ppm to about 600 ppm, such as, for example, from about 100 to about 400 ppm, and Reb D comprises from about 5% to about 40% by weight of the sweetener component. In another embodiment, Reb X is present in a concentration from about 50 ppm to about 600 ppm and Reb D is present in a concentration from about 10 ppm to about 500 ppm. In a more particular embodiment, Reb X is present in a concentration of about 300 ppm and Reb D is present in a concentration from of about 100 ppm. The pH of the beverage is preferably between about 2.5 to about 4.2.

In another embodiment, a beverage comprises a sweetener composition comprises Reb X, Reb A and Reb D as the sweetener component of the sweetener composition. The relative weight percent of Reb X, Reb A and Reb D can each vary from about 1% to about 99%. In a particular embodiment, Reb A and Reb D together comprise from about 5% to about 40% of the sweetener component, such as, for example, from about 10% to about 30% or about 15% to about 25%. In another particular embodiment, Reb X is present in the beverage in a concentration from about 50 ppm to about 600 ppm, such as, for example, from about 100 to about 400 ppm, and Reb A and Reb D together comprise from about 5% to about 40% by weight of the sweetener component. In another embodiment, Reb X is present in a concentration from about 50 ppm to about 600 ppm, Reb A is present in a concentration from about 10 ppm to about 500 ppm and Reb D is present in a concentration from about 10 ppm to about 500 ppm. In a more particular embodiment, Reb X is present in a concentration of about 200 ppm, Reb A is present in a concentration of about 100 ppm and Reb D is present in a concentration from of about 100 ppm. The pH of the beverage is preferably between about 2.5 to about 4.2.

In another embodiment, a beverage comprises a sweetener composition comprises Reb X, Reb B and Reb D as the sweetener component of the sweetener composition. The relative weight percent of Reb X, Reb B and Reb D can each vary from about 1% to about 99%. In a particular embodiment, Reb B and Reb D together comprise from about 5% to about 40% of the sweetener component, such as, for example, from about 10% to about 30% or about 15% to about 25%. In another particular embodiment, Reb X is present in the beverage in a concentration from about 50 ppm to about 600 ppm, such as, for example, from about 100 to about 400 ppm, and Reb B and Reb D together comprise from about 5% to about 40% by weight of the sweetener component. In another embodiment, Reb X is present in a concentration from about 50 ppm to about 600 ppm, Reb B is present in a concentration from about 10 ppm to about 500 ppm and Reb D is present in a concentration from about 10 ppm to about 500 ppm. In a more particular embodiment, Reb X is present in a concentration of about 200 ppm, Reb B is present in a concentration of about 100 ppm and Reb D is present in a concentration from of about 100 ppm. The pH of the beverage is preferably between about 2.5 to about 4.2.

Methods for Improving Temporal and/or Flavor Profile

A method for imparting a more sugar-like temporal profile, flavor profile, or both to a sweetenable composition comprises combining a sweetenable composition with Reb X or the sweetener compositions of the present invention, i.e., sweetener compositions containing Reb X.

The method can further include the addition of other sweeteners, additives, functional ingredients and combinations thereof. Any sweetener, additive or functional ingredient detailed herein can be used.

As used herein, the "sugar-like" characteristics include any characteristic similar to that of sucrose and include, but are not limited to, maximal response, flavor profile, temporal profile, adaptation behavior, mouthfeel, concentration/response function, tastant/and flavor/sweet taste interactions, spatial pattern selectivity, and temperature effects.

The flavor profile of a sweetener is a quantitative profile of the relative intensities of all of the taste attributes exhibited. Such profiles often are plotted as histograms or radar plots.

These characteristics are dimensions in which the taste of sucrose is different from the tastes of Reb X. Of these, however, the flavor profile and temporal profile are particularly important. In a single tasting of a sweet food or beverage, differences (1) in the attributes that constitute a sweetener's flavor profile and (2) in the rates of sweetness onset and dissipation, which constitute a sweetener's temporal profile, between those observed for sucrose and for Reb X can be noted.

Whether or not a characteristic is more sugar-like is determined by an expert sensory panel who taste compositions comprising sugar and compositions comprising Reb X, both with and without additives, and provide their impression as to the similarities of the characteristics of the sweetener compositions, both with and without additives, with those comprising sugar. A suitable procedure for determining whether a composition has a more sugar-like taste is described in embodiments described herein below.

In a particular embodiment, a panel of assessors is used to measure the reduction of sweetness linger. Briefly described, a panel of assessors (generally 8 to 12 individuals) is trained to evaluate sweetness perception and measure sweetness at several time points from when the sample is initially taken into the mouth until 3 minutes after it has been expectorated. Using statistical analysis, the results are compared between samples containing additives and samples that do not contain additives. A decrease in score for a time point measured after the sample has cleared the mouth indicates there has been a reduction in sweetness perception.

The panel of assessors may be trained using procedures well known to those of ordinary skill in the art. In a particular embodiment, the panel of assessors may be trained using the Spectrum™ Descriptive Analysis Method (Meilgaard et al, *Sensory Evaluation Techniques*, $3^{rd}$ edition, Chapter 11). Desirably, the focus of training should be the recognition of and the measure of the basic tastes; specifically, sweet. In order to ensure accuracy and reproducibility of results, each assessor should repeat the measure of the reduction of sweetness linger about three to about five times per sample, taking at least a five minute break between each repetition and/or sample and rinsing well with water to clear the mouth.

Generally, the method of measuring sweetness comprises taking a 10 mL sample into the mouth, holding the sample in the mouth for 5 seconds and gently swirling the sample in the mouth, rating the sweetness intensity perceived at 5 seconds, expectorating the sample (without swallowing following expectorating the sample), rinsing with one mouthful of water (e.g., vigorously moving water in mouth as if with mouth wash) and expectorating the rinse water, rating the sweetness intensity perceived immediately upon expectorating the rinse water, waiting 45 seconds and, while waiting those 45 seconds, identifying the time of maximum perceived sweetness intensity and rating the sweetness intensity at that time (moving the mouth normally and swallowing as needed), rating the sweetness intensity after another 10 seconds, rating the sweetness intensity after another 60 seconds (cumulative 120 seconds after rinse), and rating the sweetness intensity after still another 60 seconds (cumulative 180 seconds after rinse). Between samples take a 5 minute break, rinsing well with water to clear the mouth.

Delivery Systems

Reb X and sweetener compositions comprising Reb X can also be formulated into various delivery systems having improved ease of handling and rate of dissolution. Non-limiting examples of suitable delivery systems comprise sweetener compositions co-crystallized with a sugar or a polyol, agglomerated sweetener compositions, compacted sweetener compositions, dried sweetener compositions, particle sweetener compositions, spheronized sweetener compositions, granular sweetener compositions, and liquid sweetener compositions.

Co-Crystallized Sugar/Polyol and Reb X Composition

In a particular embodiment, a sweetener composition is co-crystallized with a sugar or a polyol in various ratios to prepare a substantially water soluble sweetener with substantially no dusting problems. Sugar, as used herein, generally refers to sucrose ($C_{12}H_{22}O_{11}$). Polyol, as used herein, is synonymous with sugar alcohol and generally refers to a molecule that contains more than one hydroxyl group, erythritol, maltitol, mannitol, sorbitol, lactitol, xylitol, isomalt, propylene glycol, glycerol (glycerine), threitol, galactitol, palatinose, reduce isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the sweetener composition.

In another embodiment, a process for preparing a sugar or a polyol co-crystallized Reb X sweetener composition is provided. Such methods are known to those of ordinary skill in the art, and are discussed in more detail in U.S. Pat. No. 6,214,402. According to certain embodiments, the process for preparing a sugar or a polyol co-crystallized Reb X sweetener composition may comprise the steps of preparing a supersaturated sugar or polyol syrup, adding a predetermined amount of premix comprising a desired ratio of the Reb X sweetener composition and sugar or polyol to the syrup with vigorous mechanical agitation, removing the sugar or polyol syrup mixture from heat, and quickly cooling the sugar or polyol syrup mixture with vigorous agitation during crystallization and agglomeration. During the process the Reb X sweetener composition is incorporated as an integral part of the sugar or polyol matrix, thereby preventing the sweetener composition from separating or settling out of the mixture during handling, packaging, or storing. The resulting product may be granular, free-flowing, non-caking, and may be readily and uniformly dispersed or dissolved in water.

In a particular embodiment, a sugar or a polyol syrup may be obtained commercially or by effectively mixing a sugar or a polyol with water. The sugar or polyol syrup may be supersaturated to produce a syrup with a solids content in the range of about 95 to about 98% by weight of the syrup by removing water from the sugar syrup. Generally, the water may be removed from the sugar or polyol syrup by heating and agitating the sugar or polyol syrup while maintaining the sugar or polyol syrup at a temperature of not less than about 120° C. to prevent premature crystallization.

In another particular embodiment, a dry premix is prepared by combining the Reb X sweetener composition and a sugar or a polyol in a desired amount. According to certain embodiments, the weight ratio of the Reb X sweetener composition to sugar or polyol is in the range of about 0.001:1 to about 1:1. Other components, such as flavors or other high-potency sweeteners, also may be added to the dry premix, so long as the amount does not adversely affect the overall taste of the sugar co-crystallized sweetener composition.

The amounts of premix and supersaturated syrup may be varied in order to produce products with varying levels of sweetness. In particular embodiments, the Reb X sweetener composition is present in an amount from about 0.001% to about 50% by weight of the final product, or from about 0.001% to about 5%, or from about 0.001% to about 2.5%.

The sugar or polyol co-crystallized sweetener compositions of this invention are suitable for use in any sweetenable composition to replace conventional caloric sweeteners, as well as other types of low-caloric or non-caloric sweeteners. In addition, the sugar or polyol co-crystallized sweetener composition described herein can be combined in certain embodiments with bulking agents, non-limiting examples of which include dextrose, maltodextrin, lactose, inulin, polyols, polydextrose, cellulose and cellulose derivatives. Such products may be particularly suitable for use as tabletop sweeteners.

Agglomerated Sweetener Composition

In certain embodiments, an agglomerate of a Reb X sweetener composition is provided. As used herein, "sweetener agglomerate" means a plurality of sweetener particles clustered and held together. Examples of sweetener agglomerates include, but are not limited to, binder held agglomerates, extrudates, and granules.

Binder Held Agglomerates

According to certain embodiments, a process for preparing an agglomerate of a Reb X sweetener composition, a binding agent and a carrier is provided. Methods for making agglomerates are known to those of ordinary skill in the art, and are disclosed in more detail in U.S. Pat. No. 6,180,157. Generally described, the process for preparing an agglomerate in accordance with a certain embodiment comprises the steps of preparing a premix solution comprising a Reb X sweetener composition and a binding agent in a solvent, heating the premix to a temperature sufficient to effectively form a mixture of the premix, applying the premix onto a fluidized carrier by a fluid bed agglomerator, and drying the resulting agglomerate. The sweetness level of the resulting agglomerate may be modified by varying the amount of the sweetener composition in the premix solution.

In a particular embodiment, the premix solution comprises a Reb X sweetener composition and a binding agent dissolved in a solvent. The binding agent may have sufficient binding strength to facilitate agglomeration. Non-limiting examples of suitable binding agents include maltodextrin, sucrose, gellan gum, gum arabic, hydroxypropylmethyl cellulose, carboxymethyl cellulose, polyvinyl pyrrolidone, cellobiose, proteins and mixtures thereof. The Reb X sweetener composition and binding agent may be dissolved in the same solvent or in two separate solvents. In embodiments wherein separate solvents are used to dissolve the sweetener composition and binding agent, the solvents may be the same or different before being combined into a single solution. Any solvent in which the Reb X sweetener composition and/or binding agent dissolves may be used. Desirably, the solvent is a food grade solvent, non-limiting examples of which include ethanol, water, isopropanol, methanol, and mixtures thereof. In order to effect complete mixing of the premix, the premix may be heated up to a temperature in the range of about 30 to about 100° C. As used herein, the term "effect mixing" means blending sufficiently so as to form a mixture.

The amount of binding agent in the solution may vary depending on a variety of factors, including the binding strength of the particular binding agent and the particular solvent chosen. The binding agent is generally present in the premix solution in an amount from about 1 to about 50% by weight of the premix solution, or from about 5 to about 25% by weight. The weight ratio of the binding agent to the Reb X sweetener composition in the premix solution may vary from as low as about 1:10 to as high as about 10:1. The weight ratio of the binding agent to the Reb X sweetener composition may also vary from about 0.5:1.0 to about 2:1.

Following preparation of the premix solution, the premix solution is applied onto a fluidized carrier using a fluid bed agglomeration mixer. Preferably, the premix is applied onto the fluidized carrier by spraying the premix onto the fluidized carrier to form an agglomerate of the Reb X sweetener composition and the carrier. The fluid bed agglomerator may be any suitable fluid bed agglomerator known to those of ordinary skill in the art. For example, the fluid bed agglomerator may be a batch, a continuous, or a continuous turbulent flow agglomerator.

The carrier is fluidized and its temperature is adjusted to between about 20 and about 50° C., or to between about 35 and about 45° C. In a certain embodiments, the carrier is heated to about 40° C. The carrier may be placed into a removable bowl of a fluid bed agglomerator. After the bowl is secured to the fluid bed agglomerator, the carrier is fluidized and heated as necessary by adjusting the inlet air temperature. The temperature of the inlet air can be maintained between about 50 and about 100° C. For example, to heat the fluidized carrier to about 40° C., the inlet air temperature may be adjusted to between about 70 and about 75° C.

Once the fluidized carrier reaches the desired temperature, the premix solution may be applied through the spray nozzle of the fluid bed agglomerator. The premix solution may be sprayed onto the fluidized carrier at any rate which is effective to produce an agglomerate having the desired particle size distribution. Those skilled in the art will recognize that a number of parameters may be adjusted to obtain the desired particle size distribution. After spraying is completed, the agglomerate may be allowed to dry. In certain embodiments, the agglomerate is allowed to dry until the outlet air temperature reaches about 35 to about 40° C.

The amount of the Reb X sweetener composition, carrier, and binding agent in the resulting agglomerates may be varied depending on a variety of factors, including the selection of binding agent and carrier as well as the desired sweetening potency of the agglomerate. Those of ordinary skill in the art will appreciate that the amount of Reb X sweetener composition present in the agglomerates may be controlled by varying the amount of the Reb X sweetener composition that is added to the premix solution. The amount of sweetness is particularly important when trying to match the sweetness delivered by other natural and/or synthetic sweeteners in a variety of products.

In one embodiment, the weight ratio of the carrier to the Reb X sweetener composition is between about 1:10 and about 10:1, or between about 0.5:1.0 and about 2:1. In one embodiment, the Reb X sweetener composition is present in the agglomerates in an amount in the range of about 0.1 to about 99.9% by weight, the carrier is present in the agglomerates in an amount in the range of about 50 to about 99.9% by weight, and the amount of binding agent is present in the agglomerates in an amount in the range of about 0.1 to about 15% by weight based on the total weight of the agglomerate.

In another embodiment, the amount of the Reb X sweetener composition present in the agglomerate is in the range of about 50 to about 99.9% by weight, the amount of carrier present in the agglomerate is in the range of about 75 to about 99% by weight, and the amount of binding agent present in the agglomerate is in the range of about 1 to about 7% by weight.

The particle size distribution of the agglomerates may be determined by sifting the agglomerate through screens of various sizes. The product also may be screened to produce a narrower particle size distribution, if desired. For example, a 14 mesh screen may be used to remove large particles and produce a product of especially good appearance, particles smaller than 120 mesh may be removed to obtain an agglomerate with improved flow properties, or a narrower particle size distribution may be obtained if desired for particular applications.

Those of ordinary skill in the art will appreciate that the particle size distribution of the agglomerate may be controlled by a variety of factors, including the selection of binding agent, the concentration of the binding agent in solution, the spray rate of the spray solution, the atomization air pressure, and the particular carrier used. For example, increasing the spray rate may increase the average particle size.

In certain embodiments, the agglomerates provided herein may be blended with blending agents. Blending agents, as used herein, include a broad range of ingredients commonly used in foods or beverages, including, but not limited to, those ingredients used as binding agents, carriers, bulking agents, and sweeteners. For example, the agglomerates may be used to prepare tabletop sweeteners or powdered drink mixes by dry blending the agglomerates of this invention with blending agents commonly used to prepare tabletop sweeteners or powdered drink mixes using methods well known to those of ordinary skill in the art.

Extrudates

Also provided in embodiments herein are substantially dustless and substantially free-flowing extrudates or extruded agglomerates of the Reb X sweetener composition. In accordance with certain embodiments, such particles may be formed with or without the use of binders using extrusion and spheronization processes.

"Extrudates" or "extruded sweetener composition", as used herein, refers to cylindrical, free-flowing, relatively non-dusty, mechanically strong granules of the Reb X sweetener composition. The terms "spheres" or "spheronized sweetener composition", as used herein, refer to relatively spherical, smooth, free-flowing, relatively non-dusty, mechanically strong granules. Although spheres typically have a smoother surface and may be stronger/harder than extrudates, extrudates offer a cost advantage by requiring less processing. The spheres and extrudates of this invention may be processed further, if desired, to form various other particles, such as, for example, by grinding or chopping.

In another embodiment, a process for making extrudates of the Reb X sweetener composition is provided. Such methods are known to those of ordinary skill in the art and are described in more detail in U.S. Pat. No. 6,365,216. Generally described, the process of making extrudates of a Reb X sweetener composition comprises the steps of combining the Reb X sweetener composition, a plasticizer, and optionally a binder to form a wet mass; extruding the wet mass to form extrudates; and drying the extrudates to obtain particles of the Reb X sweetener composition.

Non-limiting examples of suitable plasticizers include, but are not limited to, water, glycerol, and mixtures thereof. In accordance with certain embodiments, the plasticizer generally is present in the wet mass in an amount from about 4 to about 45% by weight, or from about 15% to about 35% by weight.

Non-limiting examples of suitable binders include, but are not limited to, polyvinylpyrollidone (PVP), maltodextrins, microcrystalline cellulose, starches, hydroxypropylmethyl cellulose (HPMC), methylcellulose, hydroxypropyl cellulose (HPC), gum arabic, gelatin, xanthan gum, and mixtures thereof. The binder is generally present in the wet mass in an amount from about 0.01% to about 45% by weight, or from about 0.5% to about 10% by weight.

In a particular embodiment, the binder may be dissolved in the plasticizer to form a binder solution that is later added to the Reb X sweetener composition and other optional ingredients. Use of the binder solution provides better distribution of the binder through the wet mass.

Other optional ingredients that may be included in the wet mass include carriers and additives. One of ordinary skill in the art should readily appreciate that the carriers and additives may comprise any typical food ingredient and also should readily discern the appropriate amount of a given food ingredient to achieve a desired flavor, taste, or functionality.

Methods of extruding the wet mass to form extrudates are well known to those of ordinary skill in the art. In a particular embodiment, a low pressure extruder fitted with a die is used to form the extrudates. The extrudates can be cut into lengths using a cutting device attached to the discharge end of the extruder to form extrudates that are substantially cylindrical in shape and may have the form of noodles or pellets. The shape and size of the extrudates may be varied depending upon the shape and size of the die openings and the use of the cutting device.

Following the extrusion of the extrudates, the extrudates are dried using methods well known to those of ordinary skill in the art. In a particular embodiment, a fluidized bed dryer is used to dry the extrudates.

Optionally, in a particular embodiment, the extrudates are formed into spheres prior to the step of drying. Spheres are formed by charging the extrudates into a marumerizer, which consists of a vertical hollow cylinder (bowl) with a horizontal rotating disc (friction plate) therein. The rotating disc surface can have a variety of textures suited for specific purposes. For example, a grid pattern may be used that corresponds to the desired particle size. The extrudates are formed into spheres by contact with the rotating disc and by collisions with the wall of the bowl and between particles. During the forming of the spheres, excess moisture may move to the surface or thixotropic behavior may be exhibited by the extrudates, requiring a slight dusting with a suitable powder to reduce the probability that the particles will stick together.

As previously described, the extrudates of the Reb X sweetener composition may be formed with or without the use of a binder. The formation of extrudates without the use of a binder is desirable due to its lower cost and improved product quality. In addition, the number of additives in the extrudates is reduced. In embodiments wherein the extrudates are formed without the use of a binder, the method of forming particles further comprises the step of heating the wet mass of the Reb X sweetener composition and plasticizer to promote the binding of the wet mass. Desirably, the wet mass is heated to a temperature from about 30 to about 90° C., or from about 40 to about 70° C. Methods of heating the wet mass, in accordance with certain embodiments, include, but are not limited to, an oven, a kneader with a heated jacket, or an extruder with mixing and heating capabilities.

Granules

In one embodiment, granulated forms of a Reb X sweetener composition are provided. As used herein, the terms "granules," "granulated forms," and "granular forms" are synonymous and refer to free-flowing, substantially non-dusty, mechanically strong agglomerates of the Reb X sweetener composition.

In another embodiment, a process for making granular forms of a Reb X sweetener composition is provided. Methods of granulation are known to those of ordinary skill in the art and are described in more detail in the PCT Publication WO 01/60842. In some embodiments, such methods include, but are not limited to, spray granulation using a wet binder with or without fluidization, powder compaction, pulverizing, extrusion, and tumble agglomeration. The preferred method of forming granules is powder compaction due to its simplicity. Also provided herein are compacted forms of the sweetener Reb X composition.

In one embodiment, the process of forming granules of the Reb X sweetener composition comprises the steps of compacting the Reb X sweetener composition to form compacts; breaking up the compacts to form granules; and optionally screening the granules to obtain granules of the Reb X sweetener composition having a desired particle size.

Methods of compacting the Reb X sweetener composition may be accomplished using any known compacting techniques. Non-limiting examples of such techniques include roller compaction, tableting, slugging, ram extrusion, plunger pressing, roller briquetting, reciprocating piston processing, die pressing and pelletting. The compacts may take any form that may be subjected to subsequent size reduction, non-limiting examples of which include flakes, chips, briquets, chunks, and pellets. Those of ordinary skill in the art will appreciate that the shape and appearance of the compacts will vary depending upon the shape and surface characteristics of the equipment used in the compacting step. Accordingly, the compacts may appear smooth, corrugated, fluted, or pillow-pocketed, or the like. In addition, the actual size and characteristics of the compacts will depend upon the type of equipment and operation parameters employed during compaction.

In a particularly desirable embodiment, the Reb X sweetener composition is compacted into flakes or chips using a roller compactor. A conventional roller compaction apparatus usually includes a hopper for feeding the sweetener composition to be compacted and a pair of counter-rotating rolls, either or both of which are fixed onto their axes with one roll optionally slightly moveable. The Reb X sweetener composition is fed to the apparatus through the hopper by gravity or a force-feed screw. The actual size of the resulting compacts will depend upon the width of the roll and scale of the equipment used. In addition, the characteristics of the compacts, such as hardness, density, and thickness will depend on factors such as pressure, roll speed, feed rate, and feed screw amps employed during the compaction process.

In a particular embodiment, the sweetener composition is deaerated prior to the step of compacting, leading to more effective compaction and the formation of stronger compacts and resultant granules. Deaeration may be accomplished through any known means, non-limiting examples of which include screw feeding, vacuum deaeration, and combinations thereof.

In another particular embodiment, a dry binder is mixed with the Reb X sweetener composition prior to compaction. The use of a dry binder may improve the strength of the granules and aid in their dispersion in liquids. Suitable dry binders include, but are not limited to, pregelatinized corn starch, microcrystalline cellulose, hydrophilic polymers (e.g., methyl cellulose, hydroxypropylmethyl cellulose, hydroxypropyl cellulose, polyvinylpyrrolidone, alginates, xanthan gum, gellan gum, and gum arabic) and mixtures thereof. In accordance with certain embodiments, the dry binder generally is present in an amount from about 0.1 to about 40% by weight based on the total weight of the mixture of the Reb X sweetener composition and dry binder.

Following the step of compacting, the compacts are broken up to form granules. Any suitable means of breaking up the compacts may be used, including milling. In one particular embodiment, the breaking up of the compacts is accomplished in a plurality of steps using a variety of opening sizes for the milling. In some embodiments, the breaking up of the compacts is accomplished in two steps: a course breaking step and a subsequent milling step. The step of breaking up the compacts reduces the number of "overs" in the granulated sweetener composition. As used herein, "overs" refers to material larger than the largest desired particle size.

The breaking up of the compacts generally results in granules of varying sizes. Accordingly, it may be desirable to screen the granules to obtain granules having a desired particle size range. Any conventional means for screening particles may be used to screen the granules, including screeners and sifters. Following screening, the "fines" optionally may be recycled through the compactor. As used herein, "fines" refers to material smaller than the smallest desired particle size.

Co-Dried Sweetener Composition

Also provided herein are co-dried Reb X sweetener compositions comprising a Reb X sweetener composition and one or more co-agents. Co-agent, as used herein, includes any ingredient which is desired to be used with and is compatible with the sweetener composition for the product being produced. One skilled in the art will appreciate that the co-agents will be selected based on one or more functionalities which are desirable for use in the product applications for which the sweetener composition will be used. A broad range of ingredients are compatible with the sweetener compositions, and can be selected for such functional properties. In one embodiment, the one or more co-agents comprise the at least one additive of the sweetener composition described herein below. In another embodiment, the one or more co-agents comprise a bulking agent, flow agent, encapsulating agent, or a mixture thereof.

In another embodiment, a method of co-drying a Reb X sweetener composition and one or more co-agents is provided. Such methods are known to those of ordinary skill in the art and are described in more detail in PCT Publication WO 02/05660. Any conventional drying equipment or technique known to those of ordinary skill in the art may be used to co-dry the Reb X sweetener composition and one or more co-agents. Suitable drying processes include, but are not limited to, spray drying, convection drying, vacuum drum drying, freeze drying, pan drying, and high speed paddle drying.

In a particularly desirable embodiment, the Reb X sweetener composition is spray dried. A solution is prepared of the Reb X sweetener composition and one or more desired co-agents. Any suitable solvent or mixture of solvents may be used to prepare the solution, depending on the solubility characteristics of the Reb X sweetener composition and one or more co-agents. In accordance with certain embodiments, suitable solvents include, but are not limited to, water, ethanol, and mixtures thereof.

In one embodiment, the solution of the Reb X sweetener composition and one or more co-agents may be heated prior to spray drying. The temperature can be selected on the basis of the dissolution properties of the dry ingredients and the desired viscosity of the spray drying feed solution.

In another embodiment, a non-reactive, non-flammable gas (e.g., carbon dioxide) may be added to the solution of the Reb X sweetener composition and one or more co-agents before atomization. The non-reactive, non-flammable gas can be added in an amount effective to lower the bulk density of the resulting spray dried product and to produce a product comprising hollow spheres.

Methods of spray drying are well known to those of ordinary skill in the art. In one embodiment, the solution of the Reb X sweetener composition and one or more co-agents is fed through a spray dryer at an air inlet temperature in the range of about 150 to about 350° C. Increasing the air inlet temperature at a constant air flow may result in a product having reduced bulk density. The air outlet temperature may range from about 70 to about 140° C., in accordance with certain embodiments. Decreasing the air outlet temperature may result in a product having a high moisture content which allows for ease of agglomeration in a fluid bed dryer to produce sweetener compositions having superior dissolution properties.

Any suitable spray drying equipment may be used to co-dry the Reb X sweetener composition and one or more co-agents. Those of ordinary skill in the art will appreciate that the equipment selection may be tailored to obtain a product having particular physical characteristics. For example, foam spray drying may be used to produce low bulk density products. Alternatively, a fluid bed may be attached to the exit of the spray dryer to produce a product having enhanced dissolution rates for use in instant products. Examples of spray dryers include, but are not limited to, co-current nozzle tower spray dryers, co-current rotary atomizer spray dryers, counter-current nozzle tower spray dryers, and mixed-flow fountain nozzle spray dryers.

The resulting co-dried Reb X sweetener compositions may be further treated or separated using techniques well known to those of ordinary skill in the art. For example, a desired particle size distribution can be obtained by using screening techniques. Alternatively, the resulting co-dried Reb X sweetener compositions may undergo further processing, such as agglomeration.

Spray drying uses liquid feeds that can be atomized (e.g., slurries, solutions, and suspensions). Alternative methods of drying may be selected depending on the type of feed. For example, freeze drying and pan drying are capable of handling not only liquid feeds, as described above, but also wet cakes and pastes. Paddle dryers, such as high speed paddle dryers, can accept slurries, suspensions, gels, and wet cakes. Vacuum drum drying methods, although primarily used with liquid feeds, have great flexibility in handling feeds having a wide range of viscosities.

The resulting co-dried Reb X sweetener compositions have surprising functionality for use in a variety of systems. Notably, the co-dried Reb X sweetener compositions are believed to have superior taste properties. In addition, co-dried Reb X sweetener compositions may have increased stability in low-moisture systems.

The present invention is further illustrated by the following example, which is not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims.

EXAMPLES

Example 1

Purification of Reb X from *Stevia rebaudiana* Bertoni Plant Leaves

Two kg of *Stevia rebaudiana* Bertoni plant leaves were dried at 45° C. to an 8.0% moisture content and ground to 10-20 mm particles. The content of different glycosides in the leaves was as follows: Stevioside—2.55%, Reb A—7.78%, Reb B—0.01%, Reb C—1.04%, Reb D—0.21%, Reb F—0.14%, Reb X—0.10% Dulcoside A—0.05%, and Steviolbioside—0.05%. The dried material was loaded into a continuous extractor and the extraction was carried out with 40.0 L of water at a pH of 6.5 at 40° C. for 160 min. The filtrate was collected and subjected to chemical treatment. Calcium oxide in the amount of 400 g was added to the filtrate to adjust the pH within the range of 8.5-9.0, and the mixture was maintained for 15 min with slow agitation. Then, the pH was adjusted to around 3.0 by adding 600 g of $FeCl_3$ and the mixture was maintained for 15 min with slow agitation. A small amount of calcium oxide was further added to adjust the pH to 8.5-9.0 and the mixture was maintained for 30 min with slow agitation. The precipitate was removed by filtration on a plate-and-frame filter press using cotton cloth as the filtration material. The slightly yellow filtrate was passed through the column, packed with cation-exchange resin Amberlite FCP22 ($H^+$) and then, through the column with anion-exchange resin Amberlite FPA53 ($OH^-$). The flow rate in both columns was maintained at SV=0.8 $hour^{-1}$. After completion both columns were washed with RO water to recover the steviol glycosides left in the columns and the filtrates were combined. The portion of combined solution containing 120 g total steviol glycosides was passed through seven columns, wherein each column was packed with specific macroporous polymeric adsorbent YWD-03 (Cangzhou Yuanwei, China). The first column with the size of ⅓ of the others acted as a "catcher column". The SV was around 1.0 $hour^{-1}$. After all extract was passed through the columns, the resin sequentially was washed with 1 volume of water, 2 volumes of 0.5% NaOH, 1 volume of water, 2 volumes of 0.5% HCl, and finally with water until the pH was 7.0. The "catcher column" was washed separately. Desorption of the adsorbed steviol glycosides was carried out with 52% ethanol at SV=1.0 $hour^{-1}$. Desorption of the first "catcher column" was carried out separately and the filtrate was not mixed with the main solution obtained from other columns. Desorption of the last column also was carried out separately. The quality of extract from different columns with specific macroporous adsorbent is shown in Table 1.

TABLE 1

| Columns | Total steviol glycosides, % |
| --- | --- |
| 1 (catcher) | 55.3 |
| 2 | 92.7 |
| 3 | 94.3 |
| 4 | 96.1 |
| 5 | 96.3 |
| 6 | 95.8 |
| 7 | 80.2 |

Eluates from second to sixth columns were combined and treated separately. The combined solution of steviol glycosides was mixed with 0.3% of activated carbon from the total volume of solution. The suspension was maintained at 25° C. for 30 min with continuous agitation. Separation of carbon was carried out on a press-filtration system. For additional decolorization the filtrate was passed through the columns packed with cation-exchange resin Amberlite FCP22 ($H^+$) followed with anion-exchange resin Amberlite FPA53 A30B ($OH^-$). The flow rate in both columns was around SV=0.5 $hour^{-1}$. The ethanol was distilled using a vacuum evaporator. The solids content in the final solution was around 15%. The concentrate was passed through the columns packed with cation-exchange resin Amberlite FCP22 ($H^+$) and anion-exchange resin Amberlite FPA53 ($OH^-$) with SV=0.5 $hour^{-1}$. After all the solution was passed through the columns, both resins were washed with RO water to recover the steviol glycosides left in the columns. The resulting refined extract was transferred to the nano-filtration device, concentrated to around 52% of solids content and spray dried to provide a highly purified mixture of steviol glycosides. The yield was 99.7 g. The mixture contained Stevioside—20.5%, Reb A—65.6%, Reb B—0.1%, Reb C—8.4%, Reb D—0.5%, Reb F—1.1%, Reb X—0.1%, Dulcoside A—0.4%, and Steviolbioside—0.4%.

The combined eluate from the last column, contained about 5.3 g of total steviol glycosides including 2.3 g Reb D and around 1.9 g Reb X (35.8% Reb X/TSG ratio). It was deionized and decolorized as discussed above and then concentrated to a 33.5% content of total solids.

The concentrate was mixed with two volumes of anhydrous methanol and maintained at 20-22° C. for 24 hours with intensive agitation.

The resulting precipitate was separated by filtration and washed with about two volumes of absolute methanol. The yield of Reb X was 1.5 g with around 80% purity.

For the further purification the precipitate was suspended in three volumes of 60% methanol and treated at 55° C. for 30 min, then cooled down to 20-22° C. and agitated for another 2 hours.

The resulting precipitate was separated by filtration and washed with about two volumes of absolute methanol and subjected to similar treatment with a mixture of methanol and water.

The yield of Reb X was 1.2 g with 97.3% purity.

Example 2

Sensory Properties of Reb X

The sensory properties of Reb X were evaluated in acidified water (pH 3.0 by phosphoric acid) at 500 mg/L concentration by 20 panelists. The results are summarized in Table 2.

TABLE 2

Evaluation of steviol glycosides at 500 ppm (pH 3.0)

| Taste attribute | Stevioside (500 ppm) | Reb A (500 ppm) | Reb D (500 ppm) | Reb X (500 ppm) | Sucrose (10,000 ppm) |
|---|---|---|---|---|---|
| Bitter taste | 20 | 20 | 3 | 0 | 0 |
| Astringent taste | 20 | 20 | 3 | 0 | 0 |
| Licorice taste | 20 | 20 | 2 | 0 | 0 |
| Sweet Aftertaste | 20 | 20 | 5 | 0 | 0 |
| Comments | | | | | |
| Quality of sweet taste | Bitter aftertaste (20 of 20) | Bitter aftertaste (20 of 20) | Clean (9 of 20) | Clean (20 of 20) | Clean (20 of 20) |
| Overall evaluation | Satisfactory (0 of 20) | Satisfactory (1 of 20) | Satisfactory (11 of 20) | Satisfactory (20 of 20) | Satisfactory (20 of 20) |

The above results clearly show that Reb X possesses superior taste profile to already known steviol glycosides.

Example 3

Structure Elucidation of Reb X

HRMS: HRMS (High Resolution Mass Spectrum) data was generated with a Waters Premier Quadrupole Time-of-Flight (Q-TOF) mass spectrometer equipped with an electrospray ionization source operated in the positive-ion mode. Samples were diluted and eluted with a gradient of 2:2:1 methanol:acetonitrile:water and introduced 50 μL via infusion using the onboard syringe pump NMR: The sample was dissolved in deuterated pyridine ($C_5D_5N$) and NMR spectra were acquired on Varian Unity Plus 600 MHz instruments using standard pulse sequences. The chemical shifts are given in δ (ppm), and coupling constants are reported in Hz.

The complete $^1H$ and $^{13}C$ NMR spectral assignments for the diterpene glycoside rebaudioside X determined on the basis of 1D ($^1H$ and $^{13}C$) and 2D (COSY, HMQC and HMBC) NMR as well as high resolution mass spectroscopic data:

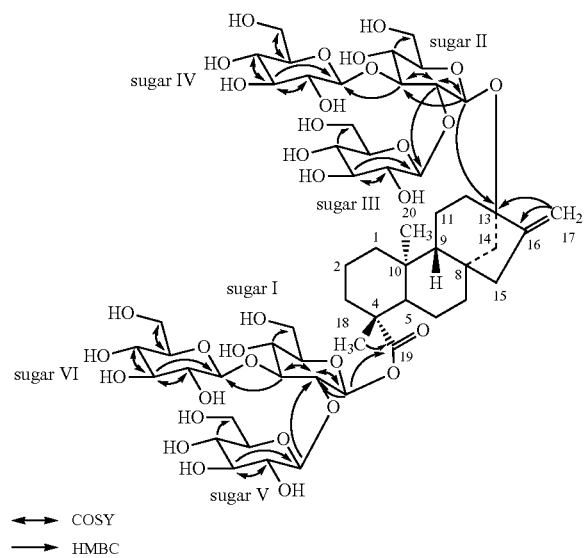

← → COSY
→ HMBC

Discussion

Figure 6A:
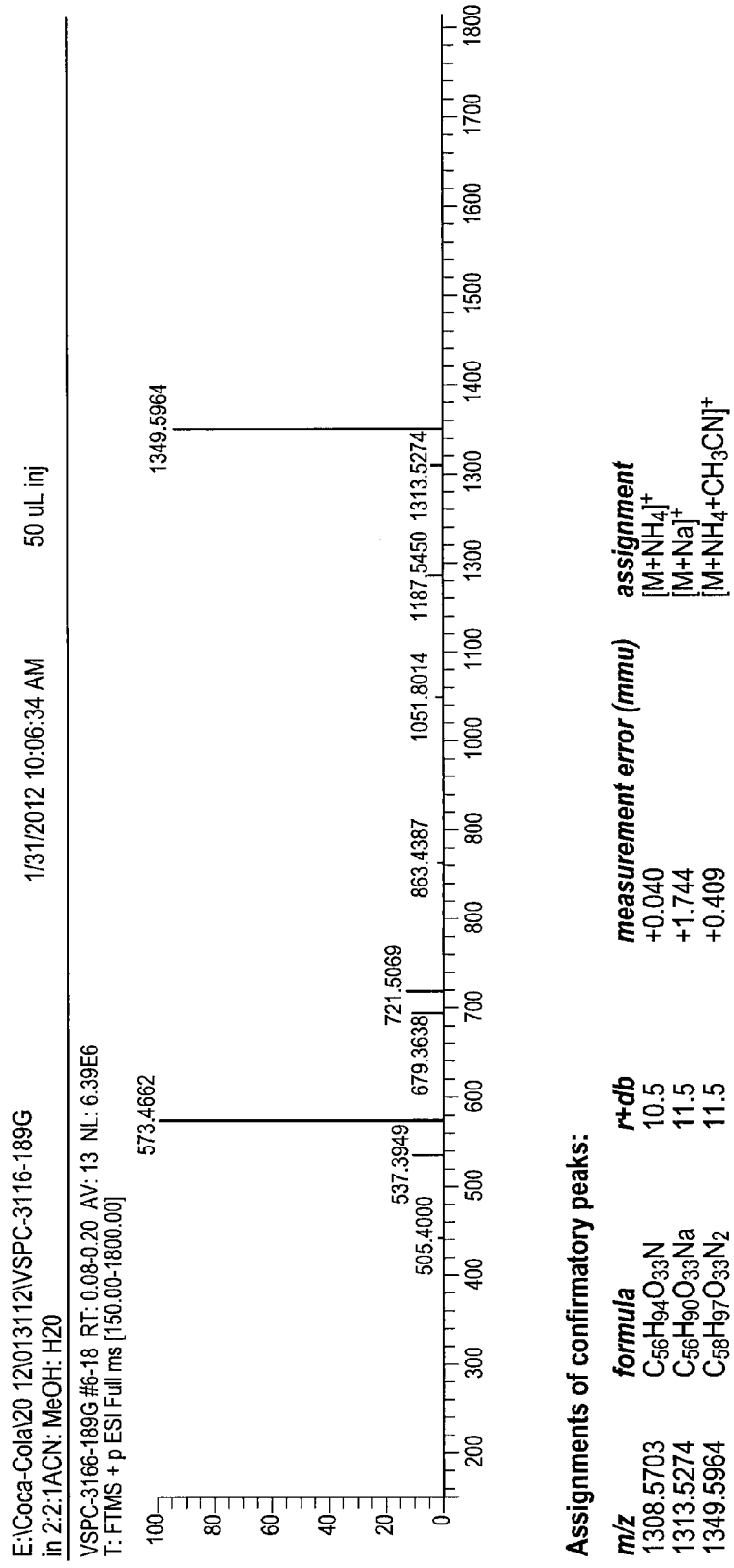
FIGS. 6a, 6b shows the high resolution spectral data for Reb X.
Figure 6B:
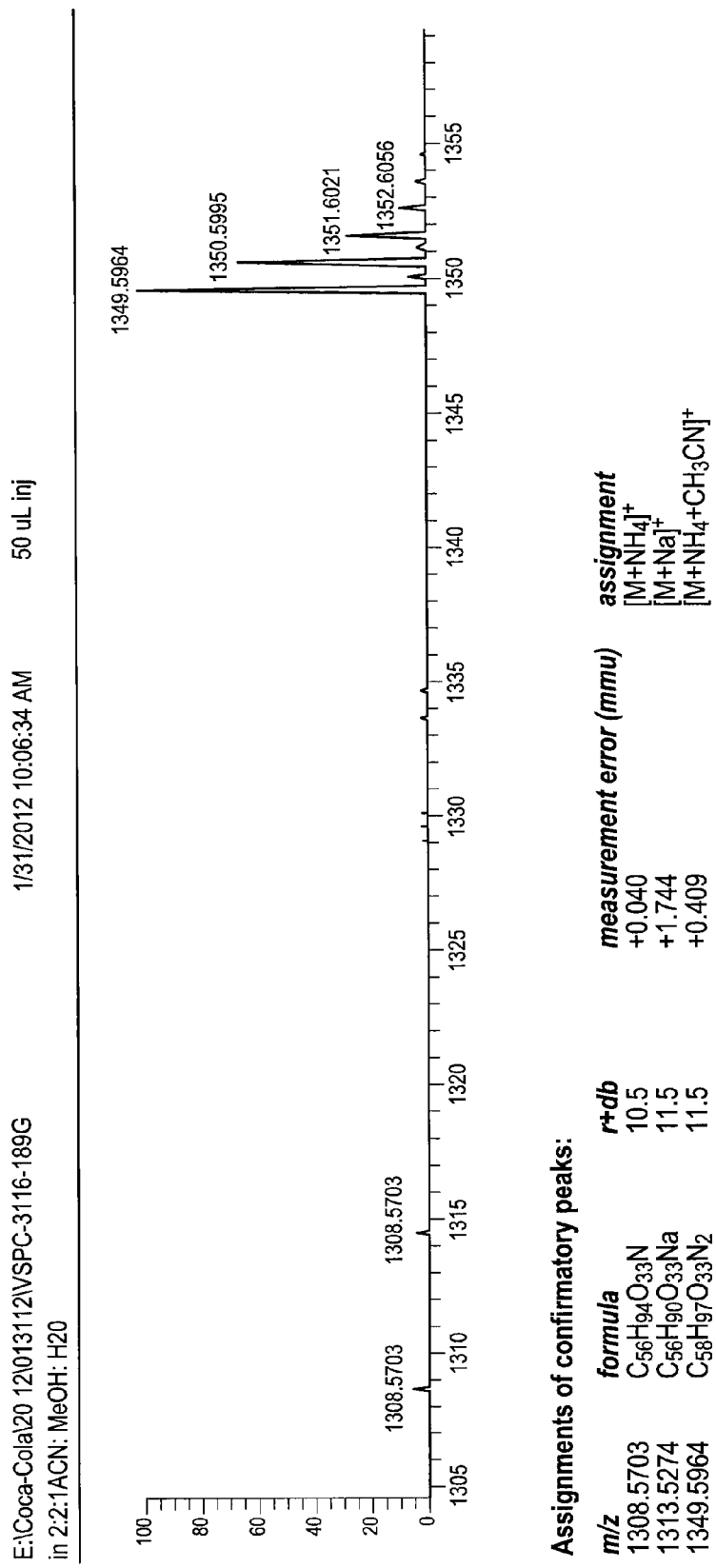
Figure 7A:
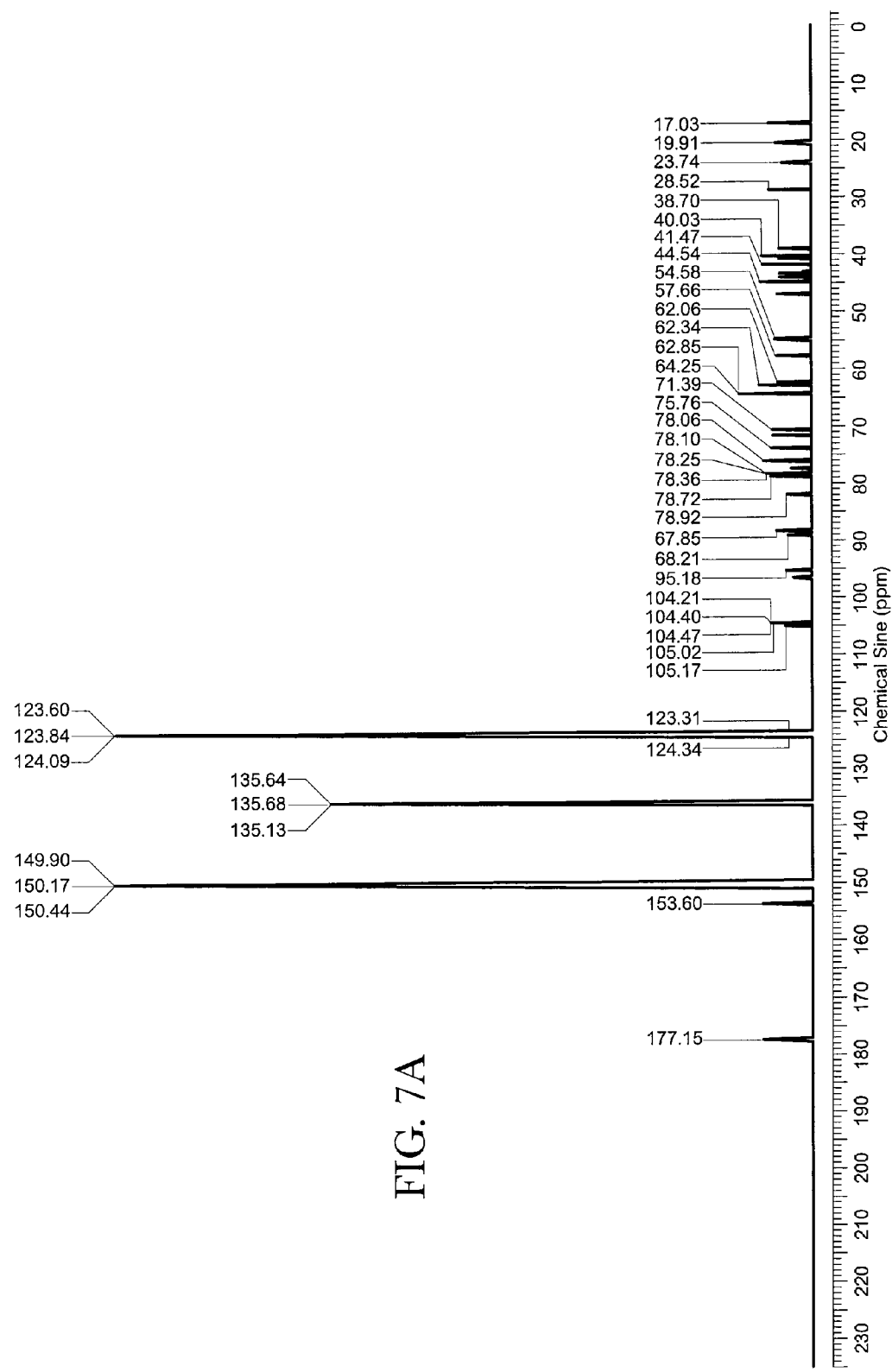
Figure 8A:
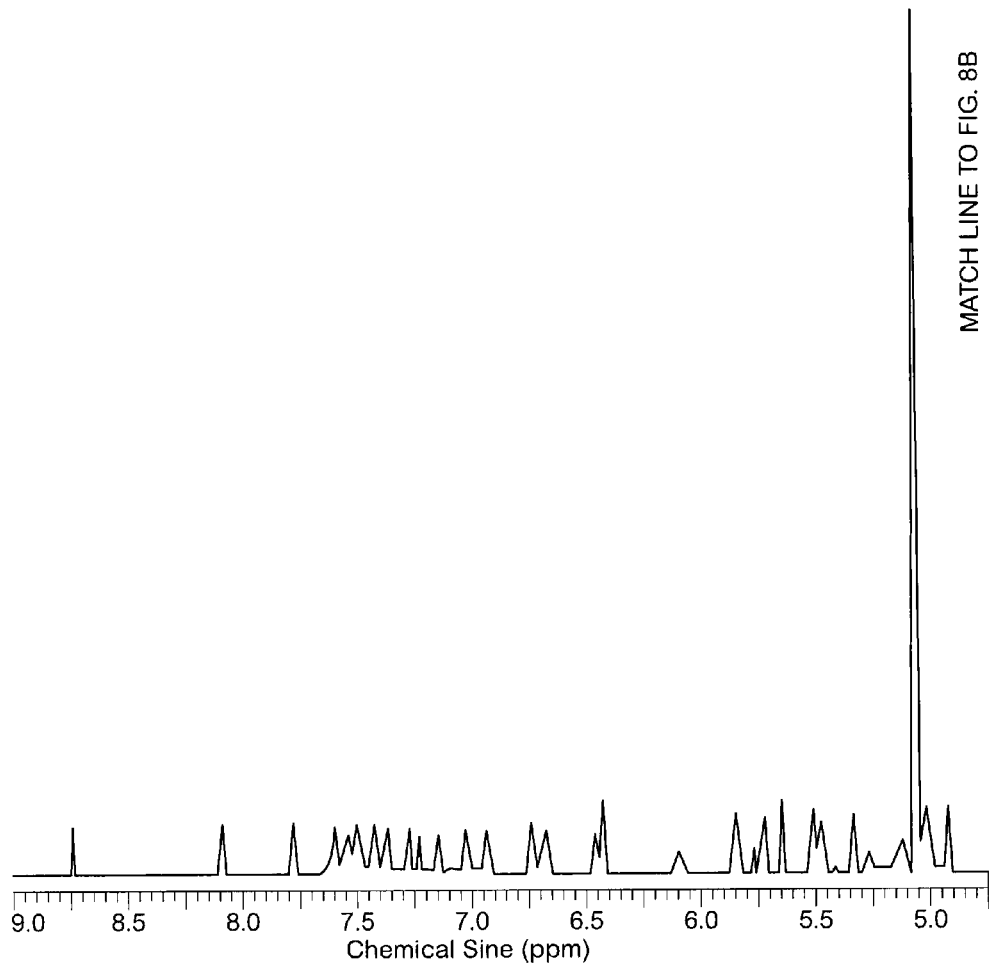
Figure 8B:
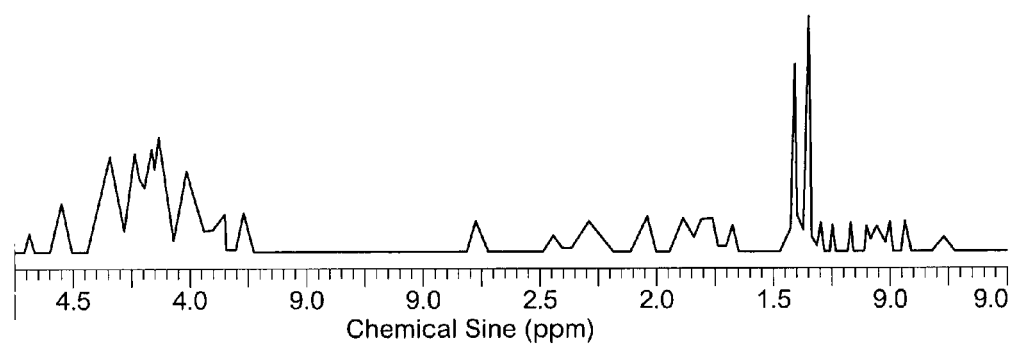

The molecular formula was deduced as $C_{56}H_{90}O_{33}$ on the basis of its positive high resolution (HR) mass spectrum (FIG. 6) which showed an $[M+NH_4^+]$ ion at m/z 1308.5703 together with an $[M+Na^+]$ adduct at m/z 1313.5274. This composition was supported by $^{13}C$ NMR spectral data (FIG. 7). The $^1H$ NMR spectrum (FIG. 8) showed the presence of two methyl singlets at δ 1.32 and 1.38, two olefinic protons as singlets at δ 4.90 and 5.69 of an exocyclic double bond, nine methylene and two methine protons between δ 0.75-2.74 characteristic for the ent-kaurane diterpenoids isolated earlier from the genus Stevia.

Figure 9:
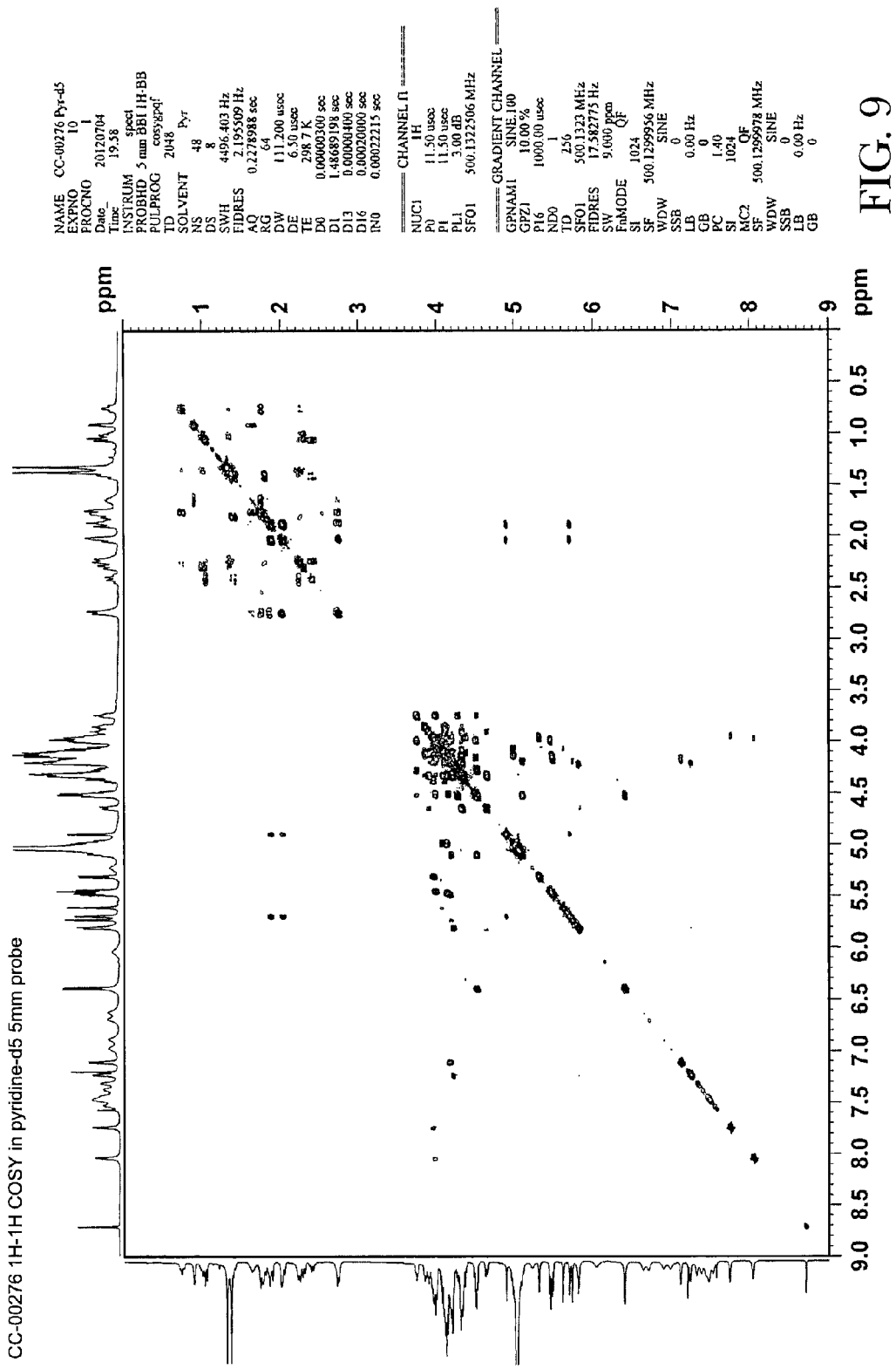
FIG. 9. shows the $^1$H—$^1$H COSY spectrum of Reb X (600 MHz, $C_5D_5N$).

The basic skeleton of ent-kaurane diterpenoids was supported by COSY (FIG. 9): H-1/H-2; H-2/H-3; H-5/H-6; H-6/H-7; H-9/H-11; H-11/H-12 correlations.

Figure 10:
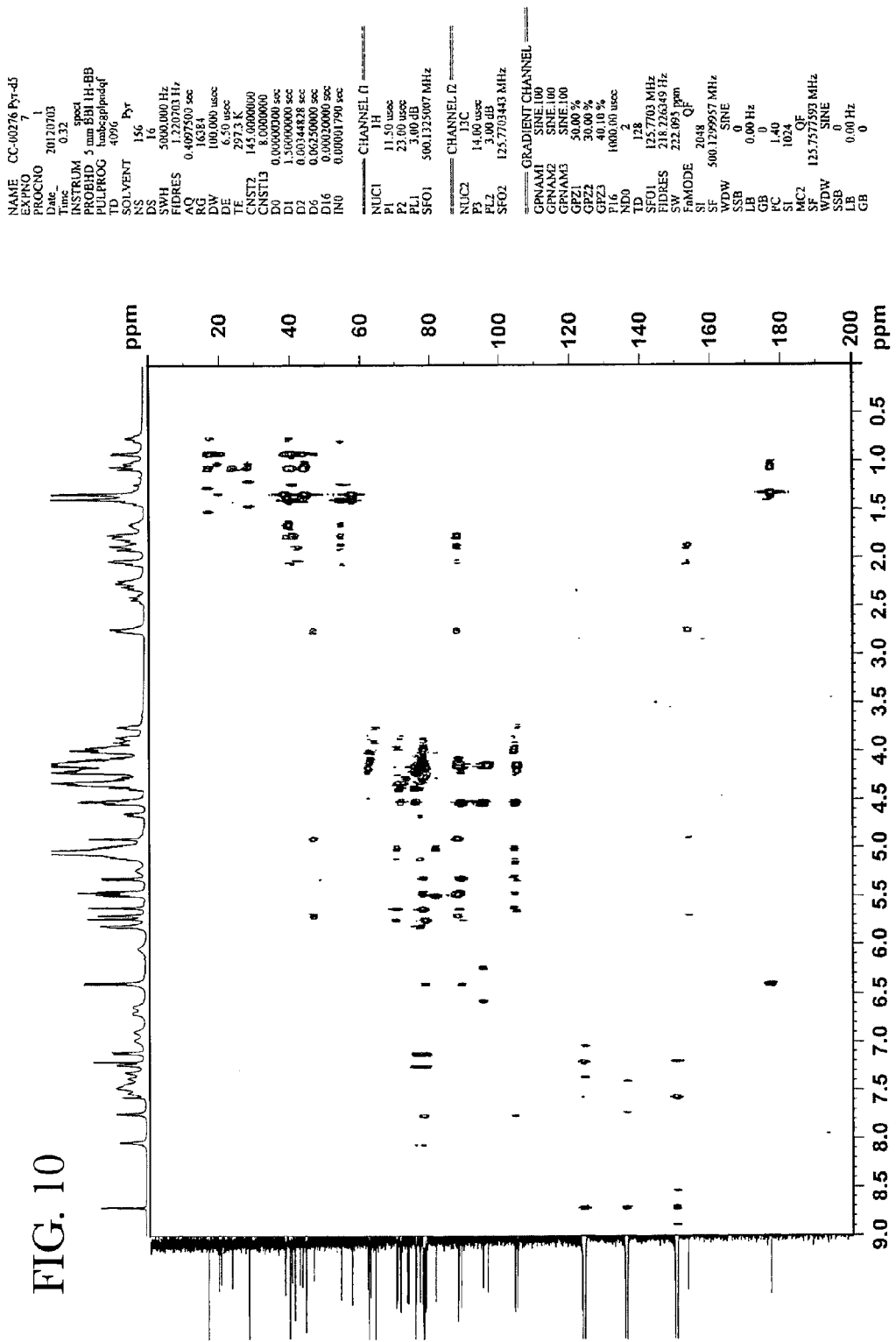
FIG. 10. shows the HMBC spectrum of Reb X (600 MHz, $C_5D_5N$).

The basic skeleton of ent-kaurane diterpenoids was also supported by HMBC (FIG. 10): H-1/C-2, C-10; H-3/C-1, C-2, C-4, C-5, C-18, C-19; H-5/C-4, C-6, C-7, C-9, C-10, C-18, C-19, C-20; H-9/C-8, C-10, C-11, C-12, C-14, C-15; H-14/C-8, C-9, C-13, C-15, C-16 and H-17/C-13, C-15, C-16 correlations.

The $^1H$ NMR spectrum also showed the presence of anomeric protons resonating at δ 5.31, 5.45, 5.46, 5.48, 5.81, and 6.39; suggesting six sugar units in its structure. Enzymatic hydrolysis furnished an aglycone which was identified as steviol by comparison of co-TLC with standard compound. Acid hydrolysis with 5% $H_2SO_4$ afforded glucose which was identified by direct comparison with authentic samples by TLC. The $^1H$ and $^{13}C$ NMR values for all protons and carbons were assigned on the basis of COSY, HMQC and HMBC correlations (Table 3).

TABLE 3

$^1H$ and $^{13}C$ NMR spectral data for Rebaudioside X in $C_5D_5N^{a-c}$.

| Position | $^{13}C$ NMR | $^1H$ NMR |
|---|---|---|
| 1 | 40.3 | 0.75 t (13.2) |
|  |  | 1.76 m |
| 2 | 19.6 | 1.35 m |
|  |  | 2.24 m |
| 3 | 38.4 | 1.01 m |
|  |  | 2.30 d (13.3) |
| 4 | 44.3 | — |
| 5 | 57.4 | 1.06 d (12.8) |
| 6 | 23.5 | 2.23 m |
|  |  | 2.41 q (13.2) |
| 7 | 42.6 | 1.41 m |
|  |  | 1.80 m |
| 8 | 41.2 | — |

TABLE 3-continued $^1$H and $^{13}$C NMR spectral data for Rebaudioside X in $C_5D_5N^{a-c}$.

| Position | $^{13}$C NMR | $^1$H NMR |
|---|---|---|
| 9 | 54.3 | 0.91 d (7.7) |
| 10 | 39.7 | — |
| 11 | 20.2 | 1.65 m |
|  |  | 1.75 m |
| 12 | 38.5 | 1.86 m |
|  |  | 2.73 m |
| 13 | 87.6 | — |
| 14 | 43.3 | 2.02 m |
|  |  | 2.74 m |
| 15 | 46.5 | 1.88 d (16.4) |
|  |  | 2.03 m |
| 16 | 153.3 | — |
| 17 | 104.9 | 4.90 s |
|  |  | 5.69 s |
| 18 | 28.2 | 1.32 s |
| 19 | 176.9 | — |
| 20 | 16.8 | 1.38 s |
| 1' | 94.9 | 6.39 d (8.2) |
| 2' | 76.9 | 4.51 t (8.5) |
| 3' | 88.6 | 5.09 t (8.5) |
| 4' | 70.1 | 4.18 m |
| 5' | 78.4 | 4.13 m |
| 6' | 61.8 | 4.20 m |
|  |  | 4.31 m |
| 1" | 96.2 | 5.46 d (7.1) |
| 2" | 81.4 | 4.13 m |
| 3" | 87.9 | 4.98 t (8.5) |
| 4" | 70.4 | 4.07 t (9.6) |
| 5" | 77.7 | 3.94 m |
| 6" | 62.6 | 4.19 m |
|  |  | 4.32 m |
| 1''' | 104.8 | 5.48 d (7.7) |
| 2''' | 75.8 | 4.15 m |
| 3''' | 78.6 | 4.13 m |
| 4''' | 73.2 | 3.98 m |
| 5''' | 77.6 | 3.74 ddd (2.8, 6.4, 9.9) |
| 6''' | 64.0 | 4.27 m |
|  |  | 4.51 m |
| 1'''' | 103.9 | 5.45 d (7.5) |
| 2'''' | 75.6 | 3.98 m |
| 3'''' | 77.8 | 4.50 t (7.8) |
| 4'''' | 71.3 | 4.14 m |
| 5'''' | 78.0 | 3.99 m |
| 6'''' | 62.1 | 4.20 m |
|  |  | 4.32 m |
| 1''''' | 104.2 | 5.81 d (7.2) |
| 2''''' | 75.5 | 4.20 m |
| 3''''' | 78.4 | 4.20 m |
| 4''''' | 73.6 | 4.10 m |
| 5''''' | 77.8 | 3.90 ddd (2.8, 6.4, 9.9) |
| 6''''' | 64.0 | 4.32 m |
|  |  | 4.64 d (10.3) |
| 1'''''' | 104.1 | 5.31 d (8.0) |
| 2'''''' | 75.5 | 3.95 m |
| 3'''''' | 78.0 | 4.37 t (9.1) |
| 4'''''' | 71.1 | 4.10 m |
| 5'''''' | 78.1 | 3.85 ddd (1.7, 6.1, 9.9) |
| 6'''''' | 62.1 | 4.10 m |
|  |  | 4.32 m |

$^a$assignments made on the basis of COSY, HMQC and HMBC correlations;
$^b$Chemical shift values are in δ (ppm);
$^c$Coupling constants are in Hz.

Based on the results from NMR spectral data, it was concluded that there are six glucosyl units. A close comparison of the $^1$H and $^{13}$C NMR spectrum of Reb X with rebaudioside D suggested that Reb X was also a steviol glycoside which had three glucose residues that attached at the C-13 hydroxyl as a 2,3-branched glucotriosyl substituent and another 2,3-branched glucotriosyl moiety in the form of an ester at C-19.

The key COSY and HMBC correlations suggested the placement of the sixth glucosyl moiety at the C-3 position of Sugar I. The large coupling constants observed for the six anomeric protons of the glucose moieties at δ 5.31 (d, J=8.0 Hz), 5.45 (d, J=7.5 Hz), 5.46 (d, J=7.1 Hz), 5.48 (d, J=7.7 Hz), 5.81 (d, J=7.2 Hz), and 6.39 (d, J=8.2 Hz), suggested their β-orientation as reported for steviol glycosides. Based on the results of NMR and mass spectral studies and in comparison with the spectral values of rebaudioside A and rebaudioside D, Reb X was assigned as 13-[(2-O-β-D-glucopyranosyl-3-O-β-D-glucopyranosyl-β-D-glucopyranosyl)oxy]ent kaur-16-en-19-oic acid-[(2-O-β-D-glucopyranosyl-3-O-β-D-glucopyranosyl-β-D-glucopyranosyl)ester].

Example 4

Taste Evaluation of Rebaudioside X

The taste properties of a sample of Reb X were studied against Rebaudioside A (Reb A) and Rebaudioside D (Reb D) samples. Reb A was obtained from Cargill (lot #1040) and Reb-D was obtained from PureCircle (lot #Nov. 3, 2008).

The samples were prepared at 500 ppm for sweetness evaluation by adding moisture compensated mass into a 100 mL sample of carbon-treated water and citric buffer solutions.

Citric buffer was prepared by mixing 1.171 g/L citric acid, 0.275 g/L sodium citrate and 0.185 g/L sodium benzoate with carbon-treated water, with a final pH of 3.22. The mixtures were moderately stirred at room temperature. The Reb X sample was then evaluated against the two control Reb A and Reb D samples in water and citric buffer at room temperature (RT) and at 4° C. in an ice bath by one experienced panelist for any tasting quality determinations using the controlled, multi-sip and swallow taste method shown below:

1. Take first sip (~1.8 mL) of control and swallow. Wait for 15-25 sec, then take second sip of control and wait for 15-25 sec.
2. Take first sip of the experimental sample, wait for 15-25 sec, then take second sip. Compare to second sip of control.
3. Repeat steps #1 and #2 for the third and fourth sips of the control and experimental samples to confirm the initial finding.

Discussion:

The taste evaluation results of the Reb X samples against the control Reb A and Reb D samples at 500 ppm in citric buffer (CB) at 4° C. and RT are described in Table 4.

TABLE 4

| Sample | Taste Properties |
|---|---|
| Reb A (room temperature) | Delayed sweetness onset, significant lingering sweet aftertaste, licorice and bitter off-notes. |
| Reb X (room temperature) | Clean sweet taste. Broad and full sweetness profile. Moderate sweetness linger aftertaste similar to aspartame. No bitter or licorice off-notes. Much better temporal profile than Reb A or Reb D. Smooth and broad sweetness temporal profile and quality similar to sucrose |
| Reb D (room temperature) | Delayed sweetness onset, less sweetness linger as compared to Reb A, no bitter off-notes. |
| Reb A (4° C.) | Similar taste quality as Reb A at room but significantly more sweet |
| Reb X (4° C.) | Similar taste quality as Reb X at room temperature |
| Reb D (4° C.) | Similar taste quality as Reb D at room but significantly more sweet |

The taste quality of Reb X at room temperature and 4° C. was similar. The taste quality of Reb X was much better than Reb A or Reb D. The Reb X did not display a pure sugar-like tasting quality but rather contained a fatty-like or broader sweet temporal profile and less sweetness linger than that of Reb A. Similar to Reb D, Reb X did not have the astringency or sweetness intense (depth) and bitterness notes compared to that of the Reb A in citrate buffer system.

Example 5

Solubility Studies of Reb X in Carbon-Treated Water and Citrate Buffer

The samples used to evaluate the taste properties in Example 2 were also used for solubility studies. At 500 ppm concentrations in citrate buffer, the initial solubility test revealed that Reb X has a similar, limited but significantly greater solubility than that of Reb D and significantly less solubility than Reb A.

Further solubility tests revealed the detailed data of concentration and time to solubilize, as shown in Table 5:

TABLE 5

| Reb X concentration in matrix system | Estimated time to solubilize (minutes) |
|---|---|
| 0.01% in carbon-treated water | 15 |
| 0.02% in carbon-treated water | 25 |
| 0.04% in carbon-treated water | 33 |
| 0.05% in carbon-treated water | 39 |
| 0.075% in carbon-treated water | 55 |
| 0.10% in carbon-treated water | 106 |
| 0.15% in carbon-treated water | Insoluble after 20 hours |
| 0.01% in citrate buffer | 25 |
| 0.02% in citrate buffer | 25 |
| 0.04% in citrate buffer | 35 |
| 0.05% in citrate buffer | 42 |
| 0.075% in citrate buffer | 55 |
| 0.10% in citrate buffer | 106 |
| 0.15% in citrate buffer | Insoluble after 20 hours |

Example 6

Isosweetness Determination of Reb X

The isosweetness levels of Reb X in a citric buffer system at room temperature and 4° C. were evaluated. A 600 ppm stock solution of Reb X was prepared by adding a mass of 0.15 g into a 250 mL sample of citric buffer (CB) solution. The mixture was moderately stirred at warmer temperature (up to ca. 52° C.) on a heated stirrer for about 15-20 minutes and then cooled. The citric buffer was prepared by adding 1.6 g citric acid, 0.6 g potassium citrate and 0.253 g sodium benzoate in 1 L of carbon-treated water. The pH of the mixture was 3.1. Seven diluted Reb X solutions at 12.5, 25, 50, 100, 200, 300, 400 and 500 ppm were prepared by adding a 2.08, 4.17, 8.33, 16.67, 25.00, 33.33 and 41.67 mL Reb X stock solution, respectively, into each 50 mL solution of CB. The controls of 0.75%, 2%, 4%, 6%, 8%, 10% and 15% sucrose equivalence (SE) were also prepared by adding sugar (w/v) into the CB. The mixtures were moderately stirred and then ready for the isosweetness determination test. The Reb X samples were then evaluated against the control sugar samples in citric buffer at room temperature (RT) and 4° C. (in an ice bath) by one experienced taster for an isosweetness determination using the controlled, multi-sip and swallow taste method. The results are shown in Table 6.

TABLE 6

| Reb X Concentration (ppm) | Estimated % Sweetness Equivalence in Citric Buffer at RT | Estimated % Sweetness Equivalence in Citric Buffer at 4° C. |
|---|---|---|
| 12.5 | 0.5 | 0.75 |
| 25 | 1.0-1.5 | 1.5 |
| 50 | 3.25-3.75 | 3.0-3.5 |
| 100 | 5.0 | 5.5 |
| 200 | 8.0 | 8.0 |
| 300 | 12.0 | 11.0-12.0 |
| 400 | 14.0-14.5 | 14.0-14.5 |
| 500 | 15.5-16.0 | 15.5-16.0 |
| 600 | 16.5-17.0 | 16.5-17.0 |

Discussion

The Reb X sample at 0.06% (w/v) was found to be very soluble and clear (colorless) in citric buffer at up to 52° C. for ca. 15-20 minutes. No off-flavors at any Reb X concentrations in CB at 4° C. were detected, except at least ca. 300 ppm which noticeably had a longer sweetness lingering. At all concentrations a pleasant sweetness tasting quality with a slight delay of sweetness onset and no bitterness was detected. Despite the stronger mouthfeel or texture effect (syrupy, thicker) at ca.15% sucrose, it was difficult to determine the isosweetness levels for at least 400 ppm of Reb X due to its thinner mouthfeel but broader and more impact sweetness temporal profile as well as its significant sweet lingering.

There was no significant sweetness intensity difference between RT and 4° C. of the Reb X concentration range based on direct comparison with control sucrose at similar temperatures. Two repeated tests comparing 50, 100, 200, 300, 400 and 500 ppm Reb X concentrations at RT and 4° C. confirmed these initial results.

Example 7

Beverage Formulations

Flavored Black Tea:
The taste properties of a flavored zero calorie black tea drink containing Reb A in a concentration of 250 ppm was compared to a comparable flavored zero calorie black tea drink with Reb X in a concentration of 250 ppm. The drink containing Reb X was determined to be much cleaner in finish with less sweetness linger and a more rounded overall sweetness profile.

Enhanced Water:
The taste properties of a zero calorie enhanced water drink containing Reb A in a concentration of 200 ppm was compared to a comparable zero calorie enhanced water drink containing Reb X in a concentration of 200 ppm. The Reb X-containing drink was cleaner in finish and had reduced sweetness linger and a more rounded overall sweetness taste quality.

Orange-Flavored Sparking Beverage:
Reb X levels were evaluated in a zero calorie orange-flavored sparking beverage base to determine the effect of increasing sweetness. Samples of the orange-flavored sparkling beverage with Reb X in amounts between 400 and 750 ppm (in 50 ppm increments) were prepared. All samples tasted significantly better than comparable Reb A-containing formulations resulting in cleaner profiles with increased sweetness intensity and no negative aftertaste characteristic. Samples having 500 ppm and 550 ppm Reb X were found to be the closest in sweetness level to a 11.5 Brix high fructose corn syrup sweetened orange flavored sparkling beverage formulation.

Example 8

Reb X Sweetness vs. Concentration 2.5%, 5.0%, 7.5%, and 10.0% sucrose solutions were prepared in neutral (7.0 pH) and acidified water (3.2 pH) as reference samples. Solutions containing Reb X (98% purity) were prepared to match the sweetness of each sucrose reference in neutral and acidified water. Samples were tasted and verified by a panel of trained tasters in water at room temperature.

TABLE 7

|  | Sweetness Equivalent (SE) | | | |
| --- | --- | --- | --- | --- |
|  | 2.5% | 5.0% | 7.5% | 10.0% |
| Reb X Concentration (ppm) | 48 | 132 | 254 | 422 |
| Sweetness Factor (SF) | 521 | 380 | 295 | 237 |

Example 9

Sensory Comparison of Reb X and Reb A

To compare the sensory attributes between Reb X and Reb A, iso-sweet samples having 8% sucrose equivalent sweetness were made with filtered water as shown in Table 8. An 8% sugar solution in water at room temperature was used as a control.

TABLE 8

| Ingredient | Reb A Formulation (weight percent of ingredient) | Reb X Formulation (weight percent of ingredient) |
| --- | --- | --- |
| Water | 99.95 | 99.95 |
| Reb A (97% on a dry basis) | 0.0510 | 0 |
| Reb X (98% on a dry basis) | 0 | 0.0423 |
| Total | 100% | 100% |

Acidified solutions of 250 ppm citric acid (pH 3.2) containing the same concentration of Reb X and Reb A as indicated in Table 8 were also prepared. An 8% sugar solution in the acidified solution was used as the control.

The samples prepared with filtered water were evaluated by 34 semi-trained panel members at room temperature. The samples prepared with acidified water were evaluated by 23 semi-trained panel members at room temperature. Samples were given to the panel members sequentially and coded with triple digit numbers. The order of sample presentation was randomized to avoid order of presentation bias. Water and unsalted crackers were provided in order to cleanse the palate. The panel members were asked to rate different attributes including sweetness onset, total sweetness, rounded sweetness, bitterness, acidity, leafy note, licorice, astringency, mouthfeel, mouth coating, sweet lingering, and bitter lingering. Samples were rated on a scale of zero (0) to ten (10), with zero indicating immediate onset, no intensity, watery/low viscosity, or very sharp peak, and ten indicating very delayed onset, high intensity, thick/high viscosity, or very round peak.

Figure 11:
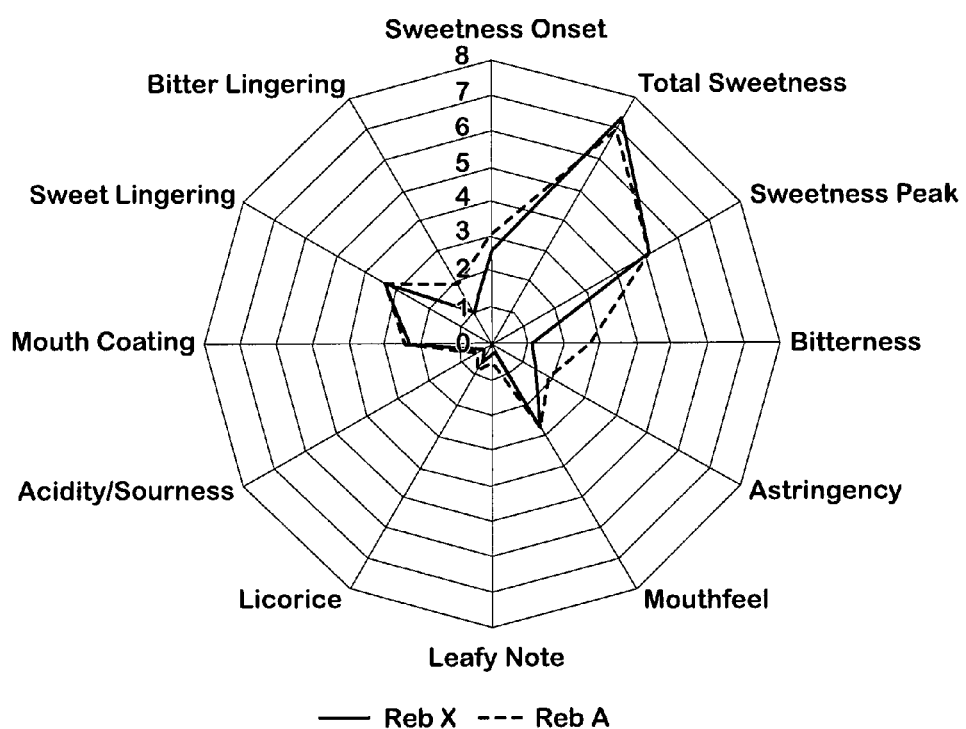
FIG. 11. shows a sensory comparison of Reb X and Reb A in filtered water.
Figure 12:
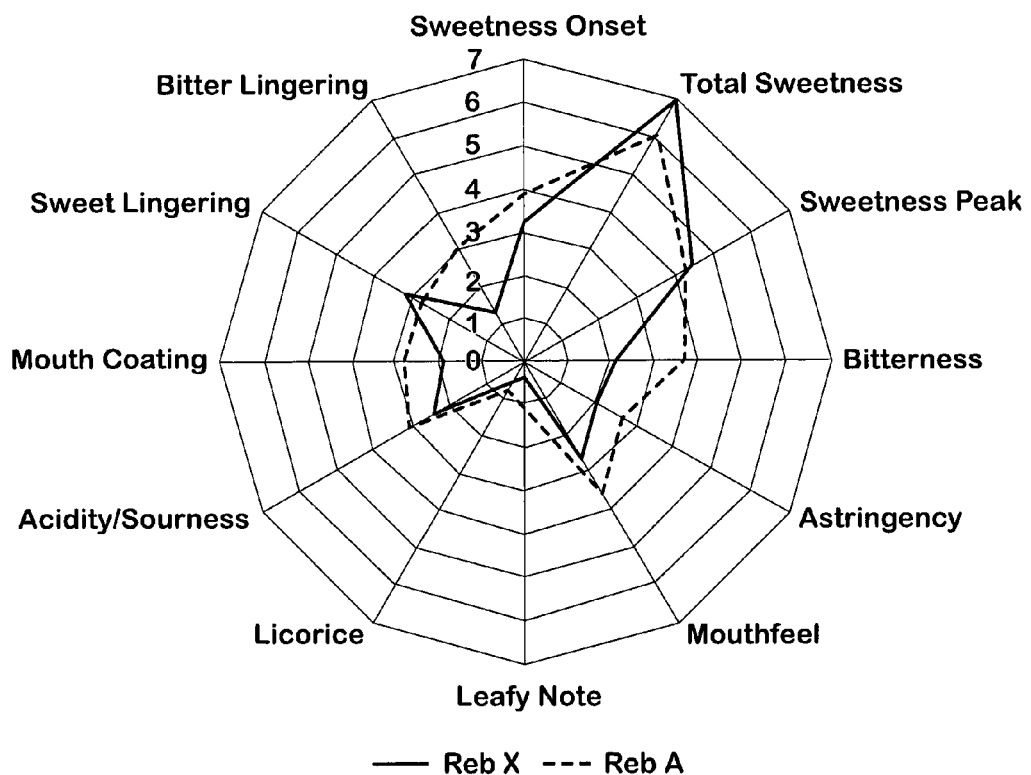
FIG. 12. shows a sensory comparison of Reb X and Reb A in acidified water.
Figure 13:
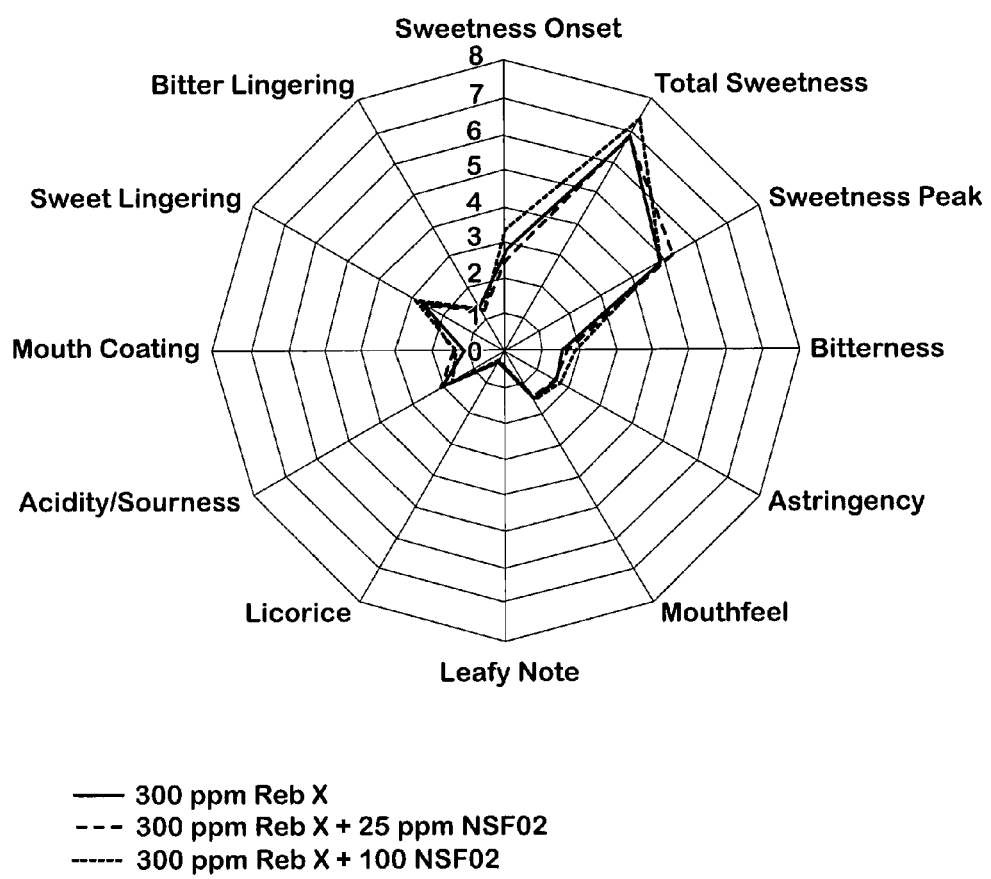
FIG. 13. shows a sensory comparison of Reb X and NSF-02 at various concentrations in acidified water.

One-way single factor ANOVA was used to analyze sensory results, where $\alpha=0.05$. The results are shown in FIGS. 11 and 12.

Discussion

Although Reb A and Reb X exhibited similar sweetness intensity, the filtered water samples (FIG. 11) showed reduced perception of bitterness, astringency and bitter lingering compared to Reb A. In acidified water, the perception of higher sweetness of Reb X over Reb A is significant (FIG. 12). Reb X also showed faster sweetness onset, reduced non-sweet taste (bitterness, sour, astringency) and bitterness lingering.

Example 10

Sensory Comparison of Reb X and Other Non-Caloric Sweeteners

Blends of Reb X and One Other Non-Caloric Sweetener

To study the interaction between Reb X and other natural ingredients, Reb X was blended with Reb B, Reb D, Reb A, NSF-02 (PureCirle), Mogroside V (Mog), and erythritol at various concentrations (Table 9) in acidified water and sensory evaluations were performed. The main objective of this study was to evaluate the improvement in the sweetness profile, including sweetness intensity in presence of other co-ingredient/sweetener.

TABLE 9

| Sample | RebX (ppm) | RebB (ppm) | RebD (ppm) | RebA (ppm) | Mog (ppm) | NSF02 (ppm) | Erythritol (%) |
| --- | --- | --- | --- | --- | --- | --- | --- |
| 1 | 300 | | | | | | |
| 2 | 300 | 100 | | | | | |
| 3 | 300 | 50 | | | | | |
| 4 | 300 | 50 | 50 | | | | |
| 5 | 300 | | 100 | | | | |
| 6 | 200 | | 100 | 100 | | | |
| 7 | | | | | | | |
| 8 | 200 | | | | 200 | | |
| 9 | 300 | | | | 100 | | |
| 10 | 300 | | | | | 25 | |
| 11 | 300 | | | | | 100 | |
| 12 | 300 | | | | | | 1% |
| 13 | 300 | | | | | | 2% |

The sweetened samples containing Reb X and Reb B were evaluated by 13 semi-trained panel members at room temperature. The sweetened samples containing Reb X and NSF-02 were evaluated by 11 semi-trained panel members at room temperature. The sweetened samples containing Reb X and mogroside V were evaluated by 9 semi-trained panel members at room temperature. The sweetened samples containing Reb X and erythritol were evaluated by 12 semi-trained panel members at room temperature. In all cases, samples were given to the panel members sequentially and coded with triple digit numbers. The order of sample presentation was randomized to avoid order of presentation bias. Water and unsalted crackers were provided in order to cleanse the palate. The panel members were asked to rate different attributes including sweetness onset, total sweetness, rounded sweetness, bitterness, acidity, leafy note, licorice, mouthfeel, mouth coating, sweet lingering, and bitter lingering. Samples were rated on a scale of zero (0) to ten (10), with zero indicating immediate onset, no intensity, watery/low viscosity, or very sharp peak, and ten indicating very delayed onset, high intensity, thick/high viscosity, or very round peak. One-way single factor ANOVA was used to analyze sensory results, where α=0.05. The results are shown in FIGS. 13-16.

Discussion

Figure 14:
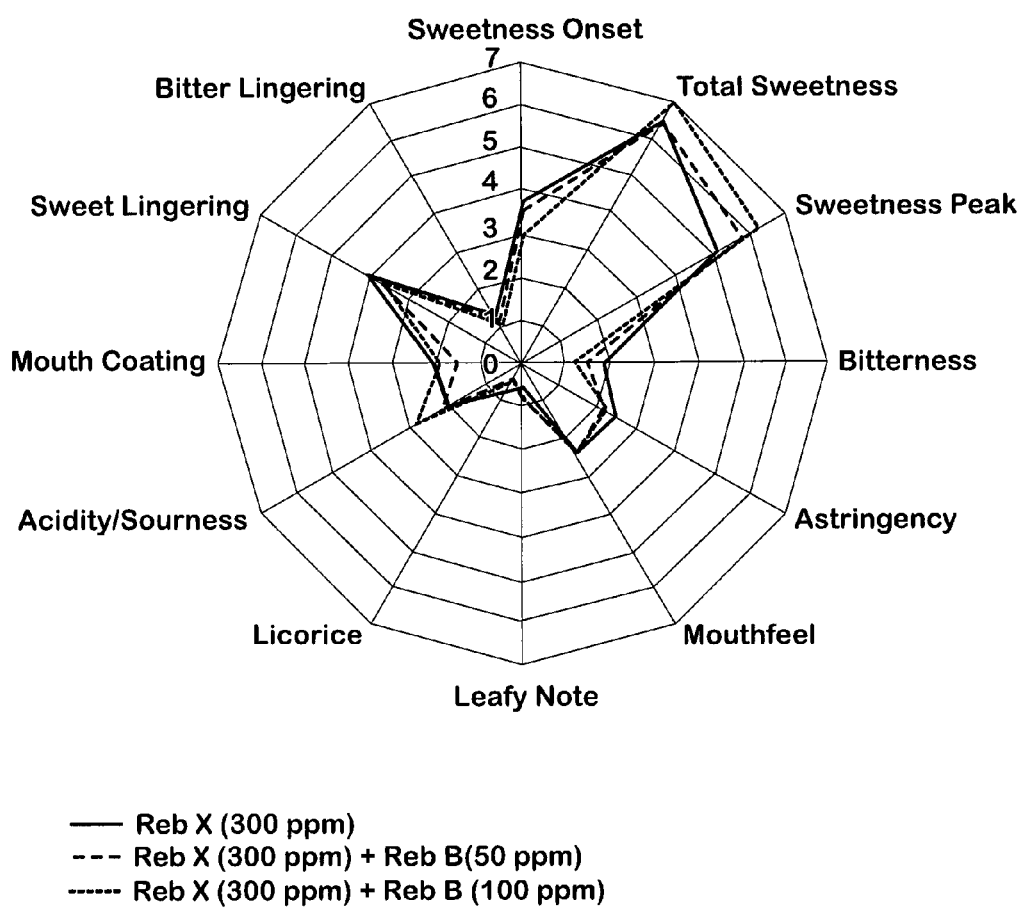
FIG. 14. shows a sensory comparison of Reb X and Reb B at various concentrations in acidified water.

The Reb X/Reb B blends showed increased sweetness (i.e. synergy) compared to Reb X alone (FIG. 14). The Reb X/Reb B blend also showed a more rounded sweetness profile with improvement in sweetness intensity, onset and bitterness perception compared to Reb X alone.

The Reb X/NSF-02 blends had an overall rounded taste profile (FIG. 13). 25 ppm NSF-02 shows a slight improvement in overall sweetness profile over Reb X alone, but had little impact on other attributes. The Reb X/NSF-02 blend with 100 ppm NSF-02 had delayed sweetness onset and a slight increased sweetness intensity.

Figure 15:
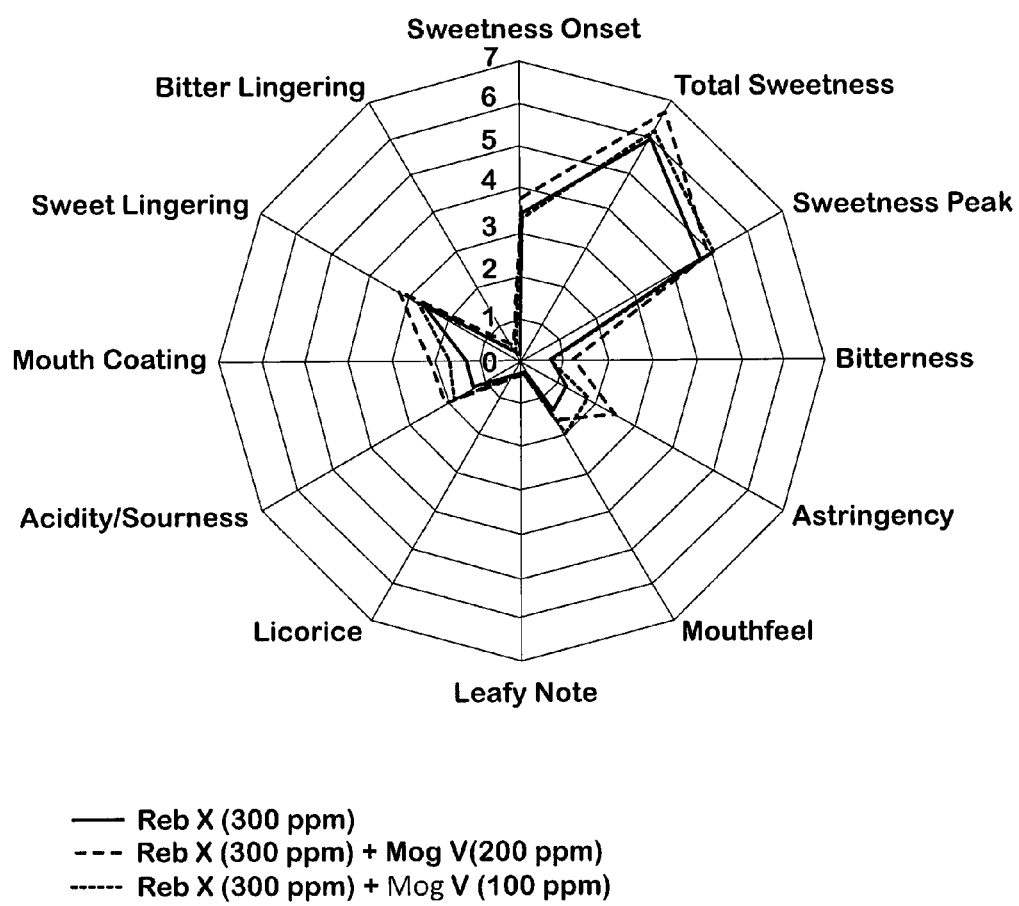
FIG. 15. shows as sensory comparison of Reb X and Mogroside V at various concentrations in acidified water.

The Reb X/mogroside V blends had increased astringency, sourness and mouthcoating compared to the other blends evaluated (FIG. 15). Higher mogroside V levels increased sweetness and sweetness lingering.

Figure 16:
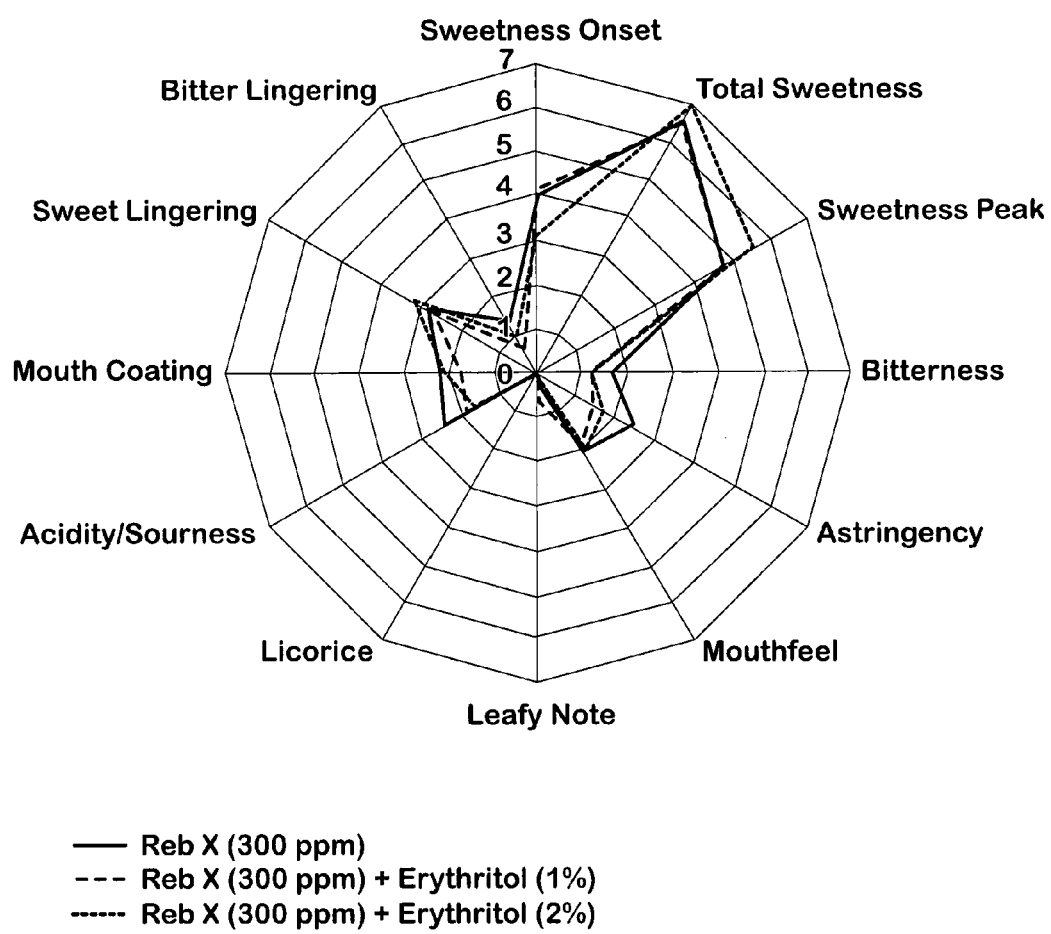
FIG. 16. shows a sensory comparison of Reb X and erythritol at various concentrations in acidified water.

The Reb X/erythritol blends had an overall rounded taste profile (FIG. 16). The blends had reduced acidity, reduced bitterness, reduced astringency and reduced bitterness lingering compared to Reb X alone. At levels above 1% (by weight), erythritol provides additional sweetness and earlier sweetness onset.

Blends of Reb X and Two Other Non-Caloric Sweeteners

Three sets of the following formulations were prepared:

Formulation 1: 300 ppm Reb X

Formulation 2: 300 ppm Reb X and 100 ppm Reb A

Formulation 3: 300 ppm Reb X and 100 ppm Reb D

Figure 17:
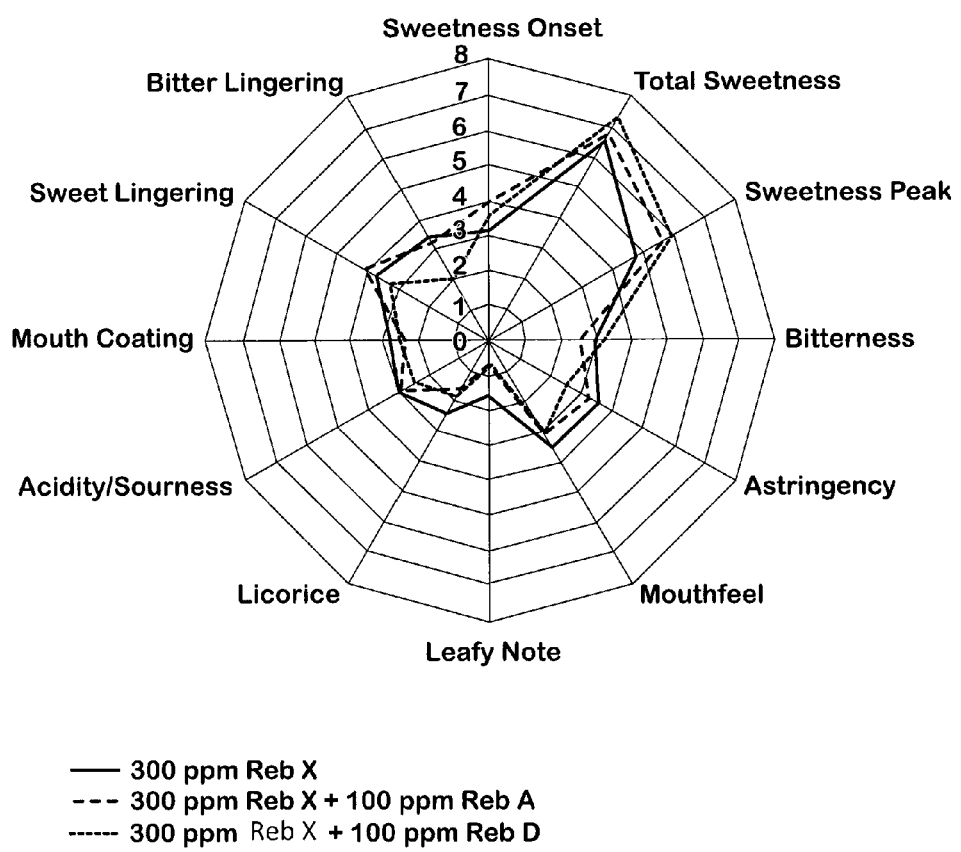
FIG. 17. shows a sensory comparison of (i) Reb X, (ii) Reb X and Reb A and (iii) Reb X and Reb D at various concentrations in acidified water.

All samples were prepared in acidified water. The sweetened samples were evaluated by 7 semi-trained panel members at room temperature. Samples were given to the panel members sequentially and coded with triple digit numbers. The order of sample presentation was randomized to avoid order of presentation bias. Water and unsalted crackers were provided in order to cleanse the palate. The panel members were asked to rate different attributes including sweetness onset, total sweetness, rounded sweetness, bitterness, acidity, leafy note, licorice, astringency, mouthfeel, mouth coating, sweet lingering, and bitter lingering. Samples were rated on a scale of zero (0) to ten (10), with zero indicating immediate onset, no intensity, watery/low viscosity, or very sharp peak, and ten indicating very delayed onset, high intensity, thick/high viscosity, or very round peak. One-way single factor ANOVA was used to analyze sensory results, where α=0.05. The results are shown in FIG. 17.

Discussion

Both formulation 2 (Reb X and Reb A) and formulation 3 (Reb X and Reb D) showed increased total sweetness and overall sweetness profile (sweetness peak) compared to Reb X alone. In addition, both formulations 2 and 3 showed decreased leafy note compared to Reb X alone. Formulation 3 showed higher improvement in sweetness intensity, overall sweetness profile, bitter lingering and sweet lingering.

Blends of Reb X and Three Other Non-Caloric Sweeteners

Three sets of the following formulations were prepared:

Formulation 1: 300 ppm Reb X,

Formulation 2: 200 ppm Reb X, 100 ppm Reb A and 100 ppm Reb D

Formulation 3: 300 ppm Reb X, 50 ppm Reb B and 50 ppm Reb D.

Figure 18:
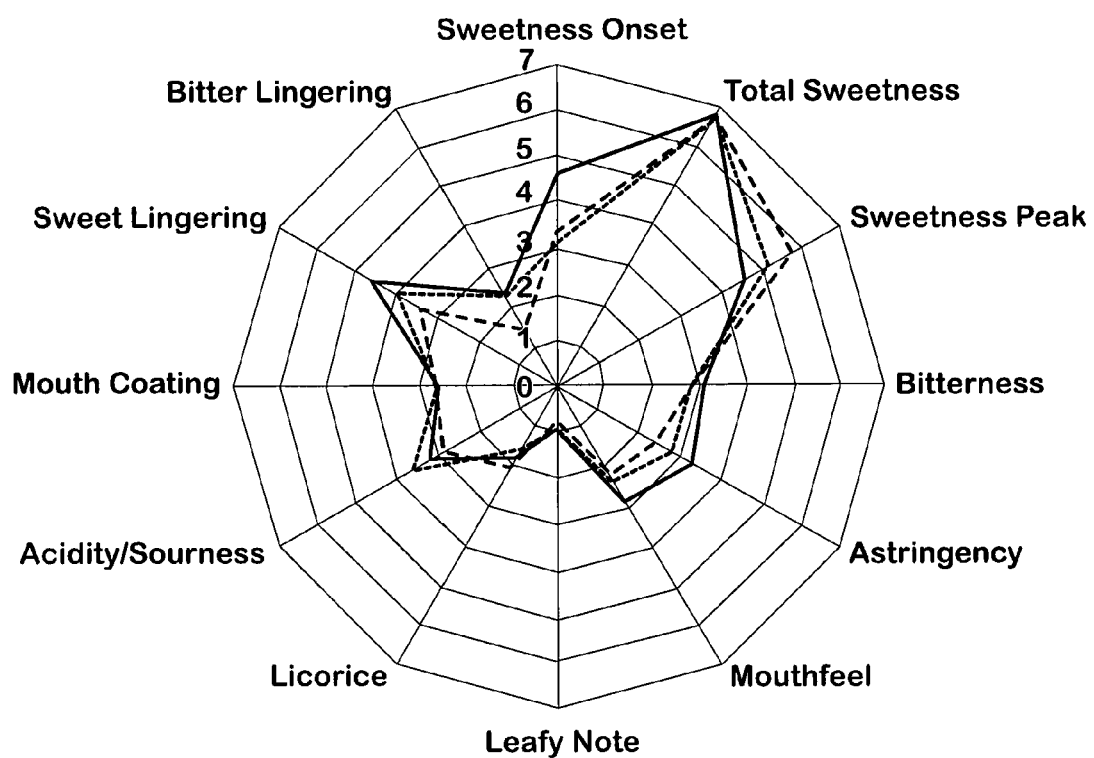
FIG. 18. shows a sensory comparison of (i) Reb X, (ii) Reb X, Reb X and Reb D and (iii) Reb X, Reb B and Reb D at various concentrations in acidified water.
Figure 19:
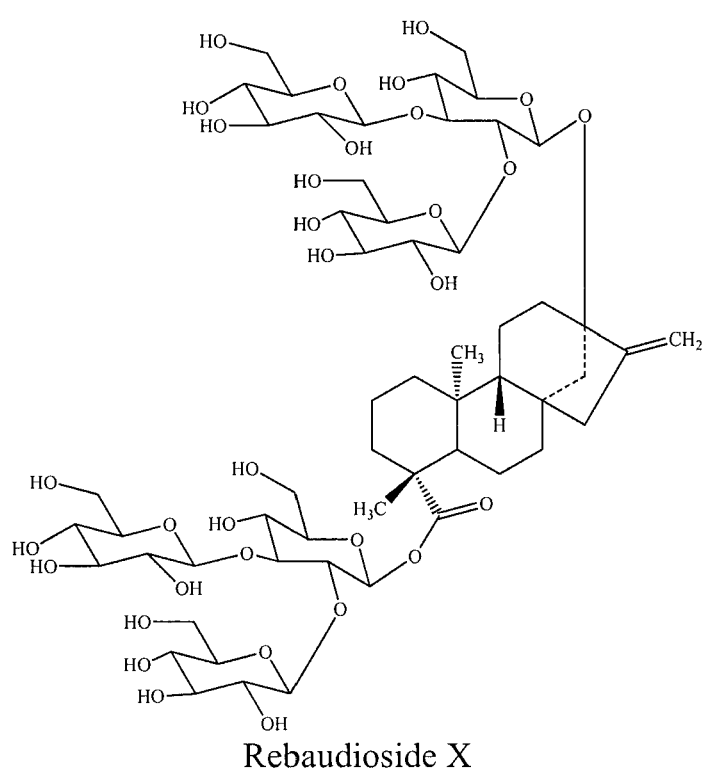
FIG. 19. shows the chemical structure of Reb X.

All samples were prepared in acidified water. The sweetened samples were evaluated by 11 semi-trained panel members at room temperature. Samples were given to the panel members sequentially and coded with triple digit numbers. The order of sample presentation was randomized to avoid order of presentation bias. Water and unsalted crackers were provided in order to cleanse the palate. The panel members were asked to rate different attributes including sweetness onset, total sweetness, rounded sweetness, bitterness, acidity, leafy note, licorice, astringency, mouthfeel, mouth coating, sweet lingering, and bitter lingering. Samples were rated on a scale of zero (0) to ten (10), with zero indicating immediate onset, no intensity, watery/low viscosity, or very sharp peak, and ten indicating very delayed onset, high intensity, thick/high viscosity, or very round peak. One-way single factor ANOVA was used to analyze sensory results, where α=0.05. The results are shown in FIG. 18.

Discussion

Both formulation 2 (Reb X, Reb A and Reb D) and formulation 3 (Reb X, Reb B and Reb D) showed increased sweetness onset, overall sweetness profile (sweetness peak) and decreased lingering (bitter and sweet lingering) compared to Reb X alone. Formulation 2, which had lower Reb X content compared to formulations 1 and 3, shoed a greater improvement in overall sweetness profile and lingering.

We claim:

1. A beverage comprising a sweetener composition comprising Reb X and a compound selected from the group consisting of Reb A, Reb B, Reb D, glucosylated steviol glycosides, Mogroside V, erythritol and combinations thereof, wherein the concentration of Reb X in the beverage is from about 50 ppm to about 600 ppm and the Reb X is present in an effective amount to provide a sucrose equivalence of greater than about 10% (w/v).

2. The beverage of claim 1, wherein the compound is Reb A.

3. The beverage of claim 1, wherein the compound is Reb B.

4. The beverage of claim 1, wherein the compound is Reb D.

5. The beverage of claim 1, wherein the compounds are Reb A and Reb D.

6. The beverage of claim 1, wherein the compounds are Reb B and Reb D.

7. The beverage of claim 1, wherein the pH of the beverage is from about 2 to about 5.

8. The beverage of claim 2, wherein Reb A comprises from about 5% to about 40% by weight of the sweetener composition.

9. The beverage of claim 2, wherein the concentration of Reb A in the beverage is about 10 ppm to about 500 ppm.

10. The beverage or claim 2, wherein the concentration of Reb X is about 300 ppm and the concentration of Reb A in the beverage is about 100 ppm.

11. The beverage of claim 3, wherein Reb B comprises from about 5% to about 40% by weight of the sweetener composition.

12. The beverage of claim 3, wherein the concentration of Reb B in the beverage is about 10 ppm to about 150 ppm.

13. The beverage or claim 3, wherein the concentration of Reb X is about 300 ppm and the concentration of Reb B in the beverage is from about 50 ppm to about 100 ppm.

14. The beverage of claim 4, wherein Reb D comprises from about 5% to about 40% by weight of the sweetener composition.

15. The beverage of claim 4, wherein the concentration of Reb D in the beverage is about 10 ppm to about 500 ppm.

16. The beverage or claim 4, wherein the concentration of Reb X is about 300 ppm and the concentration of Reb D in the beverage is about 100 ppm.

17. The beverage of claim 1, wherein the beverage is a zero-calorie beverage.

18. The beverage of claim 1, further comprising a carbohydrate sweetener.

19. The beverage of claim 1, wherein the beverage is selected from the group consisting of enhanced sparkling beverage, cola, lemon-lime flavored sparkling beverage, orange flavored sparkling beverage, grape flavored sparking beverage, strawberry flavored sparking beverage, grape flavored sparkling beverage, pineapple flavored sparkling beverage, ginger-ale, soft drink, root beer, fruit juice, fruit-flavored juice, juice drink, nectar, vegetable juice, vegetable-flavored juice, sports drink, energy drink, enhanced water drink, coconut water, tea-type drink, coffee, cocoa drink, beverage containing milk components, beverage containing cereal extract and a smoothie.

20. The beverage of claim 1, further comprising at least one functional ingredient selected from the group consisting of saponin, antioxidant, dietary fiber source, fatty acid, vitamin, glucosamine, mineral, preservative, hydration agent, probiotic, prebiotic, weight management agent, osteoporosis management agent, phytoestrogen, long chain primary aliphatic saturated alcohol, phytosteroland combinations thereof.

21. The beverage of claim 19, wherein the beverage is an enhanced water drink.

22. The beverage of claim 19, wherein the beverage is a soft drink.

23. The beverage of claim 2, wherein the concentration of Reb X is about 100 and the concentration of Reb A in the beverage is about 500.

24. The beverage of claim 2, wherein the concentration of Reb A is between about 100 and about 200 ppm and the concentration of Reb X in the beverage is about 500 ppm.

25. The beverage of claim 4, wherein the concentration of Reb X is about 500 and the concentration of Reb D in the beverage is about 100 ppm.

26. The beverage of claim 4, wherein the concentration of Reb X is about 100 to about 200 ppm and the concentration of Reb D in the beverage is about 100 ppm.

27. The beverage of claim 1, wherein the concentration of Reb X is at least about 100 ppm.

28. The beverage of claim 18, wherein the carbohydrate sweetener is selected from the group consisting of glucose, fructose, sucrose and combinations thereof.

29. The beverage of claim 19, wherein the beverage is a cola.

30. The beverage of claim 19, wherein the beverage is a lemon-lime flavored sparkling beverage.

31. The beverage of claim 19, wherein the beverage is a fruit juice.

32. The beverage of claim 19, wherein the beverage is a sports drink or energy drink.

33. The beverage of claim 20, wherein the at least one functional ingredient is a vitamin.

34. The beverage of claim 20, wherein the at least one functional ingredient is an antioxidant.

35. The beverage of claim 20, wherein the at least one functional ingredient is a mineral.

36. The beverage of claim 20, wherein the at least one functional ingredient is a preservative.

* * * * *